United States Patent
Reddy et al.

(10) Patent No.: US 8,058,313 B2
(45) Date of Patent: Nov. 15, 2011

(54) ALPHA, BETA-UNSATURATED SULFONES, SULFOXIDES, SULFONIMIDES, SULFINIMIDES, ACYLSULFONAMIDES AND ACYLSULFINAMIDES AND THERAPEUTIC USES THEREOF

(75) Inventors: E. Premkumar Reddy, Villanova, PA (US); M. V. Ramana Reddy, Upper Darby, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 1167 days.

(21) Appl. No.: 11/630,445

(22) PCT Filed: Jun. 23, 2005

(86) PCT No.: PCT/US2005/022394
§ 371 (c)(1),
(2), (4) Date: Jul. 2, 2007

(87) PCT Pub. No.: WO2006/025924
PCT Pub. Date: Mar. 9, 2006

(65) Prior Publication Data
US 2008/0070974 A1    Mar. 20, 2008

Related U.S. Application Data

(60) Provisional application No. 60/583,009, filed on Jun. 24, 2004.

(51) Int. Cl.
| | |
|---|---|
| A61K 31/10 | (2006.01) |
| A61K 31/12 | (2006.01) |
| A61K 31/381 | (2006.01) |
| C07D 333/10 | (2006.01) |
| C07C 49/217 | (2006.01) |
| C07C 317/10 | (2006.01) |
| C07C 317/24 | (2006.01) |

(52) U.S. Cl. .......... 514/679; 514/708; 514/709; 568/20; 568/34; 568/37; 568/36; 568/31; 568/325; 549/59

(58) Field of Classification Search .......... None
See application file for complete search history.

(56) References Cited

U.S. PATENT DOCUMENTS

| | | | |
|---|---|---|---|
| 6,046,239 A | 4/2000 | Lennox et al. | 514/563 |
| 6,201,154 B1 | 3/2001 | Reddy et al. | 568/28 |
| 6,359,013 B1 | 3/2002 | Reddy et al. | 514/710 |
| 6,414,034 B1 | 7/2002 | Reddy et al. | 514/710 |
| 6,486,210 B2 | 11/2002 | Reddy et al. | 514/708 |
| 6,498,277 B1 * | 12/2002 | Gervay-Hague et al. | 568/11 |
| 6,541,475 B2 | 4/2003 | Reddy et al. | 514/252.12 |
| 6,548,553 B2 | 4/2003 | Reddy et al. | 514/710 |
| 6,576,675 B1 | 6/2003 | Reddy et al. | 514/710 |
| 6,599,932 B1 | 7/2003 | Reddy et al. | 514/438 |
| 6,642,410 B2 | 11/2003 | Reddy et al. | 562/426 |
| 6,656,973 B2 | 12/2003 | Cosenza et al. | 514/710 |
| 6,667,346 B2 | 12/2003 | Reddy et al. | 514/710 |
| 6,762,207 B1 | 7/2004 | Reddy et al. | 514/709 |
| 6,767,926 B1 | 7/2004 | Cosenza et al. | 514/710 |
| 6,787,667 B2 | 9/2004 | Reddy et al. | 562/429 |
| 6,833,480 B2 | 12/2004 | Reddy et al. | 568/28 |
| 7,053,123 B2 | 5/2006 | Reddy et al. | 514/710 |
| 7,056,953 B2 | 6/2006 | Reddy et al. | 514/710 |
| 2003/0114538 A1 | 6/2003 | Reddy et al. | 514/709 |
| 2003/0114661 A1 | 6/2003 | Gervay-Hague et al. | 536/25.3 |
| 2005/0130942 A1 | 6/2005 | Reddy et al. | 514/114 |
| 2006/0167317 A1 | 7/2006 | Reddy et al. | 564/211 |

FOREIGN PATENT DOCUMENTS

| | | |
|---|---|---|
| WO | WO 00/77013 | 12/2000 |
| WO | WO 01/40188 | 6/2001 |
| WO | WO 01/78733 | 10/2001 |

OTHER PUBLICATIONS

Hadd, et al., "A novel reagent for the synthesis of geminal di-sulfones", *Tetrahedron Letters*, 42 (2001) 5137-5140.
Meadows, et al., "Synthesis and Biological Evaluation of Geminal Disulfones as HIV-1 Integrase Inhibitors", *J. Med. Chem.* 2005, 48, 4526-4534.

* cited by examiner

*Primary Examiner* — Yong Chu
*Assistant Examiner* — Michael Barker
(74) *Attorney, Agent, or Firm* — Drinker Biddle & Reath LLP

(57) ABSTRACT

α,β-Unsaturated sulfones, sulfoxides, sulfonimides, sulfinimides, acylsulfonamides and acylsulfinamides of Formula I:

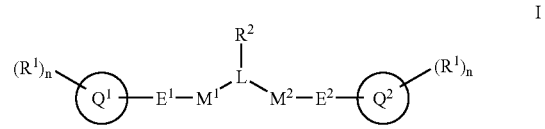

wherein $R^1$, $R^2$, $M^1$, $M^2$, L, $E^1$, $E^2$, $Q^1$, $Q^2$ and n are as defined herein, are useful as anti-angiogenesis agents, as agents for treatment of age related senile dementia, and as antiproliferative agents including, for example, as anticancer agents.

33 Claims, No Drawings

ALPHA, BETA-UNSATURATED SULFONES, SULFOXIDES, SULFONIMIDES, SULFINIMIDES, ACYLSULFONAMIDES AND ACYLSULFINAMIDES AND THERAPEUTIC USES THEREOF

CROSS-REFERENCE TO RELATED APPLICATION

This application claims the benefit of copending U.S. Provisional Application Ser. No. 60/583,009, filed Jun. 24, 2004, the entire disclosure of which is incorporated herein by reference.

FIELD OF THE INVENTION

The invention relates to α,β-unsaturated sulfones, sulfoxides, sulfonimides, sulfinimides, acylsulfonamides and acylsulfinamides, and to pharmaceutical compositions containing such compounds. The invention further relates to methods of treatment comprising administration of such compounds.

BACKGROUND OF THE INVENTION

A. Proliferative Disorders

Extracellular signals received at transmembrane receptors are relayed into the cells by signal transduction pathways (Pelech et al., Science 257:1335 (1992)) which have been implicated in induction of cell proliferation, differentiation or apoptosis (Davis et al., J. Biol. Chem. 268:14553 (1993)). One such signal transduction pathway is the mitogen activated protein kinase (MAPK) cascade. See, Nishida et al., Trends Biochem. Sci. 18:128 (1993) and Blumer et al., Trends Biochem. Sci. 19:236 (1994). Much of the MAPK pathway is conserved over different species. The most thoroughly studied of the MAPKs are extra cellular signal regulated kinases (ERKs) (Posada et al., Science 255:212 (1992); Biggs III et al., PNAS. USA 89:6295 (1992); and Garner et al., Genes Dev. 6:1280 (1992)) and c-Jun NH$_2$ terminal kinases (JNKs) (Hibi et al., Genes Dev. 7:2135 (1993)). JNKs are members of a class of stress activated protein kinases (SAPK) and are shown to be activated by treatment of cells with UV radiation, pro-inflammatory cytokines and environmental stress (Derijard et al., Cell 1025 (1994)). Activation of ERK has been shown to involve kinase mediated phosphorylation of threonine and tyrosine residues, which signals cell proliferation. In contrast, activation of JNKs leads to cell growth inhibition and apoptosis.

Protein tyrosine kinases are enzymes which catalyze a well defined chemical reaction: the phosphorylation of a tyrosine residue (Hunter et al., Ann. Rev. Biochem. 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., Eur. J. Biochem. 135:583-589 (1983)).

The best understood MAPK pathway involves extracellular signal-regulated kinases which constitute the Ras/Raf/MEK/ERK kinase cascade (Boudewijn et al., Trends Biochem. Sci. 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

B. Angiogenesis Inhibition

Angiogenesis, or development of new blood vessels, is implicated in a host of diseases including tumorigenesis, metastasis and tumor growth, retinopathies, neovascular ocular disorders, and postangioplasty or postatherectomy restenosis. See, Bicknell et al. (1996) Curr. Opin. Oncol. 8: 60-65; Gariano et al. (1996) Survey Ophthalmol. 40: 481-490; and Wilcox, J. N. (1993) Am. J. Cardiol. 72: 88E-95E).

Recent research has indicated that differences in the production of vascular endothelial growth factor (VEGF) and sFlt-1 by smooth muscle cells and human umbilical endothelial cells (HUVECs) are consistent with the role of these cells in angiogenesis. See, Belgore et al., Eur. J. Clin. Invest. 2003, 33(10), page 833-39. Studies have indicated a therapeutic potential of placental growth factor (PlGF) and its receptor FLT1 in angiogenesis. An antibody against FLT1 has been shown to suppress neovascularization in tumors and ischemic retina, and angiogenesis and inflammatory joint destruction in autoimmune arthritis. See, Luttun et al., Nat Med., 2002, 8(8) page 831-40.

Expression and secretion of angiogenic factors by tumors has been investigated. It has been suggested that because tumors express multiple angiogenic factors, broad spectrum antagonists of angiogenesis can provide effective means of tumor stabilization. Anti-angiogenic approaches to tumor therapy have been defined to involve interference with growth, migration and differentiation of blood vessels associated with tumor growth. Anti-angiogenic agents have been categorized to include protease inhibitors, modulators of cytokines, heparin-like molecules, and antagonists of vascular growth factors. Growth factor antagonists have been categorized to include heparin-like molecules, angiogenin antagonists, antisense fibroblast growth factor, DS 4152, suramin analogs, and protein-bound saccharide-K (Bicknell et al., Id.).

C. Biological Activity of Curcumin

Curcumin is a compound that is isolated from the commonly used spice turmeric. The structure of curcumin is shown in Scheme 1.

Scheme 1

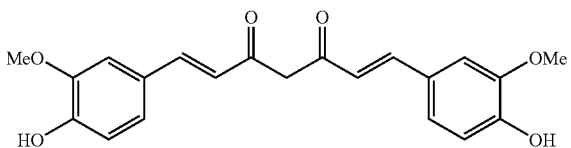

Curcumin has been shown to inhibit the progression of chemically induced colon and skin cancers in animal models. In HT29 cells curcumin-induced modulation of genes involved in transition through the G2/M phase has been observed to correspond to a cell cycle arrest in the G2/M phase. See, van Erk et al., J. of Carcinogenesis 2004, 3:8. Curcumin has also been observed to downregulate expression of some cytochrome P450 genes and to affect expression of metallothionein genes, tubulin genes, p53 and other genes involved in colon carcinogenesis. Id.

The antiproliferative effects of curcumin are believed to be related to inhibition of aminopeptidase N (APN), an enzyme that is linked to invasiveness and angiogenesis in tumors. See, Kwon et al., Chem. Biol., 10, 695 (2003). Curcumin has also been shown to have direct antiangiogenic activity in vitro and in vivo. See, Arbiser et al., Mol Med., 1998, 4(6): page 376-83.

Curcumin has also been shown to be effective in the dinitrobenzene sulfuric acid (DNB) induced murine colitis model, which is an experimental model of IBD. See, Salh et al., *Am. J Phys. Gastrointestinal and Liver Physiology,* 2003 285(1), page 235-43. In the DNB-induced murine colitis model, curcumin was observed to attenuate macroscopic damage, to improve intestinal cell function, and to inhibit the nuclear transcription factor NF-κB activation in the colon.

Curcumin is also effective in biological assays that are predictive of activity in age-related neurodegenerative diseases such as Alzheimer's Disease (AD) and presenile dementia. Curcumin has been shown to reduce the oxidative damage (isoprostane levels) and synaptophysin loss induced by intracerebroventricular infusion of beta amyloid (Abeta) peptides. See, Chu et al., *Neurobiol. Aging,* 2001, 22(6): page 993-1005.

Cancer and other proliferative disorders remain a major unmet medical need. Cancer treatments often comprise surgery, chemotherapeutic treatments, radiation treatment or combinations thereof. Chemotherapeutic treatments for most cancers only delay disease progression rather than providing a cure. Cancers often become refractory to chemotherapy via development of multidrug resistance. Particular cancers are inherently resistant to some classes of chemotherapeutic agents. See DeVita et al, Principles of Cancer Management: Chemotherapy. In: Cancer. Principles and Practice of Oncology, 5th edition, Lippincott-Raven, Philadelphia, N.Y. (1977), pp. 333-347.

Progress continues in treatment of proliferative disorders such as cancer, and in the treatment of angiogenesis-mediated disorders. However, there remains a need to develop new therapeutic agents.

Definitions

General

The term "individual" includes human beings and non-human animals.

The expression "effective amount" when used to describe therapy to an individual suffering from a cancer or other disorder which manifests abnormal cellular proliferation, refers to the amount of a compound according to Formula I that inhibits the growth or proliferation of tumor cells, or alternatively induces apoptosis of cancer cells, preferably tumor cells, resulting in a therapeutically useful and selective cytotoxic effect on proliferative cells.

The expression "effective amount" when used to describe therapy to an individual suffering from an angiogenesis-mediated disorder, refers to the amount of a compound according to Formula I that inhibits or reduces the abnormal growth or proliferation of vascular tissue.

The expression "effective amount" when used to describe therapy to an individual suffering from an age related senile dementia, refers to the amount of a compound according to Formula I that serves to slow, halt or reverse the progress of the disorder.

The term "proliferative disorder" means a disorder wherein cells are made by the body at an atypically accelerated rate.

The term "angiogenesis" means the generation of new blood vessels into a tissue or organ.

The term "angiogenesis-mediated disorder" means an adverse biological or biochemical condition that is exacerbated by angiogenesis, i.e., the abnormal formation of new blood vessels. Examples of such disorders include, but are not limited to, tumorigenesis, neovascularization, and hyper-proliferation of vascular smooth muscle cells.

Chemical

The term "alkyl", by itself, or as part of another substituent, e.g., haloalkyl or aminoalkyl, means, unless otherwise stated, a saturated hydrocarbon radical having the number of carbon atoms designated (i.e. $C_1$-$C_6$ means the group contains one, two, three, four, five or six carbons) and includes straight, branched chain, cyclic and polycyclic groups. Examples include: methyl, ethyl, propyl, isopropyl, butyl, isobutyl, tert-butyl, pentyl, neopentyl, hexyl, cyclohexyl, norbornyl and cyclopropylmethyl. Preferred alkyl groups are —($C_1$-$C_6$) alkyl. Most preferred is —($C_1$-$C_3$)alkyl, particularly ethyl, methyl and isopropyl.

The expression "substituted alkyl" means alkyl, as defined above, substituted by one, two or three substituents preferably independently selected from the group consisting of halogen, —OH, —O($C_1$-$C_4$)alkyl, —$NH_2$, —$N(CH_3)_2$, —$CO_2H$, —$CO_2$($C_1$-$C_4$)alkyl, —$CF_3$, —$CONH_2$, —$SO_2NH_2$, —C(=NH)$NH_2$, —CN and —$NO_2$. More preferably, the substituted alkyl contains one or two substituents independently selected from the group consisting of halogen, —OH, $NH_2$, —$N(CH_3)_2$, —$CF_3$ and —$CO_2H$; most preferably, independently the group consisting of halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical having the designated number of carbons. The expression —C(=O)($C_1$-$C_4$)alkylene-R includes one, two, three and four carbon alkylene groups. A substitution of a group such as R on alkylene may be at any substitutable carbon, i.e., the group, —C(=O)($C_4$ alkylene)R, includes, for example (a), (b) and (c), in Scheme 2, below:

Scheme 2

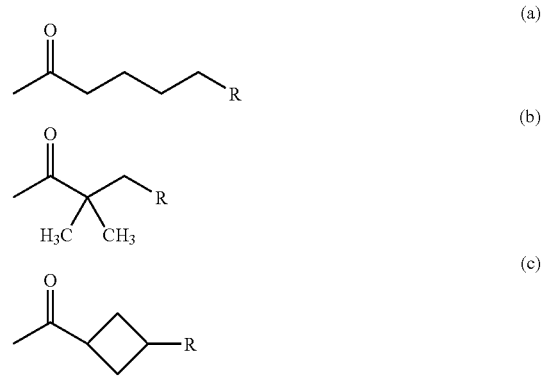

The term "amine" or "amino" refers to radicals of the general formula NRR', wherein R and R' are independently hydrogen or a hydrocarbyl radical, or wherein R and R' combined form a heterocycle. Examples of amino groups include: —$NH_2$, methyl amino, diethyl amino, anilino, benzyl amino, piperidinyl, piperazinyl and indolinyl.

The term "aromatic" refers to a carbocycle or heterocycle having one or more polyunsaturated rings having aromatic character (4n +2) delocalized π (pi) electrons.

The term "aryl" employed alone or in combination with other terms, means, unless otherwise stated, a carbocyclic aromatic group containing one or more rings (typically one, two or three rings) wherein such rings may be attached together in a pendent manner, such as a biphenyl, or may be fused, such as naphthalene. Examples include phenyl, anthracyl and naphthyl. Preferred are phenyl and naphthyl, most preferred is phenyl.

The term "aryl-($C_1$-$C_3$)alkyl" means a radical wherein a one to three carbon alkylene chain is attached to an aryl group, e.g., —$CH_2CH_2$-phenyl. Preferred is aryl($CH_2$)— and aryl ($CH(CH_3)$)—. The term "substituted aryl-($C_1$-$C_3$)alkyl" means an aryl-($C_1$-$C_3$)alkyl radical in which the aryl group is substituted. Preferred is substituted aryl($CH_2$)—. Similarly, the term "heteroaryl($C_1$-$C_3$)alkyl" means a radical wherein a one to three carbon alkylene chain is attached to a heteroaryl group, e.g., —$CH_2CH_2$-pyridyl. Preferred is heteroaryl ($CH_2$)—. The term "substituted heteroaryl-($C_1$-$C_3$)alkyl" means a heteroaryl-($C_1$-$C_3$)alkyl radical in which the heteroaryl group is substituted. Preferred is substituted heteroaryl($CH_2$)—.

The term "arylene," by itself or as part of another substituent means, unless otherwise stated, a divalent aryl radical. Preferred are divalent phenyl radicals, particularly 1,4-divalent phenyl radicals.

The term "cycloalkyl" refers to ring-containing alkyl radicals. Examples include cyclohexyl, cyclopentyl, cyclopropyl methyl and norbornyl.

The term "hydrocarbyl" refers to any moiety comprising only hydrogen and carbon atoms. Preferred hydrocarbyl groups are ($C_1$-$C_{12}$)hydrocarbyl, more preferred are ($C_1$-$C_8$) hydrocarbyl, most preferred are benzyl and —($C_1$-$C_6$)alkyl.

The term "hydrocarbylene" by itself or as part of another substituent means, unless otherwise stated, a divalent moiety comprising only hydrogen and carbon atoms. A substitution of another group —R on hydrocarbylene may be at any substitutable carbon, i.e., the expression —($C_1$-$C_6$ hydrocarbylene)-R includes, for example, the structures shown in Scheme 3:

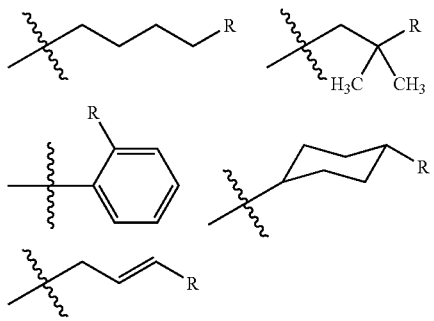

Scheme 3

The term "heteroalkyl" by itself or in combination with another term means, unless otherwise stated, a stable straight or branched chain radical consisting of the stated number of carbon atoms and one or two heteroatoms selected from the group consisting of O, N, and S, wherein the sulfur heteroatoms may be optionally oxidized and the nitrogen heteroatoms may be optionally quaternized or oxidized. The oxygens bonded to oxidized sulfur or nitrogen may be present in addition to the one or two heteroatoms in the heteroalkyl group. The heteroatom(s) may occupy any position in the heteroalkyl group, including the attachment position of the heteroalkyl group and a terminal atom of the heteroalkyl group. Examples of heteroalkyl groups include: —S—$CH_2$—$CH_2$—$CH_3$, —$CH_2$—$CH_2CH_2$—OH, —$CH_2$—$CH_2$—NH—$CH_3$, —$CH_2$—$SO_2$—NH—$CH_3$, —$CH_2$—S—$CH_2$—$CH_3$ and —$CH_2CH_2$—S(=O)—$CH_3$. Two heteroatoms may be bonded to each other, such as, for example, —$CH_2$—NH—$OCH_3$, or —$CH_2$—$CH_2$—S—S—$CH_3$.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A monocyclic heteroaryl group is preferably a 5-, 6-, or 7-membered ring, examples of which are pyrrolyl, furyl, thienyl, pyridyl, pyrimidinyl and pyrazinyl. A polycyclic heteroaryl may comprise multiple aromatic rings or may include one or more rings which are partially saturated.

Examples of polycyclic heteroaryl groups containing a partially saturated ring include tetrahydroquinolyl and 2,3-dihydrobenzofuryl. For compounds according to Formula I, below, the attachment point on the aromatic group $R^2$ is understood to be on an atom which is part of an aromatic monocyclic ring or a ring component of a polycyclic aromatic which is itself an aromatic ring. For example, on the partially saturated heteroaryl ring, 1,2,3,4-tetrahydroisoquinoline, attachment points are ring atoms at the 5-, 6-, 7- and 8-positions. The attachment point on aromatic group $R^2$ may be a ring carbon or a ring nitrogen and includes attachment to form aromatic quaternary ammonium salts such as pyridinium.

Examples of non-aromatic heterocycles include monocyclic groups such as: aziridinyl, oxiranyl, thiiranyl, azetidinyl, oxetanyl, thietanyl, pyrrolidinyl, pyrrolinyl, imidazolinyl, pyrazolidinyl, dioxolanyl, sulfolanyl, 2,3-dihydrofuranyl, 2,5-dihydrofuranyl, tetrahydrofuranyl, thiolanyl, piperidinyl, 1,2,3,6-tetrahydropyridinyl, 1,4-dihydropyridinyl, piperazinyl, morpholinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepinyl, 4,7-dihydro-1,3-dioxepinyl and hexamethyleneoxide.

Examples of monocyclic heteroaryl groups include, for example, six-membered monocyclic aromatic rings such as, for example, pyridyl, pyrazinyl, pyrimidinyl and pyridazinyl; and five-membered monocyclic aromatic rings such as, for example, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, indolinyl, quinolyl, tetrahydroquinolyl, isoquinolyl, 1,2,3,4-tetrahydroisoquinolyl, cinnolinyl, quinoxalinyl, quinazolinyl, phthalazinyl, 1,8-naphthyridinyl, 1,4-benzodioxanyl, chromene-2-one-yl (coumarinyl), dihydrocoumarin, chromene-4-one-yl, benzofuryl, 1,5-naphthyridinyl, 2,3-dihydrobenzofuryl, 1,2-benzisoxazolyl, benzothienyl, benzoxazolyl, benzthiazolyl, purinyl, benzimidazolyl, benztriazolyl, thioxanthinyl, benzazepinyl, benzodiazepinyl, carbazolyl, carbolinyl, acridinyl, pyrrolizidinyl and quinolizidinyl.

The term "heteroarylene," by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from the group consisting of pyridine, piperazine, pyrimidine, pyrazine, furan, thiophene, pyrrole, thiazole, imidazole and oxazole.

The aforementioned listing of heterocyclyl and heteroaryl moieties is intended to be representative, not limiting.

The terms "halo" or "halogen" by themselves or as part of another substituent, e.g., haloalkyl, mean, unless otherwise stated, a fluorine, chlorine, bromine, or iodine atom. Fluorine, chlorine and bromine are preferred. Fluorine and chlorine are most preferred.

The term "haloalkyl" means, unless otherwise stated, an alkyl group as defined herein containing at least one halogen substituent and no substituent that is other than halogen. Multiple halogen substituents, up to substitution of all substitutable hydrogens on the alkyl group may be the same or different. Preferred haloalkyl groups include, for example, perfluoro($C_1$-$C_6$)alkyl, trifluoro($C_1$-$C_6$)alkyl, gem-difluoro ($C_1$-$C_4$)alkyl and chloro($C_1$-$C_4$)alkyl. More preferred haloalkyl groups include, for example, —$CF_3$, —$C_2F_5$, —$CH_2CF_3$, —$CHF_2$, —$CF_2CH_3$ and —$CH_2Cl$.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "trifluoro($C_x$-$C_y$)alkyl" means an alkyl group with a minimum of x carbon atoms and a maximum of y carbon atoms, wherein the three hydrogen atoms on a terminal carbon (—$CH_3$) are replaced by fluorine atoms. Examples include —$CH_2CF_3$, —$(CH_2)_2$—$CF_3$ and —$CH(CH_3)$—$CF_3$.

The term "gem-difluoro($C_x$-$C_y$)alkyl" means an alkyl group with a minimum of x carbon atoms and a maximum of y carbon atoms, wherein one carbon atom is geminally substituted with two fluorine atoms. The fluorine-substituted carbon may be any carbon in the chain having at least two substitutable hydrogens, including the a terminal —$CH_3$ group and the proximal carbon through which the difluoro ($C_x$-$C_y$)alkyl is bonded to the rest of the molecule. Examples include —$CH_2CF_2H$, —$(CH_2)_2$—$CF_2H$ and —$CF_2$—$CH_3$ and 3,3-difluorocyclohexyl.

The term "substituted" means that an atom or group of atoms has replaced hydrogen as the substituent attached to another group. For aryl and heteroaryl groups, the term "substituted" refers to any level of substitution, namely mono-, di, tri-, tetra-, or penta-substitution, where such substitution is permitted. The substituents are independently selected, and substitution may be at any chemically accessible position.

The naming of compounds disclosed herein was done by employing the structure naming programs included in ChemDraw software packages. The compounds, were named using the "Structure to Name" program within ChemDraw Ultra Version 8.0 (© 1985-2003, CambridgeSoft Corporation, 100 Cambridgepark Drive, Cambridge, Mass. 02140 USA).

SUMMARY OF THE INVENTION

It is an object of the invention to provide compounds, compositions and methods for the treatment of cancer and other proliferative disorders. It is further an object of the invention to provide methods of treatment of angiogenesis-mediated disorders. The biologically active compounds are in the form of α,β-unsaturated sulfones, sulfoxides, sulfonimides, sulfinimides, acyl sulfonamides, and acyl sulfinamides.

I. Compounds According to the Invention

According to one embodiment of the invention, novel compounds are provided according to Formula I:

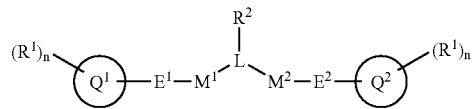

wherein:
$Q^1$ and $Q^2$ are independently selected from the group consisting of aryl and heteroaryl;
each $R^1$ is independently selected from the group consisting of halogen, —($C_1$-$C_8$)hydrocarbyl, —C(=O)$R^y$, —$NR^w_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —$NO_2$, —CN, —$OR^w$, —OC(=O)$R^Y$, —OCH($R^z$)C(=O)$R^y$, —$OSO_2R^y$—O($C_1$-$C_4$)alkylene-$CO_2R^w$, —OP(=O) ($OR^w$)$_2$, —O($C_2$-$C_6$)alkylene-N($CH_3$)$_2$, —O($C_1$-$C_6$)haloalkyl, —P(=O)($OR^w$)$_2$, —$SO_2$N($R^w$)$R^x$, —NHC(=NH) $NHR^x$, —($C_1$-$C_6$)haloalkyl and heteroalkyl;
each $R^w$ is independently —H or —($C_1$-$C_8$)hydrocarbyl;
each $R^x$ is independently —H, —($C_1$-$C_8$)hydrocarbyl or —C(=O)($C_1$-$C_8$)hydrocarbyl;
each $R^y$ is independently selected from the group consisting of —H, —($C_1$-$C_8$)hydrocarbyl, —O($C_1$-$C_8$)hydrocarbyl, substituted phenyl, substituted heterocyclyl($C_1$-$C_3$)alkyl, heteroaryl($C_1$-$C_3$)alkyl, —($C_2$-$C_{10}$)heteroalkyl, —($C_1$-$C_6$) haloalkyl, —C($R^z$)$NHR^x$, —N($R^w$)$R^x$, —($C_1$-$C_3$)alkyleneNH$_2$, —($C_1$-$C_3$)alkyleneN($CH_3$)$_2$, —($C_1$-$C_3$)perfluoroalkyleneN($CH_3$)$_2$, —($C_1$-$C_3$)alkyleneN$^+$(($C_1$-$C_3$)alkyl)$_3$, —($C_1$-$C_3$)alkylene-N$^+$($CH_2CH_2OH$)$_3$, —($C_1$-$C_3$)alkylene-$OR^x$, —($C_1$-$C_4$)alkylene-$CO_2R^w$, —($C_1$-$C_4$)alkylene-$CO_2N$ ($R^w$)$R^x$, —($C_1$-$C_4$)alkylene-C(=O)halogen, halo($C_1$-$C_3$) alkyl and —($C_1$-$C_4$)perfluoroalkylene-$CO_2R^w$;
each $R^z$ is independently selected from the group consisting of —H, —($C_1$-$C_6$)alkyl, —$(CH_2)_3$—NH—C($NH_2$) (=NH), —$CH_2C$(=O)$NH_2$, —$CH_2COOH$, —$CH_2SH$, —$(CH_2)_2C$(=O)—$NH_2$, —$(CH_2)_2CO_2H$, —$CH_2$-(2-imidazolyl), —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl) and —$CH_2$-(4-hydroxyphenyl);
each n is independently 0, 1, 2, 3, 4 or 5; preferably 1, 2, 3, 4 or 5; more preferably 1, 2, 3 or 4; most preferably 1, 2 or 3;
$M^1$ and $M^2$ are independently —$SO_2$—, —S(=O)— or —C(=O)—;
L is CH or N;
$R^2$ is selected from the group consisting of —H and —($C_1$-$C_6$)alkyl, preferably —H and —($C_1$-$C_6$)alkyl, more preferably —H and —$CH_3$, most preferably —H; and
$E^1$ and $E^2$ are independently selected from the group consisting of a carbon-carbon double bond in the (E)-configuration and a carbon-carbon double bond in the (Z)-configuration;
provided that:
(i) when one of $M^1$ and $M^2$ is —$SO_2$—, then the other of $M^1$ and $M^2$ is other than —S(=O)—;
(ii) when one of $M^1$ and $M^2$ is —C(=O)—, then the other of $M^1$ and $M^2$ is other than —C(=O)—;
(iii) when one of $E^1$ and $E^2$ is a carbon-carbon double bond in the (Z)-configuration; then the other of $E^1$ and $E^2$ is a carbon-carbon double bond in the (E)-configuration; and
(iv) when L is CH, $R^2$ is —H, $M^1$ and $M^2$ are —$SO_2$—, and $Q^1$ and $Q^2$ are phenyl; then at least one n is greater than zero, and at least one substituent $R^1$ is other than —OH, —OC(=O)$CH_3$, —C(=O)$CH_3$, —$OCH_3$, —Br, —I, —$NO_2$, —$CO_2$($C_1$-$C_8$)hydrocarbyl, —$SO_3$($C_1$-$C_8$)hydrocarbyl, —P(=O)(OR$^w$)$_2$, and —OP(=O)(OR$^w$)$_2$; or a salt, preferably a pharmaceutically-acceptable salt, of such a compound.

According to some embodiments, M$^1$ and M$^2$ are both —SO$_2$—. According to other embodiments, M$^1$ and M$^2$ are both —SO—. According to still other embodiments, one of M$^1$ or M$^2$ is —SO$_2$— and the other of M$^1$ or M$^2$ is —C(=O)—. According to still other embodiments, one of M$^1$ or M$^2$ is —SO— and the other of M$^1$ or M$^2$ is —C(=O)—.

According to some embodiments, both E$^1$ and E$^2$ are carbon-carbon double bonds in the (E)-configuration. According to other embodiments, one of E$^1$ and E$^2$ is a carbon-carbon double bond in the (E)-configuration and the other of E$^1$ and E$^2$ is a carbon-carbon double bond in the (Z)-configuration.

According to some embodiments of the invention, Q$^1$ is heteroaryl, preferably monocyclic heteroaryl.

According to some embodiments of the invention, Q$^2$ is heteroaryl, preferably monocyclic heteroaryl.

According to some embodiments of the invention, Q$^1$ and Q$^2$ are heteroaryl, preferably monocyclic heteroaryl.

According to some embodiments of the invention, Q$^1$ is aryl, preferably phenyl.

According to other embodiments of the invention, Q$^2$ is aryl, preferably phenyl.

According to still other embodiments of the invention, Q$^1$ and Q$^2$ are aryl, preferably phenyl.

According to some embodiments of the invention, R$^w$ is —H or —(C$_2$-C$_8$)hydrocarbyl. According to other embodiments, R$^w$ is —(C$_2$-C$_8$)hydrocarbyl. According to still other embodiments of the invention, R$^w$ is —H.

According to some embodiments, —R$^1$ substituents on di-substituted phenyl or six-membered heteroaryl Q$^1$ and Q$^2$ groups are independently placed at the 2- and 4-positions of the ring. According to other embodiments, —R$^1$ substituents on di-substituted phenyl or six-membered heteroaryl Q$^1$ and Q$^2$ groups are at the 3- and 4-positions of the ring. According to still other embodiments, —R$^1$ substituents on di-substituted phenyl or six-membered heteroaryl Q$^1$ and Q$^2$ groups are at the 2- and 6-positions of the ring.

According to some embodiments, a single —R$^1$ substituent on a phenyl or six-membered heteroaryl Q$^1$ or Q$^2$ group is at the 2- or 4-position of the ring.

According to some embodiments, —R$^1$ substituents on tri-substituted phenyl or six-membered heteroaryl Q$^1$ and Q$^2$ groups are independently placed at the 2-, 4- and 6-positions of the ring. According to other embodiments, —R$^1$ substituents on tri-substituted phenyl or six-membered heteroaryl Q$^1$ and Q$^2$ groups are at the 3-, 4- and 5-positions of the ring.

Substituted phenyl R$^y$ groups are preferably mono- di- or tri-substituted, more preferably mono- or di-substituted, most preferably mono-substituted.

Substituents on substituted phenyl R$^y$ groups are preferably selected from the group consisting of halogen, —NH$_2$, —NO$_2$, N-methylpiperazinyl and —OR$^x$.

Substituted heterocyclyl(C$_1$-C$_3$)alkyl R$^y$ groups are preferably mono- or di-substituted, more preferably mono-substituted.

Substituents on substituted heterocyclyl(C$_1$-C$_3$)alkyl R$^y$ groups are preferably —(C$_1$-C$_7$)hydrocarbyl or —C(=O) (C$_1$-C$_7$)hydrocarbyl, more preferably —(C$_1$-C$_6$)alkyl or —C(=O) (C$_1$-C$_6$)alkyl.

According to some embodiments of the compounds of the invention, one n is greater than zero. According to other embodiments each n is greater than zero.

According to some embodiments of the compounds of the invention, one n is greater than 1. According to other embodiments each n is greater than 1.

According to some embodiments of the compounds of the invention, one n is greater than 2. According to other embodiments each n is greater than 2.

According to some embodiments of the invention, one or more R$^1$ groups are independently selected from the group consisting of halogen other than bromine and iodine, —(C$_1$-C$_8$)hydrocarbyl, —C(=O)R$^y$ other than —C(=O)CH$_3$ and —CO$_2$(C$_1$-C$_8$)hydrocarbyl, —NR$^w$$_2$, —N(R$^w$)C(=O)R$^y$, —N(R$^w$)CH(R$^z$)C(=O)R$^y$, —N(R$^w$)SO$_2$R$^y$, —N(R$^w$)(C$_1$-C$_4$)alkylene-CO$_2$R$^w$, —CN, —OR$^w$ other than —OH and OCH$_3$, —OC(=O)R$^y$, —OCH(R$^z$)C(=O)R$^y$, —OSO$_2$R$^y$— O(C$_1$-C$_4$)alkylene-CO$_2$R$^w$, —O(C$_2$-C$_6$)alkylene-N (CH$_3$)$_2$, —O(C$_1$-C$_6$)haloalkyl, —NHC(=NH)NHR$^x$, —(C$_1$-C$_6$)haloalkyl and heteroalkyl;

According to other embodiments of the invention, one or more R$^1$ groups are independently selected from the group consisting of, —(C$_1$-C$_8$)hydrocarbyl other than —(C$_1$-C$_6$) alkyl, —NR$^w$$_2$, —NHC(=O)R$^y$, —N(R$^w$)CH(R$^z$)C(=O)R$^y$, —NHSO$_2$R$^y$, —NH(C$_1$-C$_4$)alkylene-CO$_2$R$^w$, —CN, —OCH(R$^z$)C(=O)R$^y$, —O(C$^1$-C$_6$)haloalkyl, —O(C$_2$-C$_6$)alkylene-N(CH$_3$)$_2$, —NHC(=NH)NHR$^x$, —(C$_1$-C$_6$)haloalkyl and heteroalkyl.

According to still other embodiments of the invention, one or more R$^1$ groups are independently selected from the group consisting of fluoro, chloro, —(C$_1$-C$_8$)hydrocarbyl, —NR$^w$$_2$, —NHC(=O)R$^y$, —NHCH(R$^z$)C(=O)R$^Y$, —NH(C$_1$-C$_4$) alkylene-CO$_2$R$^w$, —CN, —OCH(R$^z$)C(=O)R$^y$, —O(C$_1$-C$_6$) haloalkyl, —O(C$_2$-C$_6$)alkylene-N(CH$_3$)$_2$, and —(C$_1$-C$_6$)haloalkyl.

According to still other embodiments of the invention, one or more R$^1$ groups are independently selected from the group consisting of fluoro, chloro, —(C$_1$-C$_6$)alkyl, —NHR$^x$, —NHC(=O)R$^y$, —NHSO$_2$R$^y$, —CN, and —(C$_1$-C$_6$)haloalkyl.

According to some embodiments, R$^y$ is selected from the group consisting of —(C$_1$-C$_8$)hydrocarbyl, —O(C$_1$-C$_8$)hydrocarbyl, substituted phenyl, substituted heterocyclyl(C$_1$-C$_3$)alkyl, heteroaryl(C$_1$-C$_3$)alkyl, —(C$_2$-C$_{10}$)heteroalkyl, —(C$_1$-C$_6$)haloalkyl, —C(R$^z$)NHR$^x$, —N(R$^w$)R$^x$, —(C$_1$-C$_3$) alkyleneNH$_2$, —(C$_1$-C$_3$)alkyleneN(CH$_3$)$_2$, —(C$_1$-C$_3$)perfluoroalkyleneN(CH$_3$)$_2$, —(C$_1$-C$_3$)alkylene-OR$_x$, —(C$_1$-C$_4$) alkylene-CO$_2$R$^w$, —(C$_1$-C$_4$)alkylene-CO$_2$N(R$^w$)R$^x$, halo (C$_1$-C$_3$)alkyl and —(C$_1$-C$_4$)perfluoroalkylene-CO$_2$R$^w$.

According to other embodiments, R$^y$ is selected from the group consisting of —(C$_2$-C$_8$)hydrocarbyl, —O(C$_1$-C$_8$)hydrocarbyl, substituted phenyl, substituted heterocyclyl(C$_1$-C$_3$)alkyl, heteroaryl(C$_1$-C$_3$)alkyl, —(C$_2$-C$_{10}$)heteroalkyl, —(C$_1$-C$_6$)haloalkyl, —C(R$^z$)NHR$^x$, —N(R$^w$)R$^x$, —(C$_1$-C$_3$) alkyleneNH$_2$, —(C$_1$-C$_3$)alkyleneN(CH$_3$)$_2$, —(C$_1$-C$_3$)perfluoroalkyleneN(CH$_3$)$_2$, —(C$_1$-C$_3$)alkylene-OR$^x$, —(C$_1$-C$_4$) alkylene-CO$_2$R$^w$, —(C$_1$-C$_4$)alkylene-CO$_2$N(R$^w$)R$^x$, halo (C$_1$-C$_3$)alkyl and —(C$_1$-C$_4$)perfluoroalkylene-CO$_2$R$^w$.

According to other embodiments, R$^y$ is selected from the group consisting of —(C$_2$-C$_6$)alkyl, —O(C$_1$-C$_6$)alkyl, substituted phenyl, substituted heterocyclyl(C$_1$-C$_3$)alkyl, heteroaryl(C$_1$-C$_3$)alkyl, —(C$_2$-C$_6$)heteroalkyl, —(C$_1$-C$_6$)haloalkyl, —C(R$^z$)NHR$^x$, —NHR$^x$, —(C$_1$-C$_3$)alkyleneNH$_2$, —(C$_1$-C$_3$)alkyleneN(CH$_3$)$_2$, —(C$_1$-C$_3$)perfluoroalkyleneN (CH$_3$)$_2$, —(C$_1$-C$_3$)alkylene-OR$_x$, —(C$_1$-C$_4$)alkylene-CO$_2$R$^w$, —(C$_1$-C$_4$)alkylene-CO$_2$NHR$^x$, halo(C$_1$-C$_3$)alkyl and —(C$_1$-C$_4$)perfluoroalkylene-CO$_2$R$^w$.

According to still other embodiments, R$^y$ is selected from the group consisting of —(C$_2$-C$_6$)alkyl, —O(C$_1$-C$_6$)alkyl, substituted phenyl, substituted heterocyclyl(C$_1$-C$_3$)alkyl, heteroaryl(C$_1$-C$_3$)alkyl, —(C$_1$-C$_6$)haloalkyl, —C(R$^z$)NHR$^x$, —NHR$^x$, —(C$_1$-C$_3$)alkyleneNH$_2$, —(C$_1$-C$_3$)alkyleneN(CH$_3$)$_2$, —(C$_1$-C$_3$)alkylene-OR$^x$, —(C$_1$-C$_4$)alkylene-CO$_2$R$^w$, —(C$_1$-C$_4$)alkylene-CO$_2$NHR$^x$ and halo(C$_1$-C$_3$)alkyl.

A. Compounds According to Formula IA

According to one embodiment of the compounds according to Formula I, novel compounds are provided according to Formula IA:

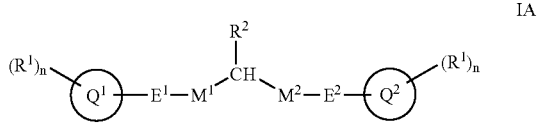

wherein R$^1$, R$^2$, R$^x$, R$^y$, R$^z$, M$^1$, M$^2$, E$^1$, E$^2$, Q$^1$, Q$^2$ and n are as defined above for Formula I.

According to a first embodiment of the compounds according to Formula IA, M$^1$ is —SO$_2$— and M$^2$ is —SO$_2$— or —C(=O)—.

Preferred compounds according to the first embodiment of the compounds according to Formula IA include:

4-((1E)-2-(((E)-2-fluoro-4-cyanostyrylsulfonyl)methylsulfonyl)vinyl)-3-fluoro-benzonitrile; 4-((1Z)-2-(((E)-2-fluoro-4-cyanostyrylsulfonyl)methylsulfonyl)vinyl)-3-fluoro-benzonitrile; (3E)-1-(2-fluoro-4-cyano-(E)-styrylsulfonyl)-4-(2-fluoro-4-cyanophenyl)but-3-en-2-one; (3Z)-1-(2-fluoro-4-cyano-(E)-styrylsulfonyl)-4-(2-fluoro-4-cyanophenyl)but-3-en-2-one; (3E)-1-(2-fluoro-4-cyano-(Z)-styrylsulfonyl)-4-(2-fluoro-4-cyanophenyl)but-3-en-2-one; bis((E)-2,4-difluorostyrylsulfonyl)methane; 1-((1Z)-2-(((E)-2,4-difluorostyrylsulfonyl)methylsulfonyl)vinyl)-2,4-difluorobenzene; (3E)-1-(2,4-difluoro-(E)-styrylsulfonyl)-4-(2,4-difluorophenyl)but-3-en-2-one; (3Z)-1-(2,4-difluoro-(E)-styryl-sulfonyl)-4-(2,4-difluorophenyl)but-3-en-2-one; (3E)-1-(2,4-difluoro-(Z)-styryl-sulfonyl)-4-(2,4-difluorophenyl)but-3-en-2-one; bis((E)-4-chlorostyrylsulfonyl)methane; 1-((1Z)-2-(((E)-4-chlorostyrylsulfonyl)methylsulfonyl)vinyl)-4-chlorobenzene; (3E)-1-(4-chloro-(E)-styrylsulfonyl)-4-(4-chlorophenyl)but-3-en-2-one; (3Z)-1-(4-chloro-(E)-styryl-sulfonyl)-4-(4-chlorophenyl)but-3-en-2-one; (3E)-1-(4-chloro-(Z)-styrylsulfonyl)-4-(4-chlorophenyl)but-3-en-2-one; bis((E)4-fluorostyrylsulfonyl)methane; 1-((1Z)-2-(((E)-4-fluoro-styrylsulfonyl)methylsulfonyl)vinyl)-4-fluorobenzene; (3E)-1-(4-fluoro-(E)-styryl-sulfonyl)-4-(4-fluorophenyl)but-3-en-2-one; (3Z)-1-(4-fluoro-(E)-styrylsulfonyl)-4-(4-fluorophenyl)but-3-en-2-one; (3E)-1-(4-fluoro-(Z)-styrylsulfonyl)-4-(4-fluorophenyl)but-3-en-2-one; bis((E)-2-(thiophen-3-yl)vinylsulfonyl)methane; 3-((1E)-2-(((Z)-2-(thiophen-3-yl)vinylsulfonyl)methylsulfonyl)vinyl)thiophene; (3E)-1-((E)-2-(thiophen-3-yl)vinyl-sulfonyl)-4-(thiophen-3-yl)but-3-en-2-one; (3E)-1-((Z)-2-(thiophen-3-yl)vinylsulfonyl)-4-(thiophen-3-yl)but-3-en-2-one; (3Z)-1-((E)-2-(thiophen-3-yl)vinylsulfonyl)-4-(thiophen-3-yl)but-3-en-2-one; bis((E)-perfluorostyrylsulfonyl)methane; 1-((1Z)-2-(((E)-perfluorostyrylsulfonyl)methylsulfonyl)vinyl)-2,3,4,5,6-pentafluorobenzene; (3E)-4-((E)-perfluorophenyl)-1-(perfluorostyrylsulfonyl)but-3-en-2-one; (3Z)-4-((E)-perfluorophenyl)-1-(per-fluorostyrylsulfonyl)but-3-en-2-one; (3E)-4-((Z)-perfluorophenyl)-1-(perfluorostyrylsulfonyl)but-3-en-2-one; 5-((1E)-2-(((E)-3-amino-4-methoxystyrylsulfonyl)methylsulfonyl)vinyl)-2-methoxybenzenamine; 5-((1Z)-2-(((E)-3-amino-4-methoxystyrylsulfonyl)-methylsulfonyl)vinyl)-2-methoxybenzenamine; (3E)-1-((E)-3-amino-4-methoxystyrylsulfonyl)-4-(3-amino-4-methoxyphenyl)but-3-en-2-one; (3Z)-1-((E)-3-amino-4-methoxystyrylsulfonyl)-4-(3-amino-4-methoxyphenyl)but-3-en-2-one; (3E)-1-((Z)-3-amino-4-methoxystyrylsulfonyl)-4-(3-amino-4-methoxyphenyl)but-3-en-2-one; (3E)-1-((E)-4-methoxy-3-nitrostyrylsulfonyl)-4-(4-methoxy-3-nitrophenyl)but-3-en-2-one; (3Z)-1-((E)-4-methoxy-3-nitrostyrylsulfonyl)-4-(4-methoxy-3-nitrophenyl)but-3-en-2-one; (3E)-1-((Z)-4-methoxy-3-nitrostyrylsulfonyl)-4-(4-methoxy-3-nitrophenyl)but-3-en-2-one; (3E)-1-((E)-4-hydroxy-3-methoxystyrylsulfonyl)-4-(4-hydroxy-3-methoxyphenyl)-but-3-en-2-one; (3E)-1-((Z)-4-hydroxy-3-methoxystyrylsulfonyl)-4-(4-hydroxy-3-methoxyphenyl)-but-3-en-2-one; (3Z)-1-((E)-4-hydroxy-3-methoxystyrylsulfonyl)-4-(4-hydroxy-3-methoxyphenyl)but-3-en-2-one; (3E)-1-((E)-2,4,6-trimethoxystyrylsulfonyl)-4-(2,4,6-trimethoxyphenyl)but-3-en-2-one; (3E)-1-((Z)-2,4,6-trimethoxystyrylsulfonyl)-4-(2,4,6-trimethoxyphenyl)but-3-en-2-one; (3Z)-1-((E)-2,4,6-trimethoxystyrylsulfonyl)-4-(2,4,6-trimethoxyphenyl)but-3-en-2-one; (3E)-1-((E)-2,6-dimethoxystyrylsulfonyl)-4-(2,6-di-methoxyphenyl)but-3-en-2-one; (3E)-1-((Z)-2,6-dimethoxystyrylsulfonyl)-4-(2,6-tri-methoxyphenyl)but-3-en-2-one; (3Z)-1-((E)-2,6-dimethoxystyrylsulfonyl)-4-(2,6-di-methoxyphenyl)but-3-en-2-one; (3E)-1-((E)-4-bromostyrylsulfonyl)-4-(4-bromophenyl)-but-3-en-2-one; (3E)-1-((Z)-4-bromostyrylsulfonyl)-4-(4-bromophenyl)but-3-en-2-one; (3Z)-1-((E)-4-bromostyrylsulfonyl)-4-(4-bromophenyl)but-3-en-2-one; (3E)-4-phenyl-1-((E)-styrylsulfonyl)but-3-en-2-one; (3E)-4-phenyl-1-((Z)-styrylsulfonyl)but-3-en-2-one; (3Z)-4-phenyl-1-((E)-styrylsulfonyl)but-3-en-2-one; (3E)-1-((E)-3,4,5-trimethoxystyryl-sulfonyl)-4-(3,4,5-trimethoxyphenyl)but-3-en-2-one; (3E)-1-((Z)-3,4,5-trimethoxystyryl-sulfonyl)-4-(3,4,5-trimethoxyphenyl)but-3-en-2-one; (3Z)-1-((E)-3,4,5-trimethoxystyryl-sulfonyl)-4-(3,4,5-trimethoxyphenyl)but-3-en-2-one; (3E)-1-((E)-4-hydroxy-2,6-di-methoxystyrylsulfonyl)-4-(4-hydroxy-2,6-dimethoxyphenyl)but-3-en-2-one; (3E)-1-((Z)-4-hydroxy-2,6-dimethoxystyrylsulfonyl)-4-(4-hydroxy-2,6-dimethoxyphenyl)but-3-en-2-one; (3Z)-1-((E)-4-hydroxy-2,6-dimethoxystyrylsulfonyl)-4-(4-hydroxy-2,6-dimethoxyphenyl)but-3-en-2-one; (3E)-1-((E)-4-iodostyrylsulfonyl)-4-(4-iodophenyl)but-3-en-2-one; (3E)-1-((Z)-4-iodostyrylsulfonyl)-4-(4-iodophenyl)but-3-en-2-one; (3Z)-1-((E)-4-iodostyrylsulfonyl)-4-(4-iodophenyl)but-3-en-2-one; (3E)-1-((E)-3-hydroxy-4-methoxystyrylsulfonyl)-4-(3-hydroxy-4-methoxyphenyl)-but-3-en-2-one; (3E)-1-((Z)-3-hydroxy-4-methoxystyrylsulfonyl)-4-(3-hydroxy-4-methoxyphenyl)but-3-en-2-one; (3Z)-1-((E)-3-hydroxy-4-methoxystyrylsulfonyl)-4-(3-hydroxy-4-methoxyphenyl)but-3-en-2-one; mixtures thereof; and salts thereof.

According to a second embodiment of the compounds according to Formula IA, M$^1$ is —S(=O)— and M$^2$ is —S(=O)— or —C(=O)—.

Preferred compounds according to the second embodiment of the compounds according to Formula IA include:

4-((1E)-2-(((E)-2-fluoro-4-cyanostyrylsulfinyl)methylsulfinyl)vinyl)-3-fluoro-benzonitrile; 4-((1Z)-2-(((E)-2-fluoro-4-cyanostyrylsulfinyl)methylsulfinyl)vinyl)-3-fluorobenzonitrile; (3E)-1-(2-fluoro-4-cyano-(E)-styrylsulfinyl)-4-(2-fluoro-4-cyanophenyl)but-3-en-2-one; (3Z)-1-(2-fluoro-4-cyano-(E)-styrylsulfinyl)-4-(2-fluoro-4-cyanophenyl)but-3-en-2-one; (3E)-1-(2-fluoro-4-cyano-(Z)-styrylsulfinyl)-4-(2-fluoro-4-cyanophenyl)but-3-en-2-one; bis((E)-2,4-difluorostyrylsulfinyl)methane; 1-((1Z)-2-(((E)-

2,4-difluorostyrylsulfinyl)methylsulfinyl)vinyl)-2,4-difluorobenzene; (3E)-1-(2,4-difluoro-(E)-styrylsulfinyl)-4-(2,4-difluorophenyl)but-3-en-2-one; (3Z)-1-(2,4-difluoro-(E)-styryl-sulfinyl)-4-(2,4-difluorophenyl)but-3-en-2-one; (3E)-1-(2,4-difluoro-(Z)-styryl-sulfinyl)-4-(2,4-difluorophenyl)but-3-en-2-one; bis((E)-4-chlorostyrylsulfinyl)methane; 1-((1Z)-2-(((E)-4-chlorostyrylsulfinyl)methylsulfinyl)vinyl)-4-chlorobenzene; (3E)-1-(4-chloro-(E)-styrylsulfinyl)-4-(4-chlorophenyl)but-3-en-2-one; (3Z)-1-(4-chloro-(E)-styryl-sulfinyl)-4-(4-chlorophenyl)but-3-en-2-one; (3E)-1-(4-chloro-(Z)-styrylsulfinyl)-4-(4-chlorophenyl)-but-3-en-2-one; bis((E)4-fluorostyrylsulfinyl)methane; 1-((1Z)-2-(((E)-4-fluorostyryl-sulfinyl)methylsulfinyl)vinyl)-4-fluorobenzene; (3E)-1-(4-fluoro-(E)-styryl-sulfinyl)-4-(4-fluorophenyl)but-3-en-2-one; (3Z)-1-(4-fluoro-(E)-styrylsulfinyl)-4-(4-fluorophenyl)but-3-en-2-one; (3E)-1-(4-fluoro-(Z)-styrylsulfinyl)-4-(4-fluorophenyl)but-3-en-2-one; bis-((E)-2-(thiophen-3-yl)vinylsulfinyl)methane; 3-((1E)-2-(((Z)-2-(thiophen-3-yl)vinylsulfinyl)methylsulfinyl)vinyl) thiophene; (3E)-1-((E)-2-(thiophen-3-yl)vinyl-sulfinyl)-4-(thiophen-3-yl)but-3-en-2-one; (3E)-1-((Z)-2-(thiophen-3-yl)vinylsulfinyl)-4-(thiophen-3-but-3-en-2-one; (3Z)-1-((E)-2-(thiophen-3-yl)vinylsulfinyl)-4-(thiophen-3-yl)but-3-en-2-one; bis((E)-perfluorostyrylsulfinyl)methane; 1-((1Z)-2-(((E)-perfluorostyrylsulfinyl)-methylsulfinyl)vinyl)-2,3,4,5,6-pentafluorobenzene; (3E)-4-((E)-perfluorophenyl)-1-(perfluorostyrylsulfinyl)but-3-en-2-one; (3Z)-4-((E)-perfluorophenyl)-1-(perfluorostyrylsulfinyl)but-3-en-2-one; (3E)-4-((Z)-perfluorophenyl)-1-(perfluorostyrylsulfinyl)but-3-en-2-one; 5-((1E)-2-(((E)-3-amino-4-methoxystyrylsulfinyl)methylsulfinyl)vinyl)-2-methoxybenzenamine; 5-((1Z)-2-(((E)-3-amino-4-methoxystyrylsulfinyl)methylsulfinyl)vinyl)-2-methoxybenzenamine; (3E)-1-((E)-3-amino-4-methoxystyrylsulfinyl)-4-(3-amino-4-methoxyphenyl)but-3-en-2-one; (3Z)-1-((E)-3-amino-4-methoxystyrylsulfinyl)-4-(3-amino-4-methoxyphenyl)but-3-en-2-one; (3E)-1-((Z)-3-amino-4-methoxystyrylsulfinyl)-4-(3-amino-4-methoxyphenyl)but-3-en-2-one; bis((E)-4-methoxy-3-nitrostyrylsulfinyl)-methane; 4-((1Z)-2-(((E)-4-methoxy-3-nitrostyrylsulfinyl)methylsulfinyl)vinyl)-1-methoxy-2-nitrobenzene; (3E)-1-((E)-4-methoxy-3-nitrostyrylsulfinyl)-4-(4-methoxy-3-nitrophenyl)but-3-en-2-one; (3Z)-1-((E)-4-methoxy-3-nitrostyrylsulfinyl)-4-(4-methoxy-3-nitrophenyl)but-3-en-2-one; (3E)-1-((Z)-4-methoxy-3-nitrostyrylsulfinyl)-4-(4-methoxy-3-nitrophenyl)but-3-en-2-one; 4-((1E)-2-((4-hydroxy-3-methoxy-(E)-styrylsulfinyl)methyl-sulfinyl)vinyl)-2-methoxyphenol; 4-((1E)-2-((4-hydroxy-3-methoxy-(Z)-styrylsulfinyl)-methylsulfinyl)vinyl)-2-methoxyphenol; (3E)-1-((E)-4-hydroxy-3-methoxystyrylsulfinyl)-4-(4-hydroxy-3-methoxyphenyl)-but-3-en-2-one; (3E)-1-((Z)-4-hydroxy-3-methoxystyryl-sulfinyl)-4-(4-hydroxy-3-methoxyphenyl)but-3-en-2-one; (3Z)-1-((E)-4-hydroxy-3-methoxystyrylsulfinyl)-4-(4-hydroxy-3-methoxyphenyl)but-3-en-2-one; bis((E)-2,4,6-tri-methoxystyrylsulfinyl)methane; 2-((1E)-2-(((Z)-2,4,6-trimethoxystyrylsulfinyl)methyl-sulfinyl)vinyl)-1,3,5-trimethoxybenzene; (3E)-1-((E)-2,4,6-trimethoxystyrylsulfinyl)-4-(2,4,6-trimethoxyphenyl)but-3-en-2-one; (3E)-1-((Z)-2,4,6-trimethoxystyrylsulfinyl)-4-(2,4,6-trimethoxyphenyl)but-3-en-2-one; (3Z)-1-((E)-2,4,6-trimethoxystyrylsulfinyl)-4-(2,4,6-trimethoxyphenyl)but-3-en-2-one; bis((E)-2,6-dimethoxystyrylsulfinyl)methane; 2-((1E)-2-(((Z)-2,6-dimethoxystyrylsulfinyl)methylsulfinyl)vinyl)-1,3-diimethoxybenzene; (3E)-1-((E)-2,6-dimethoxystyrylsulfinyl)-4-(2,6-dimethoxyphenyl)but-3-en-2-one; (3E)-1-((Z)-2,6-dimethoxystyrylsulfinyl)-4-(2,6-trimethoxyphenyl)but-3-en-2-one; (3Z)-1-((E)-2,6-dimethoxystyrylsulfinyl)-4-(2,6-dimethoxyphenyl)but-3-en-2-one; bis((E)-4-bromo-styrylsulfinyl)methane; 1-((1Z)-2-(((E)-4-bromostyrylsulfinyl)methylsulfinyl)vinyl)-4-bromobenzene; (3E)-1-((E)-4-bromostyrylsulfinyl)-4-(4-bromophenyl)but-3-en-2-one; (3E)-1-((Z)-4-bromostyrylsulfinyl)-4-(4-bromophenyl)but-3-en-2-one; (3Z)-1-((E)-4-bromostyrylsulfinyl)-4-(4-bromophenyl)but-3-en-2-one; bis((E)-styrylsulfinyl)methane; 1-((1Z)-2-(((E)-styrylsulfinyl)methylsulfinyl)vinyl)benzene; (3E)-4-phenyl-1-((E)-styryl-sulfinyl)but-3-en-2-one; (3E)-4-phenyl-1-((Z)-styrylsulfinyl)but-3-en-2-one; (3Z)-4-phenyl-1-((E)-styrylsulfinyl)but-3-en-2-one; bis((E)-3,4,5-trimethoxystyrylsulfinyl)-methane; 5-((1Z)-2-(((E)-3,4,5-trimethoxystyrylsulfinyl)methylsulfinyl)vinyl)-1,2,3-trimethoxybenzene; (3E)-1-((E)-3,4,5-trimethoxystyrylsulfinyl)-4-(3,4,5-trimethoxyphenyl)-but-3-en-2-one; (3E)-1-((Z)-3,4,5-trimethoxystyrylsulfinyl)-4-(3,4,5-trimethoxyphenyl)-but-3-en-2-one; (3Z)-1-((E)-3,4,5-trimethoxystyrylsulfinyl)-4-(3,4,5-trimethoxyphenyl)-but-3-en-2-one; 4-((1E)-2-(((E)-4-hydroxy-2,6-dimethoxystyrylsulfinyl)methylsulfinyl)-vinyl)-3,5-dimethoxyphenol; 4-((1E)-2-(((E)-4-hydroxy-2,6-dimethoxystyrylsulfinyl)-methylsulfinyl)vinyl)-3,5-dimethoxyphenol; (3E)-1-((E)-4-hydroxy-2,6-dimethoxystyryl-sulfinyl)-4-(4-hydroxy-2,6-dimethoxyphenyl)but-3-en-2-one; (3E)-1-((Z)-4-hydroxy-2,6-dimethoxystyrylsulfinyl)-4-(4-hydroxy-2,6-dimethoxyphenyl)but-3-en-2-one; (3Z)-1-((E)-4-hydroxy-2,6-dimethoxystyrylsulfinyl)-4-(4-hydroxy-2,6-dimethoxyphenyl)but-3-en-2-one; bis((E)-4-iodostyrylsulfinyl)methane; 1-((1Z)-2-(((E)-4-iodostyrylsulfinyl)methyl-sulfinyl)vinyl)-4-iodobenzene; (3E)-1-((E)-4-iodostyrylsulfinyl)-4-(4-iodophenyl)but-3-en-2-one; (3E)-1-((Z)-4-iodostyrylsulfinyl)-4-(4-iodophenyl)but-3-en-2-one; (3Z)-1-((E)-4-iodostyrylsulfinyl)-4-(4-iodophenyl)but-3-en-2-one; 5-((1E)-2-(((E)-3-hydroxy-4-methoxystyrylsulfinyl)methylsulfinyl)vinyl)-2-methoxyphenol; 5-((1E)-2-(((Z)-3-hydroxy-4-methoxystyrylsulfinyl)methylsulfinyl)vinyl)-2-methoxyphenol; (3E)-1-((E)-3-hydroxy-4-methoxystyrylsulfinyl)-4-(3-hydroxy-4-methoxyphenyl)-but-3-en-2-one; (3E)-1-((Z)-3-hydroxy-4-methoxystyrylsulfinyl)-4-(3-hydroxy-4-methoxyphenyl)but-3-en-2-one; (3Z)-1-((E)-3-hydroxy-4-methoxystyrylsulfinyl)-4-(3-hydroxy-4-methoxyphenyl)but-3-en-2-one; mixtures thereof; and salts thereof.

B. Compounds According to Formula IB

According to a another embodiment of the compounds according to Formula I, novel compounds are provided according to Formula IB:

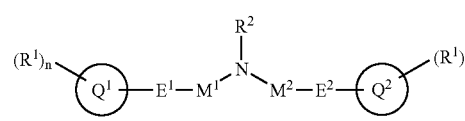

wherein $R^1$, $R^2$, $R^x$, $R^y$, $R^z$, $M^1$, $M^2$, $E^1$, $E^2$, $Q^1$, $Q^2$ and n are as defined above for Formula I.

According to a first embodiment of the compounds according to Formula IB, $M^1$ is —$SO_2$— and $M^2$ is selected from the group consisting of —$SO_2$— and —C(=O)—.

Preferred compounds according to the first embodiment of the compounds according to Formula IB include:

bis{[(1E)-2-(4-hydroxy-3-methoxyphenyl)vinyl]sulfonyl}amine; (2E)-N-{[(1E)-2-(4-hydroxy-3-methoxyphenyl)vinyl]sulfonyl}-3-(4-hydroxy-3-methoxyphenyl)prop-2-en-amide; {[(1E)-2-(4-hydroxy-3-methoxyphenyl)vinyl]sulfonyl}{[(1Z)-2-(4-hydroxy-3-methoxyphenyl)vinyl]}amine; (2E)-N-{[(1Z)-2-(4-hydroxy-3-methoxyphenyl)-vinyl]sulfonyl}-3-(4-hydroxy-3-methoxyphenyl)prop-2-enamide; N-{[(1E)-2-(4-hydroxy-3-methoxyphenyl)vinyl]sulfonyl}(2Z)-3-(4-hydroxy-3-methoxyphenyl)prop-2-enamide; bis {[(1E)-2-(3,4,5-trimethoxyphenyl)vinyl]sulfonyl}amine; (2E)-N-{[(1E)-2-(3,4,5-tri-methoxyphenyl)vinyl]sulfonyl}-3-(3,4,5-trimethoxyphenyl)prop-2-enamide; {[(1E)-2-(3,4,5-trimethoxyphenyl)vinyl]sulfonyl}{[(1Z)-2-(3,4,5-trimethoxyphenyl)vinyl]sulfonyl}amine; (2E)-N-{[(1Z)-2-(3,4,5-trimethoxyphenyl)vinyl]sulfonyl}-3-(3,4,5-trimethoxyphenyl)prop-2-enamide; N-{[(1E)-2-(3,4,5-trimethoxyphenyl)vinyl]sulfonyl}(2Z)-3-(3,4,5-trimethoxyphenyl)prop-2-enamide; bis {[(1E)-2-(2,3,4,5,6-pentafluorophenyl)-vinyl]sulfonyl}amine; (2E)-N-{[(1E)-2-(2,3,4,5,6-pentafluorophenyl)vinyl]sulfonyl}-3-(2,3,4,5,6-pentafluorophenyl)prop-2-enamide; {[(1E)-2-(2,3,4,5,6-pentafluorophenyl)-vinyl]sulfonyl}{[(1Z)-2-(2,3,4,5,6-pentafluorophenyl)vinyl]sulfonyl}amine; (2E)-N-{[(1Z)-2-(2,3,4,5,6-pentafluorophenyl)vinyl]sulfonyl}-3-(2,3,4,5,6-pentafluorophenyl)-prop-2-enamide; N-{[(1E)-2-(2,3,4,5,6-pentafluorophenyl)vinyl]sulfonyl}(2Z)-3-(2,3,4,5,6-pentafluorophenyl)prop-2-enamide; bis{[(1E)-2-(2,4,6-trimethoxyphenyl)-vinyl]sulfonyl}amine; (2E)-N-{[(1E)-2-(2,4,6-trimethoxyphenyl)vinyl]sulfonyl}-3-(2,4,6-trimethoxyphenyl)prop-2-enamide; {[(1E)-2-(2,4,6-trimethoxyphenyl)vinyl]sulfonyl}-{[(1Z)-2-(2,4,6-trimethoxyphenyl)vinyl]sulfonyl}amine; (2E)-N-{[(1Z)-2-(2,4,6-tri-methoxyphenyl)vinyl]sulfonyl}-3-(2,4,6-trimethoxyphenyl)prop-2-enamide; N-{[(1E)-2-(2,4,6-trimethoxyphenyl)vinyl]sulfonyl}(2Z)-3-(2,4,6-trimethoxyphenyl)prop-2-enamide; bis {[(1E)-2-(4-hydroxy-2,6-dimethoxyphenyl)vinyl]sulfonyl}amine; (2E)-N-{[(1E)-2-(4-hydroxy-2,6-dimethoxyphenyl)vinyl]sulfonyl}-3-(4-hydroxy-2,6-dimethoxyphenyl)prop-2-enamide; {[(1E)-2-(4-hydroxy-2,6-dimethoxyphenyl)vinyl]sulfonyl}{[(1Z)-2-(4-hydroxy-2,6-dimethoxyphenyl)vinyl]sulfonyl}amine; (2E)-N-{[(1Z)-2-(4-hydroxy-2,6-dimethoxyphenyl)vinyl]sulfonyl}-3-(4-hydroxy-2,6-dimethoxyphenyl)prop-2-enamide; N-{[(1E)-2-(4-hydroxy-2,6-dimethoxyphenyl)vinyl]sulfonyl}(2Z)-3-(4-hydroxy-2,6-di-methoxyphenyl)prop-2-enamide; bis{[(1E)-2-(2,6-dimethoxyphenyl)vinyl]sulfonyl}-amine; (2E)-N-{[(1E)-2-(2,6-dimethoxyphenyl)vinyl]sulfonyl}-3-(2,6-dimethoxyphenyl)-prop-2-enamide; {[(1E)-2-(2,6-dimethoxyphenyl)vinyl]sulfonyl}{[(1Z)-2-(2,6-dimethoxyphenyl)vinyl]sulfonyl}amine; (2E)-N-{[(1Z)-2-(2,6-dimethoxyphenyl)vinyl]sulfonyl}-3-(2,6-dimethoxyphenyl)prop-2-enamide; N-{[(1E)-2-(2,6-dimethoxyphenyl)vinyl]sulfonyl}(2Z)-3-(2,6-dimethoxyphenyl)prop-2-enamide; 4-{(1E)-2-[({[(1E)-2-(4-cyano-2-fluorophenyl)vinyl]sulfonyl}amino)sulfonyl]vinyl}-3-fluorobenzenecarbonitrile; (2E)-N-{[(1E)-2-(4-cyano-2-fluorophenyl)vinyl]sulfonyl}-3-(4-cyano-2-fluorophenyl)prop-2-enamide; 4-{(1E)-2-[({[(1Z)-2-(4-cyano-2-fluorophenyl)vinyl]sulfonyl}amino)sulfonyl]-vinyl}-3-fluorobenzenecarbonitrile; (2E)-N-{[(1Z)-2-(4-cyano-2-fluorophenyl)vinyl]-sulfonyl}-3-(4-cyano-2-fluorophenyl)prop-2-enamide; N-{[(1E)-2-(4-cyano-2-fluorophenyl)vinyl]sulfonyl}(2Z)-3-(4-cyano-2-fluorophenyl)prop-2-enamide; bis {[(1E)-2-(2,4-difluorophenyl)vinyl]sulfonyl}amine; (2E)-N-{[(1E)-2-(2,4-difluorophenyl)vinyl]-sulfonyl}-3-(2,4-difluorophenyl)prop-2-enamide; {[(1E)-2-(2,4-difluorophenyl)vinyl]-sulfonyl}{[(1Z)-2-(2,4-difluorophenyl)vinyl]sulfonyl}amine; (2E)-N-{[(1Z)-2-(2,4-di-fluorophenyl)vinyl]sulfonyl}-3-(2,4-difluorophenyl)prop-2-enamide; N-{[(1E)-2-(2,4-di-fluorophenyl)vinyl]sulfonyl}(2Z)-3-(2,4-difluorophenyl)prop-2-enamide; bis {[(1E)-2-(4-fluorophenyl)vinyl]sulfonyl}amine; (2E)-N-{[(1E)-2-(4-fluorophenyl)vinyl]sulfonyl}-3-(4-fluorophenyl)prop-2-enamide; {[(1E)-2-(4-fluorophenyl)vinyl]sulfonyl}{ [(1Z)-2-(4-fluorophenyl)vinyl]sulfonyl}amine; (2E)-N-{[(1Z)-2-(4-fluorophenyl)vinyl]sulfonyl}-3-(4-fluorophenyl)prop-2-enamide; N-{[(1E)-2-(4-fluorophenyl)vinyl]sulfonyl}(2Z)-3-(4-fluorophenyl)prop-2-enamide; bis {[(1E)-2-(4-chlorophenyl)vinyl]sulfonyl}amine; (2E)-N-{[(1E)-2-(4-chlorophenyl)vinyl]sulfonyl}-3-(4-chlorophenyl)prop-2-enamide; {[(1E)-2-(4-chlorophenyl)vinyl]sulfonyl}{[(1Z)-2-(4-chlorophenyl)vinyl]sulfonyl}amine; (2E)-N-{[(1Z)-2-(4-chlorophenyl)vinyl]sulfonyl}-3-(4-chlorophenyl)prop-2-enamide; N-{[(1E)-2-(4-chlorophenyl)vinyl]sulfonyl}(2Z)-3-(4-chlorophenyl)prop-2-enamide; bis{[(1E)-2-(4-bromophenyl)vinyl]sulfonyl}amine; (2E)-N-{[(1E)-2-(4-bromophenyl)vinyl]sulfonyl}-3-(4-bromophenyl)prop-2-enamide; {[(1E)-2-(4-bromophenyl)vinyl]sulfonyl}{[(1Z)-2-(4-bromophenyl)vinyl]sulfonyl}amine; (2E)-N-{[(1Z)-2-(4-bromophenyl)vinyl]sulfonyl}-3-(4-bromophenyl)prop-2-enamide; N-{[(1E)-2-(4-bromophenyl)vinyl]sulfonyl}(2Z)-3-(4-bromophenyl)prop-2-enamide; bis[((1E)-2-phenylvinyl)sulfonyl]amine; (2E)-N-[((1E)-2-phenylvinyl)sulfonyl]-3-phenylprop-2-enamide; [((1E)-2-phenylvinyl)sulfonyl][((1Z)-2-phenylvinyl)sulfonyl]amine; (2E)-N-[((1Z)-2-phenylvinyl)sulfonyl]-3-phenylprop-2-enamide; N-[((1E)-2-phenylvinyl)sulfonyl](2Z)-3-phenylprop-2-enamide; bis{[(1E)-2-(4-methoxy-3-nitrophenyl)vinyl]sulfonyl}amine; (2E)-N-{[(1E)-2-(4-methoxy-3-nitrophenyl)vinyl]sulfonyl}-3-(4-methoxy-3-nitrophenyl)prop-2-enamide; {[(1E)-2-(4-methoxy-3-nitrophenyl)vinyl]sulfonyl}{[(1Z)-2-(4-methoxy-3-nitrophenyl)vinyl]sulfonyl}amine; (2E)-N-{[(1Z)-2-(4-methoxy-3-nitrophenyl)vinyl]sulfonyl}-3-(4-methoxy-3-nitrophenyl)prop-2-enamide; N-{[(1E)-2-(4-methoxy-3-nitrophenyl)vinyl]sulfonyl}(2Z)-3-(4-methoxy-3-nitrophenyl)prop-2-enamide; bis[((1E)-2-(3-thienyl)vinyl)sulfonyl]amine; (2E)-N-[((1E)-2-(3-thienyl)vinyl)sulfonyl]-3-(3-thienyl)prop-2-enamide; [((1E)-2-(3-thienyl)vinyl)sulfonyl][((1Z)-2-(3-thienyl)vinyl)sulfonyl]amine; (2E)-N-[((1Z)-2-(3-thienyl)vinyl)sulfonyl]-3-(3-thienyl)prop-2-enamide; N-[((1E)-2-(3-thienyl)vinyl)sulfonyl](2Z)-3-(3-thienyl)prop-2-enamide; bis{[(1E)-2-(3-hydroxy-4-methoxyphenyl)vinyl]-sulfonyl}amine; (2E)-N-{[(1E)-2-(3-hydroxy-4-methoxyphenyl)vinyl]sulfonyl}-3-(3-hydroxy-4-methoxyphenyl)prop-2-enamide; {[(1E)-2-(3-hydroxy-4-methoxyphenyl)-vinyl]sulfonyl}{[(1Z)-2-(3-hydroxy-4-methoxyphenyl)vinyl]sulfonyl}amine; (2E)-N-{[(1Z)-2-(3-hydroxy-4-methoxyphenyl)vinyl]sulfonyl}-3-(3-hydroxy-4-methoxyphenyl)-prop-2-enamide; N-{[(1E)-2-(3-hydroxy-4-methoxyphenyl)vinyl]sulfonyl}(2Z)-3-(3-hydroxy-4-methoxyphenyl)prop-2-enamide; bis {[(1E)-2-(3-amino-4-methoxyphenyl)-vinyl]sulfonyl}amine; (2E)-N-{[(1E)-2-(3-amino-4-methoxyphenyl)vinyl]sulfonyl}-3-(3-amino-4-methoxyphenyl)prop-2-enamide; {[(1E)-2-(3-amino-4-methoxyphenyl)vinyl]-sulfonyl}{[(1Z)-2-(3-amino-4-methoxyphenyl)vinyl]sulfonyl}amine; (2E)-N-{[(1Z)-2-(3-amino-4-methoxyphenyl)vinyl]sulfonyl}-3-(3-amino-4-methoxyphenyl)prop-2-enamide; N-{[(1E)-2-(3-amino-4-methoxyphenyl)vinyl]sulfonyl}(2Z)-3-(3-amino-4-methoxyphenyl)prop-2-enamide; bis{[(1E)-2-(4- iodophenyl)vinyl]sulfonyl}amine; (2E)-N-{[(1E)-2-(4-iodophenyl)vinyl]sulfonyl}-3-(4-iodophenyl)prop-2-enamide; {[(1E)-2-(4-iodophenyl)vinyl]sulfonyl}{[(1Z)-2-(4-iodophenyl)vinyl]sulfonyl}amine; (2E)-N-{[(1Z)-2-(4-iodophenyl)vinyl]sulfonyl}-3-(4-iodophenyl)prop-2-enamide; N-{[(1E)-2-(4-iodophenyl)-vinyl]sulfonyl}(2Z)-3-(4-iodophenyl)prop-2-enamide; mixtures thereof; and salts thereof.

According to a second embodiment of compounds according to Formula IB, $M^1$ is —S(=O)— and $M^2$ is —S(=O)— or —C(=O)—.

Preferred compounds according to the second embodiment of compounds according to Formula IB include:

bis {[(1E)-2-(4-hydroxy-3-methoxyphenyl)vinyl]sulfinyl}amine; (2E)-N-{[(1E)-2-(4-hydroxy-3-methoxyphenyl)vinyl]sulfinyl}-3-(4-hydroxy-3-methoxyphenyl)prop-2-enamide; {[(1E)-2-(4-hydroxy-3-methoxyphenyl)vinyl]sulfinyl}{[(1Z)-2-(4-hydroxy-3-methoxyphenyl)vinyl]sulfinyl}amine; (2E)-N-{[(1Z)-2-(4-hydroxy-3-methoxyphenyl)-vinyl]sulfinyl}-3-(4-hydroxy-3-methoxyphenyl)prop-2-enamide; N-{[(1E)-2-(4-hydroxy-3-methoxyphenyl)vinyl]sulfinyl}(2Z)-3-(4-hydroxy-3-methoxyphenyl)prop-2-enamide; bis{[(1E)-2-(3,4,5-trimethoxyphenyl)vinyl]sulfinyl}amine; (2E)-N-{[(1E)-2-(3,4,5-tri-methoxyphenyl)vinyl]sulfinyl}-3-(3,4,5-trimethoxyphenyl)prop-2-enamide; {[(1E)-2-(3,4,5-trimethoxyphenyl)vinyl]sulfinyl}{[(1Z)-2-(3,4,5-trimethoxyphenyl)vinyl]sulfinyl}-amine; (2E)-N-{[(1Z)-2-(3,4,5-trimethoxyphenyl)vinyl]sulfinyl}-3-(3,4,5-trimethoxyphenyl)prop-2-enamide; N-{[(1E)-2-(3,4,5-trimethoxyphenyl)vinyl]sulfinyl}(2Z)-3-(3,4,5-trimethoxyphenyl)prop-2-enamide; bis{[(1E)-2-(2,3,4,5,6-pentafluorophenyl)vinyl]-sulfinyl}amine; (2E)-N-{[(1E)-2-(2,3,4,5,6-pentafluorophenyl)vinyl]sulfinyl}-3-(2,3,4,5,6-pentafluorophenyl)prop-2-enamide; {[(1E)-2-(2,3,4,5,6-pentafluorophenyl)-vinyl]sulfinyl}{[(1Z)-2-(2,3,4,5,6-pentafluorophenyl)vinyl]sulfinyl}amine; (2E)-N-{[(1Z)-2-(2,3,4,5,6-pentafluorophenyl)vinyl]sulfinyl}-3-(2,3,4,5,6-pentafluorophenyl)prop-2-enamide; N-{[(1E)-2-(2,3,4,5,6-pentafluorophenyl)vinyl]sulfinyl}(2Z)-3-(2,3,4,5,6-pentafluorophenyl)prop-2-enamide; bis{[(1E)-2-(2,4,6-trimethoxyphenyl)vinyl]sulfinyl}amine; (2E)-N-{[(1E)-2-(2,4,6-trimethoxyphenyl)vinyl]sulfinyl}-3-(2,4,6-trimethoxyphenyl)prop-2-enamide; {[(1E)-2-(2,4,6-trimethoxyphenyl)vinyl]sulfinyl}{[(1Z)-2-(2,4,6-trimethoxyphenyl)vinyl]sulfinyl}amine; (2E)-N-{[(1Z)-2-(2,4,6-trimethoxyphenyl)vinyl]sulfinyl}-3-(2,4,6-trimethoxyphenyl)prop-2-enamide; N-{[(1E)-2-(2,4,6-trimethoxyphenyl)vinyl]-sulfinyl}(2Z)-3-(2,4,6-trimethoxyphenyl)prop-2-enamide; bis{[(1E)-2-(4-hydroxy-2,6-dimethoxyphenyl)vinyl]sulfinyl}amine; (2E)-N-{[(1E)-2-(4-hydroxy-2,6-dimethoxyphenyl)vinyl]sulfinyl}-3-(4-hydroxy-2,6-dimethoxyphenyl)prop-2-enamide; {[(1E)-2-(4-hydroxy-2,6-dimethoxyphenyl)vinyl]sulfinyl}{[(1Z)-2-(4-hydroxy-2,6-dimethoxyphenyl)-vinyl]sulfinyl}amine; (2E)-N-{[(1Z)-2-(4-hydroxy-2,6-dimethoxyphenyl)vinyl]sulfinyl}-3-(4-hydroxy-2,6-dimethoxyphenyl)prop-2-enamide; N-{[(1E)-2-(4-hydroxy-2,6-di-methoxyphenyl)vinyl]sulfinyl}(2Z)-3-(4-hydroxy-2,6-dimethoxyphenyl)prop-2-enamide; bis{[(1E)-2-(2,6-dimethoxyphenyl)vinyl]sulfinyl}amine; (2E)-N-{[(1E)-2-(2,6-di-methoxyphenyl)vinyl]sulfinyl}-3-(2,6-dimethoxyphenyl)prop-2-enamide; {[(1E)-2-(2,6-dimethoxyphenyl)vinyl]sulfinyl}{[(1Z)-2-(2,6-dimethoxyphenyl)vinyl]sulfinyl}amine; (2E)-N-{[(1Z)-2-(2,6-dimethoxyphenyl)vinyl]sulfinyl}-3-(2,6-dimethoxyphenyl)prop-2-enamide; N-{[(1E)-2-(2,6-dimethoxyphenyl)vinyl]sulfinyl}(2Z)-3-(2,6-dimethoxyphenyl)-prop-2-enamide; 4-{(1E)-2-[({[(1E)-2-(4-cyano-2-fluorophenyl)vinyl]sulfinyl}amino)-sulfinyl]vinyl}-3-fluorobenzenecarbonitrile; (2E)-N-{[(1E)-2-(4-cyano-2-fluorophenyl)-vinyl]sulfinyl}-3-(4-cyano-2-fluorophenyl)prop-2-enamide; 4-{(1E)-2-[({[(1Z)-2-(4-cyano-2-fluorophenyl)vinyl]sulfinyl}amino)sulfinyl]vinyl}-3-fluorobenzenecarbonitrile; (2E)-N-{[(1Z)-2-(4-cyano-2-fluorophenyl)vinyl]sulfinyl}-3-(4-cyano-2-fluorophenyl)-prop-2-enamide; N-{[(1E)-2-(4-cyano-2-fluorophenyl)vinyl]sulfinyl}(2Z)-3-(4-cyano-2-fluorophenyl)prop-2-enamide; bis {[(1E)-2-(2,4-difluorophenyl)vinyl]sulfinyl}amine; (2E)-N-{[(1E)-2-(2,4-difluorophenyl)vinyl]sulfinyl}-3-(2,4-difluorophenyl)prop-2-enamide; {[(1E)-2-(2,4-difluorophenyl)vinyl]sulfinyl}{[(1Z)-2-(2,4-difluorophenyl)vinyl]-sulfinyl}amine; (2E)-N-{[(1Z)-2-(2,4-difluorophenyl)vinyl]sulfinyl}-3-(2,4-difluorophenyl)prop-2-enamide; N-{[(1E)-2-(2,4-difluorophenyl)vinyl]sulfinyl}(2Z)-3-(2,4-difluorophenyl)prop-2-enamide; bis {[(1E)-2-(4-fluorophenyl)vinyl]sulfinyl}amine; (2E)-N-{[(1E)-2-(4-fluorophenyl)vinyl]sulfinyl}-3-(4-fluorophenyl)prop-2-enamide; {[(1E)-2-(4-fluorophenyl)vinyl]sulfinyl}{[(1Z)-2-(4-fluorophenyl)vinyl]sulfinyl}amine; (2E)-N-{[(1Z)-2-(4-fluorophenyl)vinyl]sulfinyl}-3-(4-fluorophenyl)prop-2-enamide; N-{[(1E)-2-(4-fluorophenyl)vinyl]sulfinyl}(2Z)-3-(4-fluorophenyl)prop-2-enamide; bis {[(1E)-2-(4-chlorophenyl)vinyl]sulfinyl}amine; (2E)-N-{[(1E)-2-(4-chlorophenyl)vinyl]sulfinyl}-3-(4-chlorophenyl)prop-2-enamide; {[(1E)-2-(4-chlorophenyl)vinyl]sulfinyl} {[(1Z)-2-(4-chlorophenyl)vinyl]sulfinyl}amine; (2E)-N-{[(1Z)-2-(4-chlorophenyl)vinyl]sulfinyl}-chlorophenyl)prop-2-enamide; N-{[(1E)-2-(4-chlorophenyl)vinyl]sulfinyl}(2Z)-3-(4-chlorophenyl)prop-2-enamide; bis{[(1E)-2-(4-bromophenyl)vinyl]sulfinyl}amine; (2E)-N-{[(1E)-2-(4-bromophenyl)vinyl]sulfinyl}-3-(4-bromophenyl)prop-2-enamide; {[(1E)-2-(4-bromophenyl)vinyl]sulfinyl}{[(1Z)-2-(4-bromophenyl)vinyl]sulfinyl}amine; (2E)-N-{[(1Z)-2-(4-bromophenyl)vinyl]sulfinyl}-3-(4-bromophenyl)prop-2-enamide; N-{[1E)-2-(4-bromophenyl)vinyl]sulfinyl}(2Z)-3-(4-bromophenyl)prop-2-enamide; bis[((1E)-2-phenylvinyl)sulfinyl]amine; (2E)-N-[((1E)-2-phenylvinyl)sulfinyl]-3-phenylprop-2-enamide; [((1E)-2-phenylvinyl)sulfinyl][((1Z)-2-phenylvinyl)sulfinyl]amine; (2E)-N-[((1Z)-2-phenylvinyl)sulfinyl]-3-phenylprop-2-enamide; N-[((1E)-2-phenylvinyl)sulfinyl]-(2Z)-3-phenylprop-2-enamide; bis {[(1E)-2-(4-methoxy-3-nitrophenyl)vinyl]sulfinyl}-amine; (2E)-N-{[(1E)-2-(4-methoxy-3-nitrophenyl)vinyl]sulfinyl}-3-(4-methoxy-3-nitrophenyl)prop-2-enamide; {[(1E)-2-(4-methoxy-3-nitrophenyl)vinyl]sulfinyl}{[1Z)-2-(4-methoxy-3-nitrophenyl)vinyl]sulfinyl}amine; (2E)-N-{[(1Z)-2-(4-methoxy-3-nitrophenyl)vinyl]sulfinyl}-3-(4-methoxy-3-nitrophenyl)prop-2-enamide; N-{[(1E)-2-(4-methoxy-3-nitrophenyl)vinyl]sulfinyl}(2Z)-3-(4-methoxy-3-nitrophenyl)prop-2-enamide; bis[((1E)-2-(3-thienyl)vinyl]sulfinyl]amine; (2E)-N-[((1E)-2-(3-thienyl)vinyl)sulfinyl]-3-(3-thienyl)prop-2-enamide; [((1E)-2-(3-thienyl)vinyl)sulfinyl][((1Z)-2-(3-thienyl)vinyl)-sulfinyl]amine; (2E)-N-[((1Z)-2-(3-thienyl)vinyl)sulfinyl]-3-(3-thienyl)prop-2-enamide; N-[((1E)-2-(3-thienyl)vinyl)sulfinyl](2Z)-3-(3-thienyl)prop-2-enamide; bis{[(1E)-2-(3-hydroxy-4-methoxyphenyl)vinyl]sulfinyl}amine; (2E)-N-{[(1E)-2-(3-hydroxy-4-methoxyphenyl)vinyl]sulfinyl}-3-(3-hydroxy-4-methoxyphenyl)prop-2-enamide; {[(1E)-2-(3-hydroxy-4-methoxyphenyl)vinyl]sulfinyl}{[(1Z)-2-(3-hydroxy-4-methoxyphenyl)vinyl]-sulfinyl}amine; (2E)-N-{[(1Z)-2-(3-hydroxy-4-methoxyphenyl)vinyl]sulfonyl}-3-(3-hydroxy-4-methoxyphenyl)prop-2-enamide; N-{[(1E)-2-(3-hydroxy-4- methoxyphenyl)-vinyl]sulfinyl}(2Z)-3-(3-hydroxy-4-methoxyphenyl)prop-2-enamide; bis{[(1E)-2-(3-amino-4-methoxyphenyl)vinyl]sulfinyl}amine; (2E)-N-{ [(1E)-2-(3-amino-4-methoxyphenyl)vinyl]sulfinyl}-3-(3-amino-4-methoxyphenyl)prop-2-enamide; {[(1E)-2-(3-amino-4-methoxyphenyl)vinyl]sulfinyl}{[(1Z)-2-(3-amino-4-methoxyphenyl)vinyl]sulfinyl}-amine; (2E)-N-{[(1Z)-2-(3-amino-4-methoxyphenyl)vinyl]sulfinyl}-3-(3-amino-4-methoxyphenyl)prop-2-enamide; N-{[(1E)-2-(3-amino-4-methoxyphenyl)vinyl]sulfinyl}-(2Z)-3-(3-amino-4-methoxyphenyl)prop-2-enamide; bis{[(1E)-2-(4-iodophenyl)vinyl]-sulfinyl}amine; (2E)-N-{[(1E)-2-(4-iodophenyl)vinyl]sulfinyl}-3-(4-iodophenyl)prop-2-enamide; {[(1E)-2-(4-iodophenyl)vinyl]sulfinyl}{[(1Z)-2-(4-iodophenyl)vinyl]sulfinyl}-amine; (2E)-N-{[(1Z)-2-(4-iodophenyl)vinyl]sulfinyl}-3-(4-iodophenyl)prop-2-enamide; N-{[(1E)-2-(4-iodophenyl)vinyl]sulfinyl}(2Z)-3-(4-iodophenyl)prop-2-enamide; mixtures thereof; and salts thereof.

The present invention further embraces isolated compounds according to Formula I. The expression "isolated compound" refers to a preparation of a compound of Formula I, or a mixture of compounds according to Formula I, wherein the isolated compound contains the named compound or mixture of compounds according to Formula I in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

II. Intermediates in the preparation of Formula I Compounds

According to another embodiment of the invention, there are provided synthetic intermediates of Formula II:

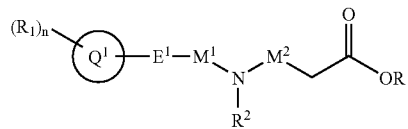

useful in the preparation of compounds according to Formula I wherein L in Formula I is N; and $R^1$, $R^2$ $Q^1$, $E^1$, $M^1$, $M^2$ and n are as defined above for Formula I, and R is —H or —(C$_1$-C$_8$)hydrocarbyl, preferably benzyl or —(C$_1$-C$_6$)alkyl, more preferably —(C$_1$-C$_3$)alkyl, most preferably methyl or ethyl.

Compounds according to Formula II, wherein $E^1$ is a carbon-carbon double bond having an (E)-configuration may be prepared, for example, by (a) reacting a compound according to Formula IIA:

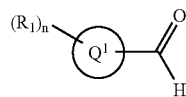

with a compound according to Formula IIB:

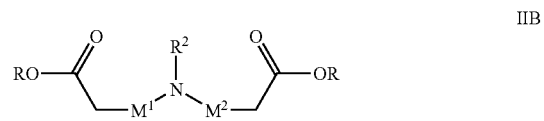

wherein $R^2$, $M^1$, and $M^2$ are as defined for Formula I, and R is —H or —(C$_1$-C$_7$)hydrocarbyl; and (b) isolating a compound according to Formula II from the reaction products.

Compounds according to Formula IIB wherein $M^1$ and $M^2$ are —SO$_2$— may be prepared, for example by (a) reacting a compound according to Formula IIC:

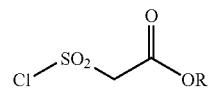

with a compound according to Formula IID:

(b) isolating a compound according to Formula IIB from the reaction products.

Compounds according to Formula IIB wherein one of $M^1$ and $M^2$ is —SO$_2$— and the other of $M^1$ and $M^2$ is —C(=O)— may be prepared, for example by (a) reacting a compound according to Formula IIC, as defined above, with a compound according to Formula IIE:

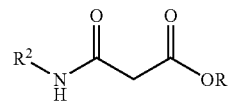

wherein $R^2$ is as defined herein for Formula I, and R is —(C$_1$-C$_8$)hydrocarbyl; and (b) isolating a compound according to Formula IIB from the reaction products.

Alternatively, compounds according to Formula IIB wherein one of $M^1$ and $M^2$ is —SO$_2$— and the other of $M^1$ and $M^2$ is —C(=O)— may be prepared, for example by (a) reacting a compound according to Formula IIF:

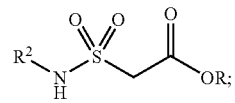

wherein $R^2$ is as defined for Formula I compounds and R is —H or —(C$_1$-C$_8$)hydrocarbyl, with an ester of a malonyl halide such as, for example methylmalonyl chloride (CAS [37517-81-0], Lancaster catalog number, 15131); and (b) isolating a compound according to Formula IIB from the reaction products.

Compounds according to Formula II, wherein $E^1$ is a carbon-carbon double bond having a (Z)-configuration, and $M^1$ is —SO$_2$—, may be prepared, for example, by (a) reacting a sulfonyl chloride compound according to Formula IIG:

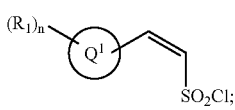

IIG wherein $R^1$, n and $Q^1$ are defined as for Formula II compounds, with a compound according to Formula IIH:

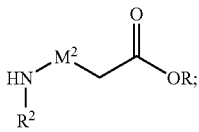

IIH wherein $R^2$ and $M^2$ are defined as for Formula II compounds; and (b) isolating a compound according to Formula II from the reaction products.

The sulfonyl chloride compound according to Formula IIG may be prepared, for example by:

(a) reacting a sulfonic acid compound according to Formula IIJ:

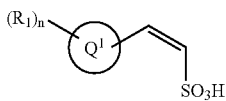

IIG wherein $R^1$, n and $Q^1$ are as defined for compounds of Formula IIG, with a halogenating agent such as, for example, thionyl chloride, phosphorous oxychloride or phosphorous pentachloride; and (b) isolating a compound according to Formula IIE from the reaction products.

The sulfonic acid compound according to Formula IIJ may be prepared, for example by (a) reacting a mercaptan compound according to Formula IIK:

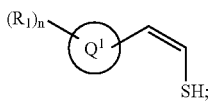

IIK wherein $R^1$, n and $Q^1$ are as defined for compounds of Formula IIJ with an oxidizing agent capable of oxidizing a mercaptan to a sulfonic acid; and (b) isolating from the reaction products a compound according to Formula IIJ:

The mercaptan compound according to Formula IIK may be prepared, for example by (a) reacting an aromatic acetylene compound according to Formula IIL:

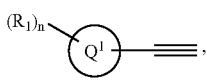

IIL wherein $R^1$, n and $Q^1$ are as defined herein for Formula I; with hydrogen sulfide or a suitable salt thereof such as, for example sodium sulfide; and (b) isolating a compound according to Formula IIK from the reaction products.

Alternatively, compounds according to Formula II, wherein $E^1$ is a carbon-carbon double bond having a (Z)-configuration, and $M^1$ is —$SO_2$—, may be prepared, for example, by (a) reacting a sulfonamide compound according to Formula IIM:

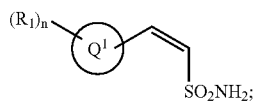

IIM wherein $R^1$, n and $Q^1$ are as defined for compounds of Formula II with a chlorosulfonyl acetate compound according to Formula IIC:

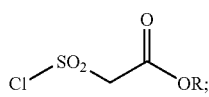

IIC wherein R is —H or —($C_1$-$C_8$)hydrocarbyl; and (b) isolating a compound according to Formula II from the reaction products.

A sulfonamide compound according to Formula IM may be prepared by (a) reacting a sulfonyl chloride compound according to Formula IIG with ammonia; and (b) isolating a compound of Formula IIM from the reaction products.

According to another embodiment of the invention, there are provided synthetic intermediates of Formula III:

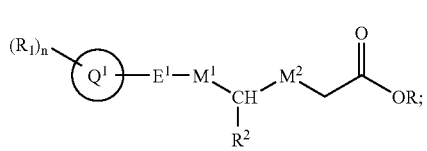

III useful in the preparation of compounds according to Formula I wherein L is CH; and $R^1$, $R^2$ $Q^1$, $E^1$, $M^1$, $M^2$ and n are as defined herein for Formula I, and R is —H or —($C_1$-$C_8$) hydrocarbyl, preferably benzyl or —($C_1$-$C_6$)alkyl, more preferably —($C_1$-$C_3$)alkyl, most preferably methyl or ethyl.

Compounds according to Formula III; wherein $E^1$ is a carbon-carbon double bond having an (E)-configuration may be prepared, for example, by (a) reacting a compound according to Formula IIA:

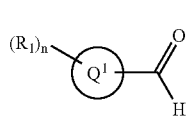

IIA wherein $R^1$, n and $Q^1$ are defined as for Formula III compounds, with a compound according to Formula IIIB:

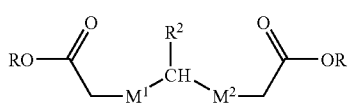

IIIB wherein R², M¹, and M² are as defined herein for Formula I, and R is —H or —(C₁-C₈)hydrocarbyl; and (b) isolating a compound according to Formula III from the reaction products.

Compounds according to Formula IIIB, wherein M¹ and M² are —SO— or —SO₂—, may be prepared, for example by:

(a) reacting a compound according to Formula IIIC:

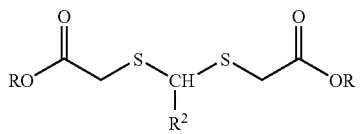

IIIC wherein R² is as defined herein for Formula I and R is —H or —(C₁-C₈)hydrocarbyl, with an oxidizing agent capable of selectively oxidizing a sulfide to either a sulfoxide or a sulfone respectively; and (b) isolating a compound according to Formula IIB, wherein M¹ and M² is —SO— or M¹ and M² is —SO₂—, respectively, from the reaction products.

Compounds according to Formula IIIC may be prepared, for example by (a) reacting mercaptoacetic acid, or a suitable ester thereof with a compound of Formula IIID:

IIID wherein R² is defined as for Formula IIIC compounds; and
(b) isolating a disulfide compound of Formula IIIC from the reaction products.

Compounds according to Formula III wherein one of M¹ and M² is —SO₂— or —SO— and the other of M¹ and M² is —C(=O)— may be prepared, for example by (a) reacting a compound of Formula IIIE:

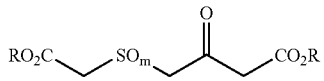

IIIE wherein m is 1 or 2 and R is as defined herein for Formula III; with a compound according to Formula IIA:

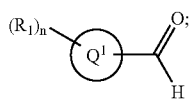

IIA wherein R¹, n and Q¹ are defined as for Formula III compounds and (b) isolating
(i) when m is 1, a compound according to Formula III wherein one of M¹ and M² is —SO— and the other of M¹ and M² is —C(=O)—; or
(ii) when m is 2, a compound according to Formula III wherein one of M¹ and M² is —SO₂— and the other of M¹ and M² is —C(=O)—.

The above reaction of a compound according to Formula IIIE with a compound according to Formula IIA may produce a product comprising a mixture of two isomeric compounds according to Formula III:

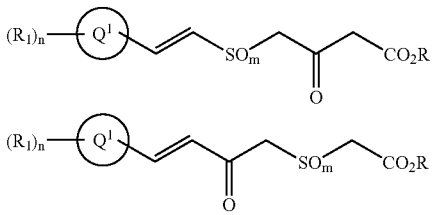

from which mixture either or both isomeric compounds according to Formula III may be isolated by a suitable separation such as, for example a chromatographic separation.

A compound according to Formula IIIE, wherein m is 1, may be prepared, for example by (a) reacting a compound of Formula IIIE, wherein m is zero, with an oxidizing agent capable of oxidizing a sulfide to a sulfoxide; and (b) isolating from the reaction products a compound according to Formula IIIE wherein m is 1.

A compound according to Formula IIIE, wherein m is 2 may be prepared, for example, by (a) reacting a compound of Formula IIIE, wherein m is zero, with an oxidizing agent capable of oxidizing a sulfide to a sulfone; and (b) isolating from the reaction products a compound according to Formula IIIE wherein m is 2.

A compound according to Formula IIIE, wherein m is zero, may be prepared, for example by (a) reacting mercaptoacetic acid, or a suitable ester thereof, with chloroacetoacetic acid (CAS [27807-84-7]), or a suitable ester thereof; and (b) isolating a compound according to Formula IIB from the reaction products.

Alternatively, compounds according to Formula III, wherein E¹ is a carbon-carbon double bond in the (E)-conformation, M¹ is —SO₂— and M² is —C(=O)—, may be prepared by:

(a) reacting a compound according to Formula IIIF:

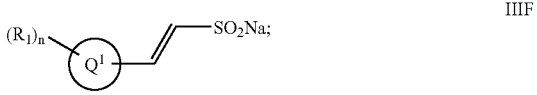

IIIF wherein R¹, n and Q¹ are defined as for Formula III compounds, with chloroacetoacetic acid or a suitable ester thereof; and (b) isolating a compound according to Formula III from the reaction products.

Compounds according to Formula III, wherein E¹ is a carbon-carbon double bond having a (Z)-configuration and M¹ is —S(=O)— or —SO₂— may be prepared, for example, by (a) reacting a compound according to Formula IIIJ:

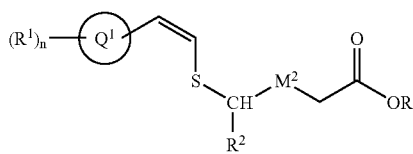

wherein $R^1$, $R^2$, n, $Q^1$, $M^2$ and R are defined as for Formula III compounds with (i) an oxidizing agent capable of oxidizing a sulfide to a sulfoxide or (ii) an oxidizing agent capable of oxidizing a sulfide to a sulfone; and (b) isolating from the reaction products a compound according to Formula III wherein $E^1$ is a carbon-carbon double bond having an (Z)-configuration and $M^1$ is —S(=O)— or —SO$_2$—, respectively.

Compounds according to Formula IIIJ may be prepared, for example, by:

(a) reacting a compound according to Formula IIIG:

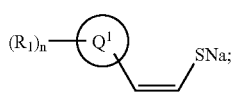

wherein $R^1$, n and $Q^1$ are as defined herein for Formula I; with a compound according to Formula IIIH:

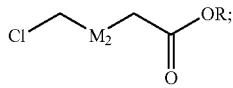

wherein $M^2$ and R are defined as for Formula III compounds and (b) isolating a compound according to Formula IIIJ from the reaction products.

Compounds according to Formula IIIG wherein $R^1$, n and $Q^1$ are as defined for compounds according to Formula I, may be prepared, for example by (a) reacting a compound of Formula IIL with sodium hydrogen sulfide, preferably in the presence of sodium hydroxide and preferably in the presence of a polar solvent such as, for example, methanol; and (b) isolating a compound according to Formula IIIG from the reaction products.

Compounds according to Formula IIIH wherein $M^2$ is —C(=O)— are known and include for example, chloroacetoacetate, CAS [638-07-3]. Compounds according to Formula IIIH wherein $M^2$ is —SO$_2$— may be prepared, for example, by reacting a suitable ester of mercaptoacetic acid, for example ethyl mercaptoacetate CAS [623-51-8], with excess formaldehyde or paraformaldehyde in the presence of an acid such as, for example, hydrochloric acid; and (b) isolating a compound according to Formula IIIH from the reaction products.

III. Processes of Preparing Compounds According to Formula I

According to another aspect of the invention, processes for preparing compounds according to Formula I are provided.

According to one embodiment of the invention, a compound according to Formula I:

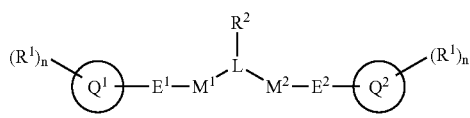

wherein $E^1$ and $E^2$ represent carbon-carbon double bonds having an (E)-configuration; $Q^1$ is identical to $Q^2$ and the $R^1$ substituents on $Q^1$ are identical to the $R^1$ substituents on $Q^2$, may be prepared by:

(a) reacting a compound according to Formula IIA:

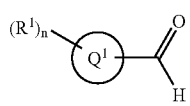

wherein $R^1$, n and $Q^1$ are defined as for Formula I compounds, with a compound of Formula IV:

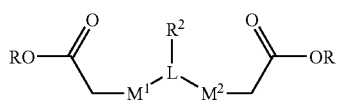

wherein $R^2$, $M^1$, $M^2$ and L are as defined herein for Formula I, and R is —H or —(C$_1$-C$_8$)hydrocarbyl, preferably benzyl or —(C$_1$-C$_6$)alkyl, more preferably —(C$_1$-C$_3$)alkyl, most preferably methyl or ethyl; and (b) isolating a compound according to Formula I from the reaction products.

According to another embodiment of the invention, a compound according to Formula I:

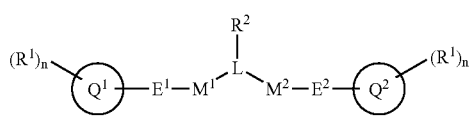

wherein $E^2$ represents carbon-carbon double bond having an (E)-configuration may be prepared by:

(a) reacting a compound according to Formula IVA:

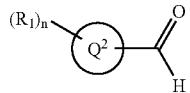

wherein $R^1$, n and $Q^2$ are defined as for Formula I compounds with a compound of Formula V:

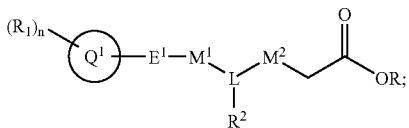

wherein $R^1$, n, $Q^1$, $M^1$, $M^2$, $R^2$ and L are as defined herein for Formula I, and R is —H or —($C_1$-$C_8$)hydrocarbyl, preferably benzyl or —($C_1$-$C_6$)alkyl, more preferably —($C_1$-$C_3$)alkyl, most preferably methyl or ethyl; and (b) isolating a compound according to Formula I from the reaction products.

According to another embodiment of the invention, a pharmaceutical composition is provided comprising a pharmaceutically acceptable carrier and one or more compounds according to Formula I.

IV. Methods of Treatment

According to another embodiment of the invention, a method of treating an individual suffering from a proliferative disorder, particularly cancer, is provided, comprising administering to said individual, either alone or in combination with a pharmaceutically acceptable carrier, an effective amount of at least one compound according to Formula IC:

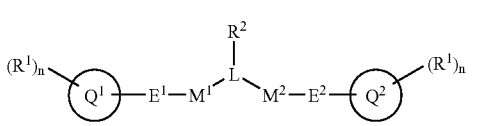

wherein:

$Q^1$ and $Q^2$ are independently selected from the group consisting of aryl and heteroaryl;

each $R^1$ is independently selected from the group consisting of halogen, —($C_1$-$C_8$)hydrocarbyl, —C(=O)$R^y$, —$NR^w_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —$NO_2$, —CN, —$OR^w$, —OC(=O)$R^y$, —OCH($R^z$)C(=O)$R^y$, —$OSO_2R^y$—O($C_1$-$C_4$)alkylene-$CO_2R^w$, —OP(=O)(O$R^w$)$_2$, —O($C_2$-$C_6$)alkylene-N($CH_3$)$_2$, —O($C_1$-$C_6$)haloalkyl, —P(=O)(O$R^w$)$_2$, —$SO_2$N($R^w$)$R^x$, —NHC(=NH)$NHR^x$, —($C_1$-$C_6$)haloalkyl and heteroalkyl;

each $R^w$ is independently —H or —($C_1$-$C_8$)hydrocarbyl;

each $R^x$ is independently —H, —($C_1$-$C_8$)hydrocarbyl or —C(=O)($C_1$-$C_8$)hydrocarbyl;

each $R^y$ is independently selected from the group consisting of —H, —($C_1$-$C_8$)hydrocarbyl, —O($C_1$-$C_8$)hydrocarbyl, substituted phenyl, substituted heterocyclyl($C_1$-$C_3$)alkyl, heteroaryl($C_1$-$C_3$)alkyl, —($C_2$-$C_{10}$)heteroalkyl, —($C_1$-$C_6$)haloalkyl, —C($R^z$)$NHR^x$, —N($R^w$)$R^x$, —($C_1$-$C_3$)alkyleneNH$_2$, —($C_1$-$C_3$)alkyleneN($CH_3$)$_2$, —($C_1$-$C_3$)perfluoroalkyleneN($CH_3$)$_2$, —($C_1$-$C_3$)alkyleneN$^+$(($C_1$-$C_3$)alkyl)$_3$, —($C_1$-$C_3$)alkylene-N$^+$($CH_2CH_2OH$)$_3$, —($C_1$-$C_3$)alkylene-$OR^x$, —($C_1$-$C_4$)alkylene-$CO_2R^w$, —($C_1$-$C_4$)alkylene-$CO_2$N($R^w$)$R^x$, —($C_1$-$C_4$)alkylene-C(=O)halogen, halo($C_1$-$C_3$)alkyl and —($C_1$-$C_4$)perfluoroalkylene-$CO_2R^w$;

each $R^z$ is independently selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2CO_2$H, —$CH_2$-(2-imidazolyl), —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl) and —$CH_2$-(4-hydroxyphenyl);

each n is independently 0, 1, 2, 3, 4 or 5; preferably 1, 2, 3, 4 or 5; more preferably 1, 2, 3 or 4; most preferably 1, 2 or 3;

$M^1$ and $M^2$ are independently —$SO_2$—, —S(=O)— or —C(=O)—;

L is CH or N;

$R^2$ is selected from the group consisting of —H and —($C_1$-$C_6$)alkyl, preferably —H and —($C_1$-$C_6$)alkyl, more preferably —H and —$CH_3$, most preferably —H; and $E^1$ and $E^2$ are independently selected from the group consisting of a carbon-carbon double bond in the (E)-configuration and a carbon-carbon double bond in the (Z)-configuration;

provided that:

(i) when one of $M^1$ and $M^2$ is —$SO_2$—, then the other of $M^1$ and $M^2$ is other than —S(=O)—;

(ii) when one of $M^1$ and $M^2$ is —C(=O)—, then the other of $M^1$ and $M^2$ is other than —C(=O)—; and (iii) when one of $E^1$ and $E^2$ is a carbon-carbon double bond in the (Z)-configuration; then the other of $E^1$ and $E^2$ is a carbon-carbon double bond in the (E)-configuration; or a salt, preferably a pharmaceutically-acceptable salt of such a compound.

According to another embodiment of the invention, a method of inhibiting growth of tumor cells in an individual suffering from a proliferative disorder, particularly cancer, is provided comprising administering to said individual an effective amount of at least one compound according to Formula IC, as defined above, alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to Formula IC, as defined above, alone or in combination with a pharmaceutically acceptable carrier.

According to another embodiment of the invention, a method of treating an individual suffering from an angiogenesis-mediated disorder, particularly an angiogenesis-mediated disorder mediated by VEGF or FLT-1 is provided, comprising administering to said individual, either alone or in combination with a pharmaceutically acceptable carrier, an effective amount of at least one compound according to Formula IC, as defined above, alone, or in combination with a pharmaceutically acceptable carrier.

According to another embodiment of the invention, a method of treating an individual suffering from age-related senile dementia is provided, comprising administering to said individual, either alone or in combination with a pharmaceutically acceptable carrier, an effective amount of at least one compound according to Formula IC, as defined above, alone, or in combination with a pharmaceutically acceptable carrier.

Preferred compounds according to Formula IC for use in the methods of treatment of proliferative disorders and angiogenesis-mediated disorders include, in addition to the preferred compounds according to Formulae IA and IB, the following compounds according to Formula IC:

bis((E)-4-methoxy-3-nitrostyrylsulfonyl)methane; 4-((1Z)-2-(((E)-4-methoxy-3-nitrostyrylsulfonyl)methylsulfonyl)vinyl)-1-methoxy-2-nitrobenzene; 4-((1E)-2-((4-hydroxy-3-methoxy-(E)-styrylsulfonyl)methylsulfonyl)vinyl)-2-methoxyphenol; 4-((1E)-2-((4-hydroxy-3-methoxy-(Z)-styrylsulfonyl)methylsulfonyl)vinyl)-2-methoxyphenol; bis((E)-2,4,6-trimethoxystyrylsulfonyl)methane; 2-((1E)-2-(((Z)-2,4,6-trimethoxystyryl-sulfonyl)methylsulfonyl)vinyl)-1,3,5-trimethoxybenzene; bis((E)-2,6-dimethoxystyryl-sulfonyl)methane; 2-((1E)-2-(((Z)-2,6- dimethoxystyrylsulfonyl)methylsulfonyl)vinyl)-1,3-dimethoxybenzene; bis((E)-4-bromostyrylsulfonyl)methane; 1-((1Z)-2-(((E)-4-bromo-styrylsulfonyl)methylsulfonyl)vinyl)-4-bromobenzene; bis((E)-4-iodostyrylsulfonyl)-methane; 1-((1Z)-2-(((E)-styrylsulfonyl)methylsulfonyl)vinyl)benzene; bis((E)-3,4,5-trimethoxystyrylsulfonyl)methane; 5-((1E)-2-(((Z)-3,4,5-trimethoxystyrylsulfonyl)methyl-sulfonyl)vinyl)-1,2,3-trimethoxybenzene; 4-((1E)-2-(((E)-4-hydroxy-2,6-dimethoxystyryl-sulfonyl)methylsulfonyl)vinyl)-3,5-dimethoxyphenol; 4-((1Z)-2-(((E)-4-hydroxy-2,6-dimethoxystyrylsulfonyl)methylsulfonyl)vinyl)-3,5-dimethoxyphenol; bis((E)-4-iodostyrylsulfonyl)methane; 1-((1Z)-2-(((E)-4-iodostyrylsulfonyl)methylsulfonyl)vinyl)-4-iodo-benzene; 5-((1E)-2-(((E)-3-hydroxy-4-methoxystyrylsulfonyl)methylsulfonyl)vinyl)-2-methoxyphenol; 5-((1E)-2-(((Z)-3-hydroxy-4-methoxystyrylsulfonyl)methylsulfonyl)-vinyl)-2-methoxyphenol; mixtures thereof; and salts thereof.

According to other embodiments of the invention, there is provided the use of at least one compound according to Formula I, or at least one compound according to Formula IC for preparation of a medicament for:

(a) treating a proliferative disorder in an individual afflicted with a proliferative disorder;

(b) inhibiting the growth of tumor cells in an individual afflicted with a proliferative disorder;

(c) inducing apoptosis of cancer cells in an individual afflicted with cancer;

(d) treating an angiogenesis mediated disorder by inhibiting angiogenesis; or (e) treating age related senile dementia.

DETAILED DESCRIPTION OF THE INVENTION

I. Treatment of Proliferative Disorders

According to the present invention, certain α,β-unsaturated sulfones, sulfoxides, sulfonimides, sulfinimides, acylsulfonamides and acylsulfinamides selectively kill various tumor cell types without killing normal cells. Without wishing to be bound by any theory, it is believed that the compounds affect the mitogen activated protein kinase (MAPK) signal transduction pathway, thereby affecting tumor cell growth and viability. This cell growth inhibition is believed to be associated with regulation of extracellular signal regulated kinases (ERKs) and c-Jun $NH_2$ terminal kinases (JNK) types of MAPK. The compounds according to the present invention are believed to activate the JNK pathway, either by interacting with JNK1 or by interacting with an upstream kinase that is a part of the JNK pathway.

A. Treatment of Cancer

The compounds according to the invention may be administered to individuals (mammals, including animals and humans) afflicted with a proliferative disorder such as cancer.

The compounds according to the invention have been shown to inhibit the proliferation of tumor cells by inducing cell death. The cell-killing activity of the compounds according to the invention is selective for tumor cells over normal cells.

Cell death is believed to result from the induction of apoptosis. The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Karposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma;

cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers including, for example, malignant melanoma, basal cell carcinoma, squamous cell carcinoma, Karposi's sarcoma, moles dysplastic nevi, lipoma, angioma, dermatofibroma, keloids, psoriasis; and adrenal gland cancers including, for example, neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

B. Treatment of Non-Cancer Proliferative Disorders

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's Disease of the bone, fibrocystic disease of the breast, uterine fibroids, Peyronie's disease, Dupuytren's disease, restenosis, benign proliferative breast disease, benign prostatic hyperplasia, X-linked lymphoproliferative disorder (Duncan disease), post-transplantation lymphoproliferative disorder (PTLD), macular degeneration, and retinopathies, such as diabetic retinopathies and proliferative vitreoretinopathy (PVR).

Other non-cancer proliferative disorders believed treatable by compounds according to the invention include the presence of pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time.

Treatment of tumor cells with the compounds according to the invention is believed to lead to inhibition of cell proliferation and induction of apoptotic cell death.

C. Treatment of Angiogenesis-Mediated Disorders

The compounds of the invention are also believed to be useful in the treatment of angiogenesis-mediated disorders. Without wishing to be bound by any theory, it is believed that the compounds inhibit the action of vascular endothelial growth factor (VEGF), thereby inhibiting angiogenesis. Also without wishing to be bound by any theory, it is believed that the compounds inhibit the action of FMS-like tyrosine kinase (vascular endothelial growth factor/vascular permeability factor receptor) (FLT-1), thereby inhibiting angiogenesis.

Vascular endothelial growth factor (VEGF) is a dimeric heparin-binding glycoprotein that is a potent endothelial cell-specific mitogen with increased expression during adult cutaneous wound healing. VEGF activity is mediated by two receptors, VEGFR-1 (FLT-1) and VEGFR-2 (Flk-1/KDR), which are expressed primarily in vascular endothelial cells. See, Colwell et al., *Plast. Reconstr. Surg.;* 2005; 115(1); pages 204-12, the entire disclosure of which is incorporated herein by reference. FLT-1 expression has been shown to be significantly increased in heart cells and skeletal myoblasts wherein angiogenesis has been enhanced by and to increase eightfold by transplantation of vascular endothelial growth factor transfected cells. This observation suggests that FLT-1 upregulation may mediate the angiogenic effect of the cell transplantation. See, Yao et al., *Ann. Thorac. Surg.* 2005; 79(6); pages 2056-63, the entire disclosure of which is incorporated herein by reference. In vivo, delivery of naked plasmids expressing FLT-1 intraceptors inhibits injury-induced upregulation of VEGF, leukocyte infiltration, and corneal neovascularization. See, Singh et al., *Invest. Ophthalmol. Vis. Sci.* 2005; 46(5); pages 1647-52, the entire disclosure of which is incorporated herein by reference.

Thus, a method for treating, inhibiting or delaying the onset of an angiogenesis-mediated disorder in a subject is provided comprising administering to a subject in need of such treatment an effective amount of a compound according to the present invention. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

D. Treatment of Age-Related Senile Dementia

The compounds of the invention may also be useful in the treatment of age-related senile dementia, including, for example, Alzheimer's Disease (AD) and presenile dementia.

Recent findings have shown a relationship between levels of vascular endothelial growth factor (VEGF) and severity of disease symptoms, both in patients with vascular dementia (VAD) and AD. See, Tarkowski et al., *Neurobiol Aging,* 2002, 23(2), page 237-43, the entire disclosure of which is incorporated herein by reference. The investigation of patterns of local release of VEGF and transforming growth factor-beta (TGF-beta) in a group of patients with AD and VAD suggests that vascular factors may have a role in the pathogenesis of AD as well as VAD.

II. Isomerism in Compounds of the Invention

A. Geometric Isomerism

Compounds according to Formula I, IA, IB and IC are characterized by isomerism resulting from the presence of two carbon-carbon double bonds. This isomerism is commonly referred to as cis-trans isomerism, but the more comprehensive naming convention employs (E)- and (Z)-designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127-138, the entire contents of which is incorporated herein by reference. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher-ranking groups are on opposite sides of the double bond, is designated E (for the German word "entgegen", which means "opposite"). Thus, if the four groups on a carbon-carbon double bond are ranked, A being the lowest rank and D being highest, A>B>C>D, the isomers would be named as in Scheme 4.

Scheme 4

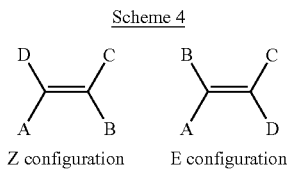

Z configuration  E configuration

Unless otherwise indicated, both configurations of the carbon-carbon double bonds are included in the scope of the compounds according to the invention, except that the double bonds represented by $M^1$ and $M^2$ in Formulae I, IA, IB and IC may not both be in the (Z)-configuration in the same compound.

B. Optical Isomerism

The present invention is also directed to isolated optical isomers of compounds according to Formulae I, IA, IB and IC. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. See March, Advanced Organic Chemistry, $4^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 7, the Cahn-Ingold-Pielog ranking is A>B>C>D. The lowest ranking atom, D is oriented away from the viewer.

Scheme 5

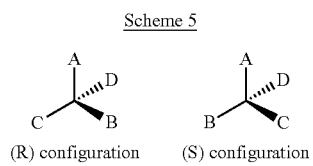

(R) configuration  (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

By "isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

III. Symmetry of Some Compounds According to the Invention

Some compounds according to Formulae I, IA, IB and IC are symmetric with respect to the aromatic groups $Q^1$ and $Q^2$ and the groups $R^1$ substituted thereon. Thus, some compounds of the invention are described by stating that $Q^1$ and $Q^2$ are identical and the $R^1$ substituents on $Q^1$ are identical to the $R^1$ substituents on $Q^2$. This description means that the substituents on $Q^1$ are the same groups and that the $R^1$ groups are in the same positions on $Q^1$ and $Q^2$.

Some compounds that are symmetric with respect to the aromatic groups $Q^1$ and $Q^2$ and the groups $R^1$ substituted thereon are further symmetric with respect to $M^1$ and $M^2$ and/or $E^1$ and $E^2$.

Some of the compounds of Formulae I, IA, IB and IC are not symmetric with respect to the aromatic groups $Q^1$ and $Q^2$ and the groups $R^1$ substituted thereon. Some compounds that are not symmetric with respect to the aromatic groups $Q^1$ and $Q^2$ and the groups $R^1$ substituted thereon are also not symmetric with respect to $M^1$ and $M^2$ and/or $E^1$ and $E^2$. In some instances, the synthesis of compounds of the invention that are not symmetric with respect to aromatic groups $Q^1$ and $Q^2$ and the groups $R^1$ substituted thereon, is non-selective. Such a non-selective synthesis may produce a mixture of symmetric and non-symmetric products from which the desired non-symmetric product must be isolated. The mixture of products resulting from such a non-selective synthesis of non-symmetric compounds of the invention includes may comprise compounds as shown in Scheme 6.

Scheme 6

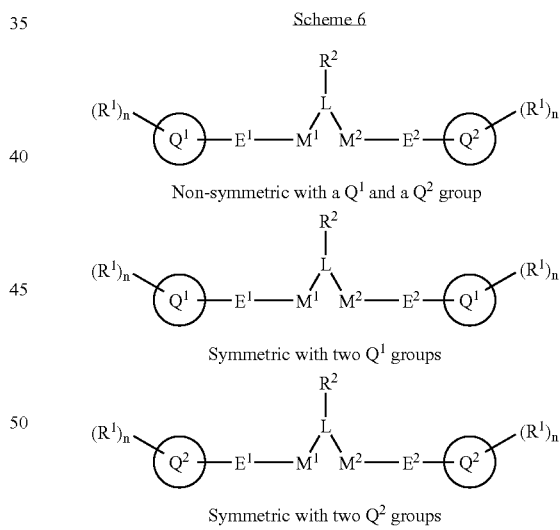

Non-symmetric with a $Q^1$ and a $Q^2$ group

Symmetric with two $Q^1$ groups

Symmetric with two $Q^2$ groups

IV. Preparation of Compounds According to the Invention

Compounds according to the invention may be prepared via synthetic organic chemistry methods as follows.

A. Preparation of Symmetric α,β-Unsaturated Sulfones and Sulfoxides of Formula I Compounds of Formula I wherein L is CH; $M^1$ and $M^2$ are both —$SO_2$— or are both —SO—; $E^1$ and $E^2$ are both carbon-carbon double bonds in the (E)-configuration; $Q^1$ is identical to $Q^2$ and the $R^1$ substituents on $Q^1$ are identical to the $R^1$ substituents on $Q^2$, may be prepared according to the methods depicted in Scheme 7 by reacting an aromatic aldehyde compound 4, with either compound 3a or compound 3b.

Scheme 7

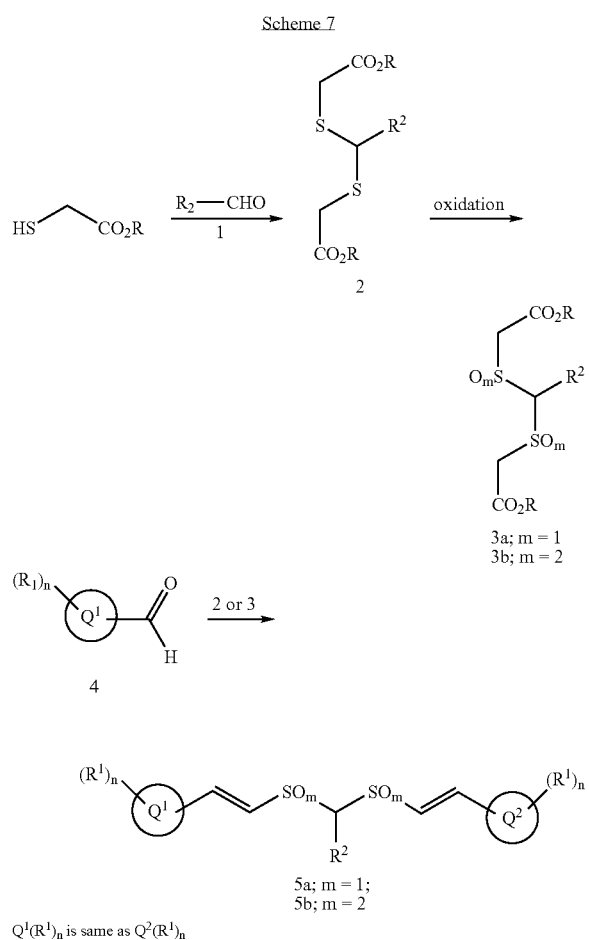

3a; m = 1
3b; m = 2

5a; m = 1;
5b; m = 2

$Q^1(R^1)_n$ is same as $Q^2(R^1)_n$ methylene disulfide 2 may be oxidized to the methylene disulfoxide 3a by reaction with a reagent capable of oxidizing a sulfide to a sulfoxide. Suitable oxidizing reagents for both oxidation reactions include peroxides such as hydrogen peroxide, peracids such as meta-chloroperoxybenzoic acid (MCPBA) or persulfates such as potassium peroxymonosulfate. The reaction is preferably carried out in the presence of a suitable solvent. Suitable solvents include, for example, water, acetic acid or non-polar solvents such as dichloromethane (DCM). Reaction to selectively form the methylene disulfoxide is preferably performed at low temperature, more preferably from about −10 to about 20° C. In addition, the reaction to form the methylene disulfoxide compound 3a is preferably monitored so as to terminate the reaction prior to appreciable oxidation to the sulfone. Reaction to form the methylene disulfone 3b may be performed at higher temperature, for example, from about 30 to about 100° C.

An aromatic aldehyde 4 may be reacted with compound 3b in glacial acetic acid in the presence of a catalytic amount of benzylamine to yield compound 6b, a compound according to Formula I wherein $M^1$ and $M^2$ are —$SO_2$—. The aromatic aldehyde 4 may be reacted with compound 3a in glacial acetic acid in the presence of a catalytic amount of benzylamine to yield compound 6a, a compound according to Formula I wherein $M^1$ and $M^2$ are —SO—.

B. Non-selective Preparation of Non-symmetric α, β-Unsaturated Sulfones and Sulfoxides of Formula I Compounds of Formula I wherein L is CH, $M^1$ and $M^2$ are both —$SO_2$— or are both —SO—, and $E^1$ and $E^2$ are both carbon-carbon double bonds in the (E)-configuration, but wherein $Q^1(R^1)_n$ and $Q^2(R^1)_n$ are different, may be prepared according to the methods depicted in Scheme 8 by reacting two different aromatic aldehyde compounds 4 and 6 with compound 3a to form methylene disulfoxide compound 7a, or with compound 3b to form methylene disulfone compound 7b.

Scheme 8

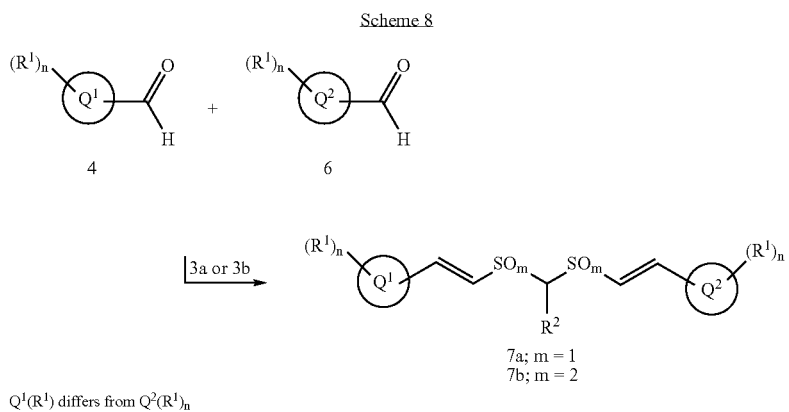

7a; m = 1
7b; m = 2

$Q^1(R^1)$ differs from $Q^2(R^1)_n$

According to Scheme 7, mercaptoacetic acid (CAS [68-11-1], Acros catalog # AC 12543), or a suitable ester thereof may be reacted with an aldehyde 1 to yield the corresponding methylene disulfide 2. Suitable esters of mercaptoacetic acid include, for example, benzyl and ($C_1$-$C_6$)alkyl esters. The reaction may be carried out in the presence of a suitable solvent. Suitable solvents include water and mixtures of water with water-miscible aprotic solvents.

The methylene disulfide 2 may be oxidized to a sulfone by reaction with a reagent capable of oxidizing a sulfide to a sulfone, to yield the methylene disulfone 3b. Alternately, the According to Scheme 8, aromatic aldehyde compounds 4 and 6 may be reacted with compound 3a, in glacial acetic acid in the presence of a catalytic amount of benzylamine to yield compound 7a, a compound according to Formula I wherein $M^1$ and $M^2$ are —SO—. Aromatic aldehyde compounds 4 and 6 may be reacted with compound 3b, in glacial acetic acid in the presence of a catalytic amount of benzylamine to yield compound 7b, a compound according to Formula I wherein $M^1$ and $M^2$ are —$SO_2$—. The reactions depicted in Scheme 8 will produce a methylene disulfoxide or methylene disulfone containing both a $Q^1$ and a $Q^2$ moiety in a mixture with compounds that contain two $Q^1$ moieties and with compounds that contain two $Q^2$ moieties. The desired product, wherein $Q^1(R^1)_n$ and $Q^2(R^1)_n$ are different, must be resolved from the other two reaction products. Preferred methods of resolving such a mixture of reaction products include preparative HPLC and column chromatography.

C. Selective Preparation of Non-symmetric α, β-Unsaturated Sulfones and Sulfoxides of Formula I Compounds of Formula I wherein L is CH, $M^1$ and $M^2$ are both —$SO_2$— or are both —SO—, and $E^1$ and $E^2$ are both carbon-carbon double bonds in the (E)-configuration, but wherein $Q^1(R^1)_n$ and $Q^2(R^1)_n$ are different, may be prepared according to the methods depicted in Scheme 9 by reacting an aromatic aldehyde compound 6 with methylene disulfoxide compound 8a, or with methylene disulfone compound 8b to yield a Formula I methylene disulfoxide compound 9a or a Formula I disulfone compound 9b respectively. The reaction is preferably carried out in glacial acetic acid in the presence of a catalytic amount of benzylamine.

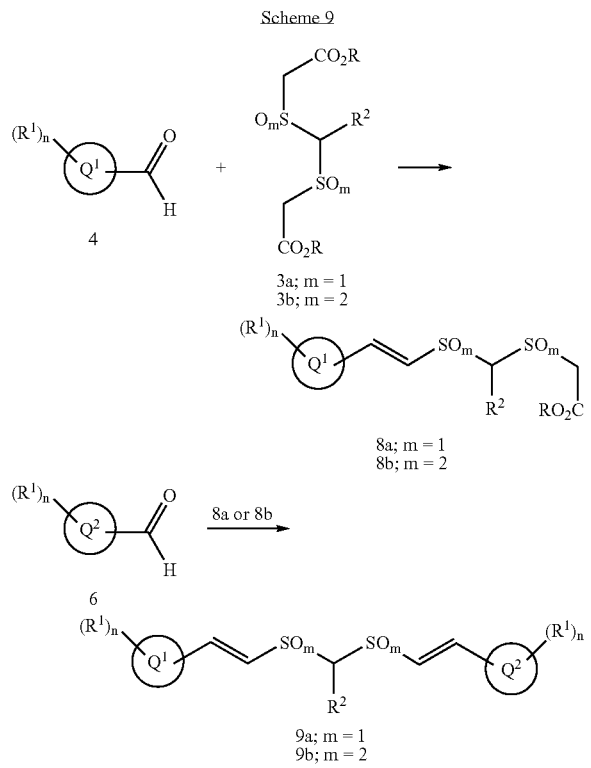

According to Scheme 9, aromatic aldehyde compound 4 may be reacted with methylene disulfoxide compound 3a, or with methylene disulfone compound 3b to yield methylene disulfoxide compound 8a, or methylene disulfone compound 8b. The reaction is preferably carried out in glacial acetic acid in the presence of a catalytic amount of benzylamine. The reaction to form compound 8a or 8b is preferably monitored in order to maximize the yield of the desired product and minimize double addition of 4 to 3a or 3b to form a symmetric compound as prepared in Scheme 7.

The aromatic aldehyde compound 6 may be reacted with methylene disulfoxide compound 8a, or with methylene disulfone compound 8b to yield compound 9a, a methylene disulfoxide compound of Formula I or compound 9b, a methylene disulfone compound of Formula I. The reaction is preferably carried out in glacial acetic acid in the presence of a catalytic amount of benzylamine.

D. Preparation of β-keto Sulfones and Sulfoxides wherein $Q^1$ and $Q^2$ are Identical Compounds of Formula I wherein L is CH, one of $M^1$ and $M^2$ is —$SO_2$— or —SO— and the other of $M^1$ and $M^2$ is —C(=O)—, $E^1$ and $E^2$ are both carbon-carbon double bonds in the (E)-configuration, $Q^1$ is identical to $Q^2$ and the $R^1$ substituents on $Q^1$ are identical to the $R^1$ substituents on $Q^2$, may be prepared according to the methods depicted in Scheme 10 by reacting an aromatic aldehyde compound 4, with either compound 11a or compound 11b.

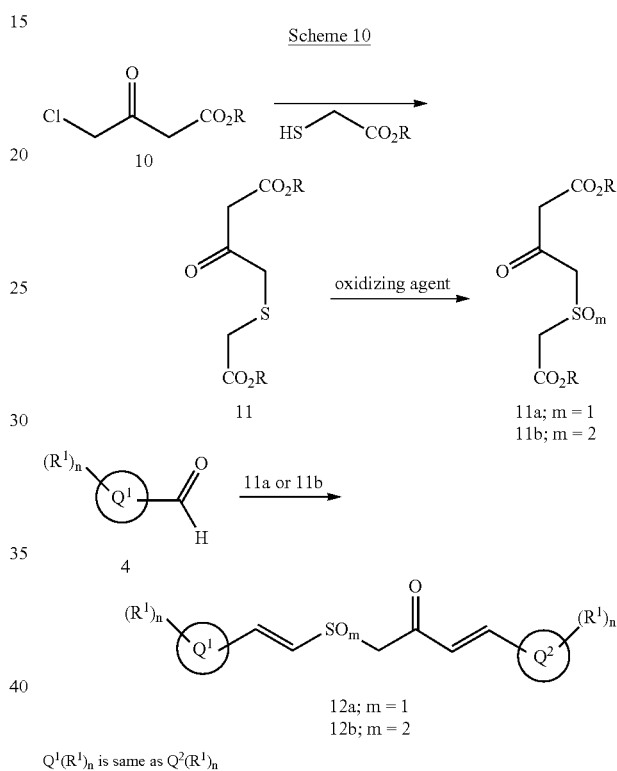

According to Scheme 10, chloroacetoacetic acid, or a suitable ester thereof is reacted with mercaptoacetic acid, or a suitable ester thereof to yield compound 11, 4-(carboxymethylthio)-3-oxobutanoic acid or an ester thereof. The reaction is preferably carried out in the presence of a suitable solvent and in the presence of a suitable acid scavenger. Suitable esters of compounds 10 and 11 include $C_1$-$C_6$ alkyl esters and benzyl esters, preferably $C_1$-$C_3$ esters such as methyl or ethyl esters. Suitable solvents include organic solvents such as acetonitrile, tetrahydrofuran, and DCM. Suitable acid scavengers include bases such as tertiary amines, e.g., triethylamine (TEA) and diisopropylethyl amine (DIPEA) and inorganic bases such as potassium carbonate, sodium carbonate, potassium bicarbonate and sodium bicarbonate.

Compound 11 may be oxidized to the corresponding sulfone 11b by reaction with a reagent capable of oxidizing a sulfide to a sulfone, or to the corresponding sulfoxide 11a by reaction with a reagent capable of oxidizing a sulfide to a sulfoxide. Suitable oxidizing reagents for both oxidation reactions include peroxides such as hydrogen peroxide, peracids such as meta-chloroperoxybenzoic acid (MCPBA) or persulfates such as potassium peroxymonosulfate. The reaction is preferably carried out in the presence of a suitable solvent. Suitable solvents include, for example, water, acetic acid or non-polar solvents such as dichloromethane (DCM). Reaction to selectively form the sulfoxide 11a is preferably performed at low temperature, more preferably from about −10° to about 20° C. In addition, the reaction to form the sulfoxide compound 11a is preferably monitored so as to terminate the reaction prior to appreciable oxidation to the sulfone. Reaction to form the sulfone 11b may be performed at higher temperature, for example, from about 30 to about 100° C.

Aromatic aldehyde 4 may be reacted with either ketosulfone compound 11b or ketosulfoxide compound 11a. The reaction is preferably carried out in glacial acetic acid in the presence of a catalytic amount of benzylamine.

E. Preparation of β-keto Sulfones and Sulfoxides wherein $Q^1$ and $Q^2$ are Different Compounds of Formula I wherein L is CH, one of $M^1$ and $M^2$ is —$SO_2$— or —SO— and the other of $M^1$ and $M^2$ is —C(=O)—, $E^1$ and $E^2$ are both carbon-carbon double bonds in the (E)-configuration, $Q^1$ is different from $Q^2$ and/or the $R^1$ substituents on $Q^1$ are different from the $R^1$ substituents on $Q^2$, may be prepared according to the methods depicted in Scheme 11 by reacting an aromatic aldehyde compound 6, with either compound 13a or compound 13b.

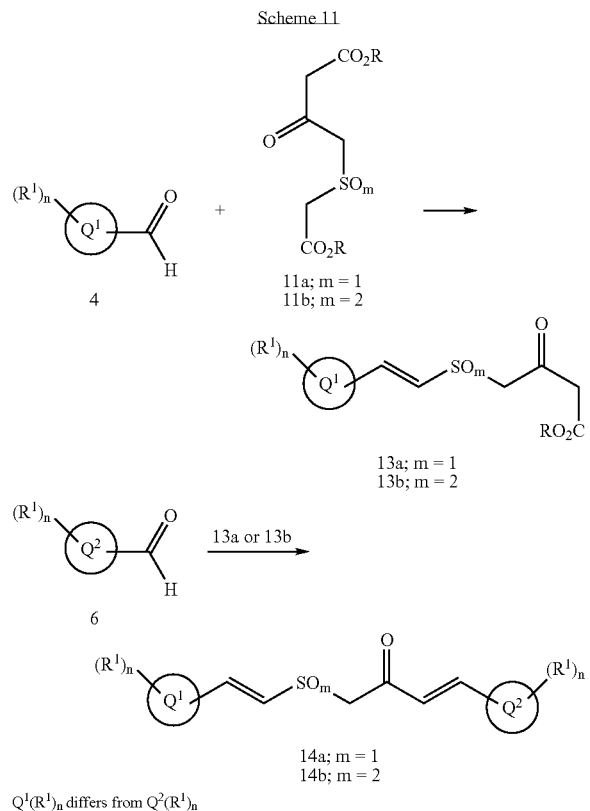

According to Scheme 11, aromatic aldehyde compound 4 may be reacted with β-ketosulfoxide compound 11a, or with β-ketosulfone compound 11b to yield β-ketosulfoxide compound 13a, or β-ketosulfone compound 13b respectively. The reaction is preferably carried out in glacial acetic acid in the presence of a catalytic amount of benzylamine. The reaction to form compound 13a or 13b is preferably monitored in order to maximize the yield of the desired product and minimize double addition of 4 to 11a or 11b to form a symmetric compound as prepared in Scheme 10.

Aromatic aldehyde compound 6 may be reacted with ketosulfoxide compound 13a, or with β-ketosulfone compound 13b to yield compound 14a, a ketosulfoxide compound of Formula I or compound 14b, a β-ketosulfone compound of Formula I. The reaction is preferably carried out in glacial acetic acid in the presence of a catalytic amount of benzylamine.

F. Preparation of Symmetrically Substituted Sulfonimide and Acylsulfonamide Compounds According to Formula I Compounds of Formula I wherein L is N, one of $M^1$ and $M^2$ is —$SO_2$— and the other of $M^1$ and $M^2$ is —$SO_2$— or —C(=O)—, $E^1$ and $E^2$ are both carbon-carbon double bonds in the (E)-configuration, $Q^1$ is identical to $Q^2$ and the $R^1$ substituents on $Q^1$ are identical to the $R^1$ substituents on $Q^2$, may be prepared according to the methods depicted in Scheme 12 by reacting an aromatic aldehyde compound 4, with compound 17.

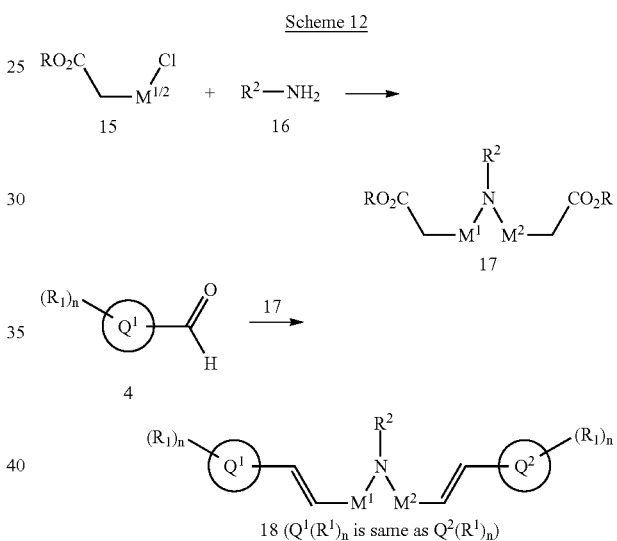

According to Scheme 12, compound 15 may be reacted with an amine 16 to yield the sulfonimide or acylsulfonamide 17. One example of compound 15 is ethylchlorosulfonyl acetate, CAS [55896-93-0]. The reaction may be carried out in the presence of a suitable solvent. Suitable solvents include organic solvents such as THF, DCM, ether or acetonitrile. The reaction is preferably carried out in the presence of an acid scavenger such as an organic base, e.g., triethyl amine (TEA) or diisopropylethyl amine (DIPEA), or an inorganic base such as an alkali metal carbonate or bicarbonate.

Aromatic aldehyde compound 4 may be reacted with compound 17 to yield compound 18, a sulfonimide or acylsulfonamide compound of Formula I. The reaction is preferably carried out in glacial acetic acid in the presence of a catalytic amount of benzylamine.

G. Preparation of Non-Symmetric Sulfonimide Compounds According to Formula I

Compounds of Formula I wherein L is N, one of $M^1$ and $M^2$ is —$SO_2$— and the other of $M^1$ and $M^2$ is —$SO_2$— or —C(=O)—, $E^1$ and $E^2$ are both carbon-carbon double bonds in the (E)-configuration, $Q^1$ is not the same as $Q^2$ and/or the $R^1$ substituents on $Q^1$ are not identical to the $R^1$ substituents on $Q^2$, may be prepared according to the methods depicted in Scheme 13 by reacting two aromatic aldehyde compounds 4 and 6, with compound 17, which is prepared as in Scheme 12.

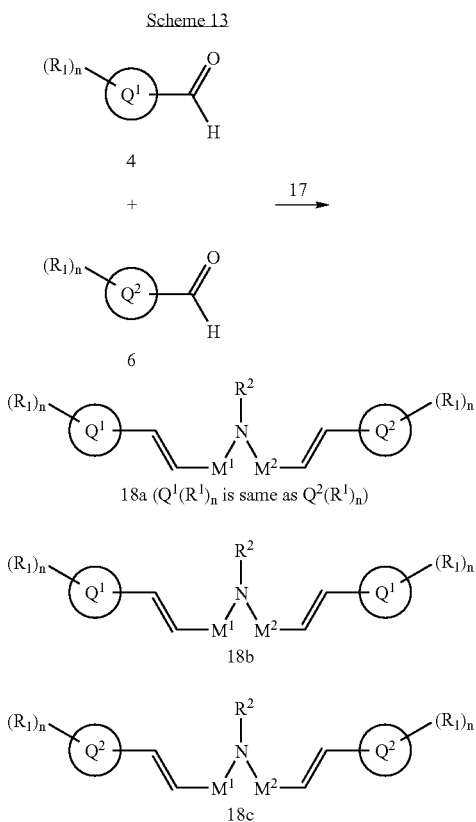

According to Scheme 13, aromatic aldehyde compounds 4 and 6 may be reacted with compound 17 to yield a mixture of compounds 18a, 18b, and 18c. Compound 18a is a compound of Formula I wherein $Q^1$ and $Q^2$ are different and/or the $R^1$ substituents on $Q^1$ are different from the $R^1$ substituents on $Q^2$. The reaction is preferably carried out in glacial acetic acid in the presence of a catalytic amount of benzylamine. Compounds 18b and 18c are products containing two $Q^1(R^1)_n$ groups (b) or two $Q^2(R^1)_n$ groups (18c). The desired non-symmetrical compound 18a may be isolated from the product mixture by a suitable separation such as, for example column chromatography or preparative HPLC.

V. Salts of Compounds According to the Invention

The compounds of the present invention may take the form of salts. The term "salts," embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, salicyclic, salicyclic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, toluenesulfonic, sulfanilic, cyclohexylaminosulfonic, stearic, algenic, γ-hydroxybutyric, salicyclic, galactaric and galacturonic acid. Examples of pharmaceutically unacceptable acid addition salts include, for example, perchlorates and tetrafluoroborates.

Suitable pharmaceutically-acceptable base addition salts of compounds of the invention include for example, metallic salts including alkali metal, alkaline earth metal and transition metal salts such as, for example, calcium, magnesium, potassium, sodium and zinc salts. Pharmaceutically-acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared by conventional means from the corresponding compound according to Formula I by reacting, for example, the appropriate acid or base with the compound according to Formula I.

VI. Administration of Compounds of the Invention

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

One or more compounds useful in the practice of the present inventions may be administered simultaneously, by the same or different routes, or at different times during treatment.

VII. Pharmaceutical Compositions

The compounds of the invention may be administered in the form of a pharmaceutical composition, in combination with a pharmaceutically acceptable carrier.

The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol.

Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a proliferative disorder will, of course, be determined by the particular circumstances of the individual patient including, the size, weight, age and sex of the patient, the nature and stage of the proliferative disorder, the aggressiveness of the proliferative disorder, and the route of administration of the compound.

For example, a daily dosage of from about 0.05 to about 50 mg/kg/day may be utilized. Higher or lower doses are also contemplated.

The practice of the invention is illustrated by the following non-limiting examples.

EXAMPLES

General Procedure 1: Synthesis of α,β-Unsaturated Sulfone Compounds According to Formula I.

A. Carboxymethanesulfonylmethanesulfonyl-acetic acid

To a round bottom flask containing 2,2'-(methylenedithio)diacetic acid (CAS [2068-24-8], 0.1 mol) dissolved in glacial acetic acid (25 mL) was added hydrogen peroxide (0.2 mol, 30% solution). The resulting mixture was heated at reflux temperature for about 2 hours. When the reaction was complete, the mixture was allowed to cool to room temperature (22-25° C.). Volatiles were removed under vacuum and the rest resulting residue was purified by column chromatography.

B. Aromatic Bis-Methylene Disulfone

An aromatic aldehyde (20 mmol) was dissolved in warm (40-50° C.) absolute ethanol (20 mL). To this solution was added carboxymethanesulfonylmethanesulfonyl-acetic acid (10 mmol) and three drops of piperidine. The resulting mixture was heated at reflux temperature for 5 min. The hot mixture was then allowed to cool to room temperature (22-25° C.). A precipitate formed in the cooled mixture. The precipitate was separated by filtration and washed three times with absolute ethanol to obtain the pure aromatic bis-methylene disulfone product.

The compounds of the following Examples 1-17 were made according to General Procedure I.

Example 1

4-((1E)-2-(((E)-4-Hydroxy-3-methoxystyrylsulfonyl)methylsulfonyl)vinyl)-2-methoxyphenol A solution of 3-methoxy-4-hydroxybenzaldehyde (2 mmol) and carboxymethane-sulfonylmethanesulfonyl-acetic acid (1 mmol) in acetic acid (10 mL) was subjected to General Procedure 1, to yield the title compound in 60% yield. m.p. 125-127° C.

$^1$H NMR (500 MHz, DMSO): 4.48 (2H), 6.86-7.03 (6H), 7.49-7.53 (2H), 7.51-7.54 (2H).

Example 2 bis((E)-2,4,6-Trimethoxystyrylsulfonyl)methane

A solution of 2,4,6-trimethoxybenzaldehyde (2 mmol) and carboxymethane-sulfonylmethanesulfonyl-acetic acid (1 mmol) in acetic acid (10 mL) was subjected to General Procedure 1, to yield the title compound in 68% yield. m.p. 140-142° C.

$^1$H NMR (500 MHz, DMSO): 4.47 (2H), 6.03 (4H), 7.31-7.35 (2H), 7.96-8.00 (2H).

Example 3

4-((1E)-2-(((E)-2-Fluoro-4-cyanostyrylsulfonyl)methylsulfonyl)vinyl)-3-fluorobenzonitrile A solution of 2-fluoro-4-cyanobenzaldehyde (2 mmol) and carboxymethane-sulfonylmethanesulfonyl-acetic acid (1 mmol) in acetic acid (10 mL) was subjected to General Procedure 1, to yield the title compound in 72% yield. m.p. 268-270° C.

Example 4 bis((E)-2,4-Difluorostyrylsulfonyl)methane

A solution of 2,4-difluorobenzaldehyde (2 mmol) and carboxymethane-sulfonylmethanesulfonyl-acetic acid (1 mmol) in acetic acid (10 mL) was subjected to General Procedure 1, to yield the title compound in 75% yield. m.p. 193-195° C.

Example 5 bis((E)-2,6-Dimethoxystyrylsulfonyl)methane

A solution of 2,6-dimethoxybenzaldehyde (2 mmol) and carboxymethane-sulfonylmethanesulfonyl-acetic acid (1 mmol) in acetic acid (10 mL) was subjected to General Procedure 1, to yield the title compound in 74% yield. m.p. 118-120° C.

Example 6 bis((E)-4-Chlorostyrylsulfonyl)methane

A solution of 4-chlorobenzaldehyde (2 mmol) and carboxymethane-sulfonylmethanesulfonyl-acetic acid (1 mmol) in acetic acid (10 mL) was subjected to General Procedure 1, to yield the title compound in 80% yield. m.p. 178-180° C.

Example 7 bis((E)-4-Bromostyrylsulfonyl)methane

A solution of 4-bromobenzaldehyde (2 mmol) and carboxymethane-sulfonylmethanesulfonyl-acetic acid (1 mmol) in acetic acid (10 mL) was subjected to General Procedure 1, to yield the title compound in 82% yield. m.p. 213-215° C.

Example 8 bis((E)-2-(Thiophen-3-yl)vinylsulfonyl)methane

A solution of thiophene-3-carbaldehyde (2 mmol) and carboxymethane-sulfonylmethanesulfonyl-acetic acid (1 mmol) in acetic acid (10 mL) was subjected to General Procedure 1, to yield the title compound in 55% yield. m.p. 150-152° C.

Example 9 bis((E)-Styrylsulfonyl)methane

A solution of benzaldehyde (2 mmol) and carboxymethane-sulfonylmethanesulfonyl-acetic acid (1 mmol) in acetic acid (10 mL) was subjected to General Procedure 1, to yield the title compound in 77% yield. m.p. 128-130° C.

Example 10 bis((E)-4-Iodostyrylsulfonyl)methane

A solution of 4-iodobenzaldehyde (2 mmol) and carboxymethane-sulfonylmethanesulfonyl-acetic acid (1 mmol) in acetic acid (10 mL) was subjected to General Procedure 1, to yield the title compound in 78% yield. m.p. 253-255° C.

Example 11 bis((E)-4-Fluorostyrylsulfonyl)methane

A solution of 4-fluorobenzaldehyde (2 mmol) and carboxymethane-sulfonylmethanesulfonyl-acetic acid (1 mmol) in acetic acid (10 mL) was subjected to General Procedure 1, to yield the title compound in 74% yield. m.p. 183-185° C.

Example 12 bis((E)-4-Methoxy-3-nitrostyrylsulfonyl)methane

A solution of 4-methoxy-3-nitrobenzaldehyde (2 mmol) and carboxymethane-sulfonylmethanesulfonyl-acetic acid (1 mmol) in acetic acid (10 mL) was subjected to General Procedure 1, to yield the title compound in 85% yield. m.p. 263-265° C.

Example 13 bis((E)-Perfluorostyrylsulfonyl)methane

A solution of 2,3,4,5,6-pentafluorobenzaldehyde (2 mmol) and carboxymethane-sulfonylmethanesulfonyl-acetic acid (1 mmol) in acetic acid (10 mL) was subjected to General Procedure 1, to yield the title compound in 68% yield. m.p. 193-195° C.

Example 14 bis((E)-3,4,5-Trimethoxystyrylsulfonyl)methane

A solution of 3,4,5-trimethoxybenzaldehyde (2 mmol) and carboxymethane-sulfonylmethanesulfonyl-acetic acid (1 mmol) in acetic acid (10 mL) was subjected to General Procedure 1, to yield the title compound in 62% yield. m.p. 127-129° C.

Example 15

4-((1E)-2-(((E)-4-hydroxy-2,6-dimethoxystyrylsulfonyl)methylsulfonyl)vinyl)-3,5-dimethoxyphenol.

A solution of 4-hydroxy-2,6-dimethoxybenzaldehyde (2 mmol) and carboxymethane-sulfonylmethanesulfonyl-acetic acid (1 mmol) in acetic acid (10 mL) was subjected to General Procedure 1, to yield the title compound in 62% yield. m.p. 148-150° C.
$^1$H NMR (500 MHz, DMSO): 4.45 (2H), 6.04 (4H), 7.35-7.38 (2H), 7.99-8.03 (2H).

Example 16

5-((1E)-2-(((E)-3-Hydroxy-4-methoxystyrylsulfonyl)methylsulfonyl)-vinyl)-2-methoxyphenol A solution of 3-hydroxy-4-methoxybenzaldehyde (2 mmol) and carboxymethane-sulfonylmethanesulfonyl-acetic acid (1 mmol) in acetic acid (10 mL) was subjected to General Procedure 1, to yield the title compound in 62% yield. m.p. 148-150° C.
$^1$H NMR (500 MHz, DMSO): 4.45 (2H), 6.04 (4H), 7.35-7.38 (2H), 7.99-8.03 (2H).

Example 17

5-((1E)-2-(((E)-3-Amino-4-methoxystyrylsulfonyl)methyl-sulfonyl)-vinyl)-2-methoxyphenol A solution of 3-amino-4-methoxybenzaldehyde (2 mmol) and carboxymethane-sulfonylmethanesulfonyl-acetic acid (1 mmol) in acetic acid (10 mL) was subjected to General Procedure 1, to yield the title compound in 62% yield. m.p. 148-150° C.

General Procedure 2: Synthesis of α,β-Unsaturated β-Ketosulfones According to Formula I A. 4-(carboxymethylthio)-3-oxobutanoic acid
To a round bottom flask containing mercaptoacetic acid (0.1 mol) dissolved in methanol (25 mL) is added 4-chloro-3-oxobutanoic acid (0.1 mol). The resulting mixture is heated at reflux temperature for about 2 hours. When the reaction is complete, the mixture is allowed to cool to room temperature (22-25° C.). Volatiles are removed under vacuum and the resulting residue is purified by column chromatography to yield 4-(carboxymethylthio)-3-oxobutanoic acid.

B. 4-(carboxymethylsulfonyl)-3-oxobutanoic acid
To a round bottom flask containing 4-(carboxymethylthio)-3-oxobutanoic acid (0.1 mol) dissolved in glacial acetic acid (25 mL) is added hydrogen peroxide (0.2 mol, 30% solution). The resulting mixture is heated at reflux temperature for about 2 hours. When the reaction is complete, the mixture is allowed to cool to room temperature (22-25° C.). Volatiles are removed under vacuum and the resulting residue is purified by column chromatography to yield 4-(carboxymethylsulfonyl)-3-oxobutanoic acid.

C. Aromatic α,β-Unsaturated β-Ketosulfones
An aromatic aldehyde (20 mmol) is dissolved in warm (40-50° C.) absolute ethanol (20 mL). To this solution is added 4-(carboxymethylsulfonyl)-3-oxobutanoic acid (10 mmol) and three drops of piperidine. The resulting mixture is heated at reflux temperature for 5 min. The hot mixture is then allowed to cool to room temperature (22-25° C.). Volatiles are removed under vacuum and the resulting residue is purified by column chromatography to yield the desired aromatic α,β-unsaturated β-ketosulfone.

The compounds of the following Examples 18-19 may be prepared according to General Procedure II.

Example 18

(3E)-1((E)-4-Hydroxy-3-methoxystyrylsulfonyl)-4-(4-hydroxy-3- methoxyphenyl)but-3-en-2-one.

A solution of 3 methoxy-4-hydroxybenzaldehyde (2 mmol) and 4-(carboxymethylsulfonyl)-3-oxobutanoic acid (1 mmol) in acetic acid (10 mL) is subjected to the General Procedure 2 to generate the title compound.

Example 19

(3E)-1-((E)-4-Hydroxy-2,6-dimethoxystyrylsulfonyl)-4-(4-hydroxy-2,6-dimethoxyphenyl)but-3-en-2-one A solution of 4-hydroxy-2,6-dimethoxybenzaldehyde (2 mmol) and 4-(carboxymethylsulfonyl) -3-oxobutanoic acid (1 mmol) in acetic acid (10 mL) is subjected to the General Procedure 2 to generate the title compound.

Example 20

Effect of α,β-Unsaturated Sulfones of Formula I on Tumor Cell Lines

A. Cells.

The effect of compounds according to Formula I on the growth of human tumor cells in culture was evaluated using the androgen receptor negative prostate (DU145) cell line. The cell culture was maintained at 37° C. in a humidified atmosphere of 5% $CO_2$.

B. Treatment of Cells with Compounds According to Formula I

Cells were treated with compounds according to Formula I at five different concentrations (1-100 μM range) for each compound. For comparison, the cells were treated with curcumin at the same concentrations. The dose response was established by determining the number of viable cells after 96 h of continuous treatment against each of the different test concentrations of each compound. The determination of viable cells was done by the Trypan blue exclusion method. Activity for each compound at each concentration is reported as a percentage of cells that remain viable.

Table 3 shows the $GI_{50}$ values, i.e., the concentration of each compound required to inhibit the growth of each tumor cell line by 50%, determined for each tested compound. The $GI_{50}$ values were determined by direct extrapolation from each dose response curve.

TABLE 1

| Example # | $R^1$ | $Q^1/Q^2$ | $GI_{50}$ μM vs. DU145 cell line |
|---|---|---|---|
| 1 | 3-OMe, 4-OH | Phenyl/phenyl | <10 |
| 2 | 2,4,6-trimethoxy | Phenyl/phenyl | 75 |
| 3 | 2-F, 4-CN | Phenyl/phenyl | 25-50 |
| 4 | 2,4-difluoro | Phenyl/phenyl | <10 |
| 5 | 2,6-dimethoxy | Phenyl/phenyl | 25-50 |
| 6 | 4-chloro | Phenyl/phenyl | 10-25 |
| 7 | 4-bromo | Phenyl/phenyl | <10 |
| 8 | Unsubstituted | 3-thiophene/3-thiophene | <10 |

TABLE 1-continued

| Example # | $R^1$ | $Q^1/Q^2$ | $GI_{50}$ μM vs. DU145 cell line |
|---|---|---|---|
| 9 | Unsubstituted | Phenyl/phenyl | 10-25 |
| 10 | 4-iodo | Phenyl/phenyl | Not tested |
| 11 | 4-fluoro | Phenyl/phenyl | <10 |
| 12 | 3-$NO_2$, 4-methoxy | Phenyl/phenyl | Not tested |
| 13 | 2,3,4,5,6-pentafluoro | Phenyl/phenyl | <2.5 |
| 14 | 3,4,5-trimethoxy | Phenyl/phenyl | 7.5 |
| 15 | 2,6-dimethoxy-4-hydroxy | Phenyl/phenyl | <1 |
| 16 | 3-OH, 4-OMe | Phenyl/phenyl | Not tested |
| 17 | 3-amino, 4-methoxy | Phenyl/phenyl | Not tested |
| curcumin | Comparative example - not a Formula I compound | | 35 |

Example 21

Inhibition of FLT1 by α,β-Unsaturated Sulfones of Formula I

The inhibition of FLT1 by compounds according to Formula I was assessed by employing an in vitro filter assay for FLT1.

Compounds 1-15 were prepared as 10 mmol stock solutions in DMSO. Curcumin was also prepared as a 10 mmol stock solution for testing in the FLT1 assay. Five units of recombinant FLT1 active protein was incubated with different concentrations of each compound in a 15 μl reaction mixture (50 mM HEPES, 10 mM $MgCl_2$, 1 mM EDTA, 2 mM Dithiothreitol 0.01% NP-40 pH 7.5) for 30 minutes at room temperature (25° C). Kinase reactions were performed for 20 minutes at 30° C. in a volume of 20 μl (15 μl enzyme+ compound of Formula I, 2 μl 1 mM ATP (100 μM final concentration), 2 μl of γ $32^P$ATP (40 μci final concentration) and 250 μM of IGF-1Rtide. 10 μl aliquots of the kinase reaction were spotted onto the center of a filter (2 cm×2 cm P81 phosphocellulose paper square). After 30 seconds, the filters were washed with 0.75% phosphoric acid (3×5 minutes) and once with acetone (5 minutes). The wet filters were transferred into a scintillation vial containing scintillation cocktail $^{32}P$ (5 mL). Radioactivity was determined using a scintillation counter. Control analyses were performed with DMSO stock solutions containing no compound. Binding values were corrected for non-specific binding by performing duplicate assays in the absence of FLT1 enzyme and subtracting the non-specific binding values from the values obtained in the presence of FLT1. Counts per minute (CPM) of aliquots containing a compound of Formula I were compared with CPM of control samples. The kinase activity is expressed in percent of the maximal kinase activity. Dose response curves were plotted for each compound tested and were used to calculate $IC_{50}$'s for the compounds which are listed below in Table 2. All assays were carried out in triplicate.

The results of the assay show that the compounds of the invention demonstrate a pattern of activity in the FLT1 assay wherein some compounds of Formula I are up to 450 times as potent as curcumin in inhibiting the activity of FLT1.

TABLE 2

| Example # | $R^1$ | $Q^1/Q^2$ | FLT1 IC50 (μM) |
|---|---|---|---|
| 1 | 3-OMe, 4-OH | Phenyl/phenyl | 3.89 |
| 2 | 2,4,6-trimethoxy | Phenyl/phenyl | 0.281 |

TABLE 2-continued

| Example # | R¹ | Q¹/Q² | FLT1 IC50 (μM) |
|---|---|---|---|
| 3 | 2-F, 4-CN | Phenyl/phenyl | 0.162 |
| 4 | 2,4-difluoro | Phenyl/phenyl | 2.23 |
| 5 | 2,6-dimethoxy | Phenyl/phenyl | 12.8 |
| 6 | 4-chloro | Phenyl/phenyl | 51 |
| 7 | 4-bromo | Phenyl/phenyl | 0.316 |
| 8 | Unsubstituted | 3-thiophene/3-thiophene | 11.2 |
| 9 | Unsubstituted | Phenyl/phenyl | >100 |
| 10 | 4-iodo | Phenyl/phenyl | >10 |
| 11 | 4-fluoro | Phenyl/phenyl | >100 |
| 12 | 3-NO₂, 4-methoxy | Phenyl/phenyl | Not tested |
| 13 | 2,3,4,5,6-pentafluoro | Phenyl/phenyl | 0.416 |
| 14 | 3,4,5-trimethoxy | Phenyl/phenyl | >10 |
| 15 | 2,6-dimethoxy-4-hydroxy | Phenyl/phenyl | 0.077 |
| 16 | 3-OH, 4-OMe | Phenyl/phenyl | Not tested |
| 17 | 3-amino, 4-methoxy | Phenyl/phenyl | Not tested |
| curcumin | Comparative example - not a Formula I compound | | 35 |

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication of the scope of the invention.

What is claimed is:
1. A compound according to Formula I:

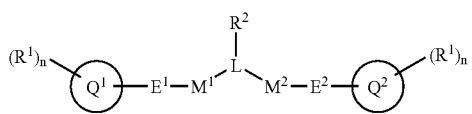

I wherein:
$Q^1$ and $Q^2$ are independently selected from the group consisting of aryl and heteroaryl;
each $R^1$ is independently selected from the group consisting of halogen, —($C_1$-$C_8$)hydrocarbyl, —C(=O)$R^y$, —N$R^w{}_2$, —N($R^w$)C(=O)$R^y$, —N($R^w$)CH($R^z$)C(=O)$R^y$, —N($R^w$)SO₂$R^y$, —N($R^w$)($C_1$-$C_4$)alkylene-CO₂$R^w$, —NO₂, —CN, —O$R^w$, —OC(=O)$R^y$, —OCH($R^z$)C(=O)$R^y$, —OSO₂$R^y$, —O($C_1$-$C_4$)alkylene-CO₂$R^w$, —OP(=O)(O$R^w$)₂, —O($C_2$-$C_6$)alkylene-N(CH₃)₂, —O($C_1$-$C_6$)haloalkyl, —P(=O)(O$R^w$)₂, —SO₂N($R^w$)$R^x$, —NHC(=NH)NH$R^x$, —($C_1$-$C_6$)haloalkyl and heteroalkyl;
each $R^w$ is independently —H or —($C_1$-$C_8$)hydrocarbyl;
each $R^x$ is independently —H, —($C_1$-$C_8$)hydrocarbyl or —C(=O)($C_1$-$C_8$)hydrocarbyl;
each $R^y$ is independently selected from the group consisting of —H, —($C_1$-$C_8$)hydrocarbyl, —O($C_1$-$C_8$)hydrocarbyl, substituted phenyl, substituted heterocyclyl($C_1$-$C_3$) alkyl, heteroaryl($C_1$-$C_3$)alkyl, —($C_2$-$C_{10}$)heteroalkyl, —($C_1$-$C_6$)haloalkyl, —C($R^z$)NH$R^x$, —N($R^w$)$R^x$, —($C_1$-$C_3$)alkyleneNH₂, —($C_1$-$C_3$)alkyleneN(CH₃)₂, —($C_1$-$C_3$)perfluoroalkyleneN(CH₃)₂, —($C_1$-$C_3$)alkyleneN⁺(($C_{1-3}$)alkyl)₃, —($C_1$-$C_3$)alkylene-N⁺(CH₂CH₂OH)₃, —($C_1$-$C_3$)alkylene-O$R^x$, —($C_1$-$C_4$)alkylene-CO₂$R^w$, —($C_1$-$C_4$)alkylene-CO₂N($R^w$)$R^x$, —($C_1$-$C_4$)alkylene-C(=O)halogen, halo($C_1$-$C_3$)alkyl and —($C_1$-$C_4$)perfluoroalkylene-CO₂$R^w$;
each $R^z$ is independently selected from the group consisting of —H, —($C_1$-$C_6$)alkyl, —(CH₂)₃—NH—C(NH₂)(=NH), —CH₂C(=O)NH₂, —CH₂COOH, —CH₂SH, —(CH₂)₂C(=O)—NH₂, —(CH₂)₂CO₂H, —CH₂-(2-imidazolyl), —(CH₂)₄—NH₂, —(CH₂)₂—S—CH₃, phenyl, —CH₂-phenyl, —CH₂—OH, —CH(OH)—CH₃, —CH₂-(3-indolyl) and —CH₂-(4-hydroxyphenyl);
each n is independently 0, 1, 2, 3, 4 or 5;
$M^1$ and $M^2$ are independently —SO₂—, —S(=O)— or —C(=O)—;
L is CH or N;
$R^2$ is selected from the group consisting of —H and —($C_1$-$C_6$)alkyl; and
$E^1$ and $E^2$ are independently selected from the group consisting of a carbon-carbon double bond in the (E)-configuration and a carbon-carbon double bond in the (Z)-configuration;
provided that:
(i) when one of $M^1$ and $M^2$ is —SO₂—, then the other of $M^1$ and $M^2$ is other than —S(=O)—;
(ii) when one of $M^1$ and $M^2$ is —C(=O)—, then the other of $M^1$ and $M^2$ is other than —C(=O)—;
(iii) when one of $E^1$ and $E^2$ is a carbon-carbon double bond in the (Z)-configuration, then the other of $E^1$ and $E^2$ is a carbon-carbon double bond in the (E)-configuration; and
(iv) when L is CH, $R^2$ is —H, $M^1$ and $M^2$ are —SO₂—, nd $Q^1$ and $Q^2$ are phenyl, then at least one n is greater than zero, and at least one substituent $R^1$ is other than —OH, —OC(=O)CH₃, —C(=O)CH₃, —OCH₃, —Br, —I, —NO₂, —CO₂($C_1$-$C_8$)hydrocarbyl, —SO₃($C_1$-$C_8$)hydrocarbyl, —P(=O)(O$R^w$)₂, and —OP(=O)(O$R^w$)₂;
or a salt of such a compound.

2. A compound or salt thereof according to claim 1, wherein the compound or salt thereof is an isolated compound.

3. A compound or salt thereof according to claim 1, wherein at least one of $Q^1$ and $Q^2$ is aryl.

4. A compound or salt thereof according to claim 3, wherein at least one of $Q^1$ and $Q^2$ is phenyl.

5. A compound or salt thereof according to claim 4, wherein $Q^1$ and $Q^2$ are phenyl.

6. A compound or salt thereof according to claim 1, wherein $Q^1$ and $Q^2$ are heteroaryl.

7. A compound or salt thereof according to claim 5 wherein L is CH.

8. A compound or salt thereof according to claim 7 wherein $M^1$ is —SO₂— and $M^2$ is selected from the group consisting of —SO₂— and —C(=O)—.

9. A compound or salt thereof according to claim 8 wherein $R^2$ is —H.

10. A compound according to claim 9 selected from the group consisting of:
4-((1E)-2-(((E)-2-fluoro-4-cyanostyrylsulfonyl)methylsulfonyl)vinyl)-3-fluoro-benzonitrile; 4-((1Z)-2-(((E)-2-fluoro-4-cyanostyrylsulfonyl)methylsulfonyl)vinyl)-3-fluoro-benzonitrile; (3E)-1-(2-fluoro-4-cyano-(E)-styrylsulfonyl)-4-(2-fluoro-4-cyanophenyl)but-3-en-2-one; (3Z)-1-(2-fluoro-4-cyano-(E)-styrylsulfonyl)-4-(2-fluoro-4-cyanophenyl)but-3-en-2-one; (3E)-1-(2-fluoro-4-cyano-(Z)-styrylsulfonyl)-4-(2-fluoro-4-cyanophenyl)but-3-en-2-one; bis((E)-2,4-difluorostyrylsulfonyl)methane; 1-((1Z)-2-(((E)-2,4- difluorostyrylsulfonyl)methylsulfonyl)vinyl)-2,4-difluorobenzene; (3E)-1-(2,4-difluoro-(E)-styrylsulfonyl)-4-(2,4-difluorophenyl)but-3-en-2-one; (3Z)-1-(2,4-difluoro-(E)-styrylsulfonyl)-4-(2,4-difluorophenyl)but-3-en-2-one; (3E)-1-(2,4-difluoro-(Z)-styryl-sulfonyl)-4-(2,4-difluorophenyl)but-3-en-2-one; bis((E)-4-chlorostyrylsulfonyl)methane; 1-((1Z)-2-(((E)-4-chlorostyrylsulfonyl)methylsulfonyl)vinyl)-4-chlorobenzene; (3E)-1-(4-chloro-(E)-styrylsulfonyl)-4-(4-chlorophenyl)but-3-en-2-one; (3Z)-1-(4-chloro-(E)-styryl-sulfonyl)-4-(4-chlorophenyl)but-3-en-2-one; (3E)-1-(4-chloro-(Z)-styrylsulfonyl)-4-(4-chlorophenyl)but-3-en-2-one; bis((E)4-fluorostyrylsulfonyl)methane; 1-((1Z)-2-(((E)-4-fluorostyrylsulfonyl)methylsulfonyl)vinyl)-4-fluorobenzene; (3E)-1-(4-fluoro-(E)-styryl-sulfonyl)-4-(4-fluorophenyl)but-3-en-2-one; (3Z)-1-(4-fluoro-(E)-styrylsulfonyl)-4-(4-fluorophenyl)but-3-en-2-one; (3E)-1-(4-fluoro-(Z)-styrylsulfonyl)-4-(4-fluorophenyl)but-3-en-2-one; bis((E)-2-(thiophen-3-yl)vinylsulfonyl)methane; 3-((1E)-2-(((Z-2-(thiophen-3-yl)vinylsulfonyl)methylsulfonyl)vinyl) thiophene; (3E)-1-((E)-2-(thiophen-3-yl)vinyl-sulfonyl)-4-(thiophen-3-yl)but-3-en-2-one; (3E)-1-((Z)-2-(thiophen-3-yl)vinylsulfonyl)-4-(thiophen-3-yl) but-3-en-2-one; (3Z)-1-((E)-2-(thiophen-3-yl) vinylsulfonyl)-4-(thiophen-3-yl)but-3-en-2-one; bis ((E)-perfluorostyrylsulfonyl)methane; 1-((1Z)-2-(((E)-perfluoro styrylsulfonyl)methyl-sulfonyl)vinyl)-2,3,4, 5,6-pentafluorobenzene; (3E)-4-((E)-perfluorophenyl)-1-(perfluorostyryl-sulfonyl)but-3-en-2-one; (3Z)-4-((E)-perfluorophenyl)-1-(perfluorostyrylsulfonyl)but-3-en-2-one; (3E)-4-((Z)-perfluorophenyl)-1-(perfluorostyrylsulfonyl)but-3-en-2-one; 5-((1E)-2-(((E)-3-amino-4-methoxystyrylsulfonyl) methylsulfonyl)vinyl)-2-methoxybenzenamine; 5-((1Z)-2-(((E)-3-amino-4-methoxystyrylsulfonyl)methylsulfonyl)vinyl)-2-methoxybenzenamine; (3E)-1-((E)-3-amino-4-methoxystyrylsulfonyl)-4-(3-amino-4-methoxyphenyl)but-3-en-2-one; (3Z)-1-((E)-3-amino-4-methoxystyrylsulfonyl)-4-(3-amino-4-methoxyphenyl)but-3-en-2-one; (3E)-1-((Z))-3-amino-4-methoxystyrylsulfonyl)-4-(3-amino-4-methoxyphenyl)but-3-en-2-one; (3E)-1-((E)-4-methoxy-3-nitrostyrylsulfonyl)-4-(4-methoxy-3-nitrophenyl)but-3-en-2-one; (3Z)-1-((E)-4-methoxy-3-nitrostyrylsulfonyl)-4-(4-methoxy-3-nitrophenyl)but-3-en-2-one; (3E)-1-((Z)-4-methoxy-3-nitrostyrylsulfonyl)-4-(4-methoxy-3-nitrophenyl)but-3-en-2-one; (3E)-1-((E)-4-hydroxy-3-methoxystyrylsulfonyl)-4-(4-hydroxy-3-methoxyphenyl)-but-3-en-2-one; (3E)-1-((Z)-4-hydroxy-3-methoxystyrylsulfonyl)-4-(4-hydroxy-3-methoxyphenyl)but-3-en-2-one; (3Z)-1-((E)-4-hydroxy-3-methoxystyrylsulfonyl)-4-(4-hydroxy-3-methoxyphenyl)but-3-en-2-one; (3E)-1-((E)-2,4,6-trimethoxystyrylsulfonyl)-4-(2,4,6-trimethoxyphenyl) but-3-en-2-one; (3E)-1-((Z)-2,4,6-trimethoxystyrylsulfonyl)-4-(2,4,6-trimethoxyphenyl) but-3-en-2-one; (3Z)-1-((E)-2,4,6-trimethoxystyrylsulfonyl)-4-(2,4,6-trimethoxyphenyl) but-3-en-2-one; (3E)-1-((E)-2,6-dimethoxystyrylsulfonyl)-4-(2,6-dimethoxyphenyl) but-3-en-2-one; (3E)-1-((Z)-2,6-dimethoxystyrylsulfonyl)-4-(2,6-trimethoxyphenyl) but-3-en-2-one; (3Z)-1-((E)-2,6-dimethoxystyrylsulfonyl)-4-(2,6-dimethoxyphenyl) but-3-en-2-one; (3E)-1-((E)-4-bromostyrylsulfonyl)-4-(4-bromophenyl)but-3-en-2-one; (3E)-1-((Z)-4-bromostyrylsulfonyl)-4-(4-bromophenyl)but-3-en-2-one; (3Z)-1-((E)-4-bromostyrylsulfonyl)-4-(4-bromophenyl)but-3-en-2-one; (3E)-4-phenyl-1((E)-styrylsulfonyl)but-3-en-2-one; (3E)-4-phenyl-1-((Z)-styrylsulfonyl)but-3-en-2-one; (3Z)-4-phenyl-1((E)-styrylsulfonyl)but-3-en-2-one; (3E)-1-((E)-3,4,5-trimethoxystyrylsulfonyl)-4-(3,4,5-trimethoxyphenyl) but-3-en-2-one; (3E)-1-((Z)-3,4,5-trimethoxystyrylsulfonyl)-4-(3,4,5-trimethoxyphenyl) but-3-en-2-one; (3Z)-1-((E)-3,4,5-trimethoxystyrylsulfonyl)-4-(3,4,5-trimethoxyphenyl) but-3-en-2-one; (3E)-1-((E)-4-hydroxy-2,6-dimethoxystyrylsulfonyl)-4-(4-hydroxy-2,6-dimethoxyphenyl)but-3-en-2-one; (3E)-1-((Z)-4-hydroxy-2,6-dimethoxystyrylsulfonyl)-4-(4-hydroxy-2,6-dimethoxyphenyl)but-3-en-2-one; (3Z)-1-((E)-4-hydroxy-2,6-dimethoxystyrylsulfonyl)-4-(4-hydroxy-2,6-dimethoxyphenyl)but-3-en-2-one; (3E)-1-((E)-4-iodostyrylsulfonyl)-4-(4-iodophenyl)but-3-en-2-one; (3E)-1-((Z-4-iodostyrylsulfonyl)-4-(4-iodophenyl)but-3-en-2-one; (3Z)-1-((E)-4-iodostyrylsulfonyl)-4-(4-iodophenyl)but-3-en-2-one; (3E)-1-((E)-3-hydroxy-4-methoxystyrylsulfonyl)-4-(3-hydroxy-4-methoxyphenyl)-but-3-en-2-one; (3E)-1-((Z)-3-hydroxy-4-methoxystyrylsulfonyl)-4-(3-hydroxy-4-methoxyphenyl)but-3-en-2-one; (3Z)-1-((E)-3-hydroxy-4-methoxystyrylsulfonyl)-4-(3-hydroxy-4-methoxyphenyl)but-3-en-2-one; and salts thereof.

11. A compound or salt thereof according to claim 10 which is an isolated compound.

12. A compound or salt thereof according to claim 7 wherein $M^1$ is —S(=O)— and $M^2$ is selected from the group consisting of —S(=O)— and —C(=O)—.

13. A compound or salt thereof according to claim 12 wherein $R^2$ is —H.

14. A compound according to claim 13 selected from the group consisting of:

4-((1E)-2-(((E)-2-fluoro-4-cyanostyrylsulfinyl)methylsulfinyl)vinyl)-3-fluoro-benzo-nitrile; 4-((1Z)-2-(((E)-2-fluoro-4-cyanostyrylsulfinyl)methylsulfinyl)vinyl)-3-fluorobenzonitrile; (3E)-1-(2-fluoro-4-cyano-(E)-styrylsulfinyl)-4-(2-fluoro-4-cyanophenyl)but-3-en-2-one; (3Z)-1-(2-fluoro-4-cyano-(E)-styrylsulfinyl)-4-(2-fluoro-4-cyanophenyl)but-3-en-2-one; (3E)-1-(2-fluoro-4-cyano-(Z)-styrylsulfinyl)-4-(2-fluoro-4-cyanophenyl)but-3-en-2-one; bis((E)-2,4-difluorostyrylsulfinyl)methane; 1-((1Z)-2-(((E)-2,4-difluorostyrylsulfinyl)methylsulfinyl)vinyl)-2,4-difluorobenzene; (3E)-1-(2,4-difluoro-(E)-styrylsulfinyl)-4-(2,4-difluorophenyl)but-3-en-2-one; (3Z)-1-(2,4-difluoro-(E)-styrylsulfinyl)-4-(2,4-difluorophenyl)but-3-en-2-one; (3E)-1-(2,4-difluoro-(Z)-styryl-sulfinyl)-4-(2,4-difluorophenyl)but-3-en-2-one; bis((E)-4-chlorostyrylsulfinyl)methane; 1-((1Z)-2-(((E)-4-chlorostyrylsulfinyl)methylsulfinyl)vinyl)-4-chlorobenzene; (3E)-1-(4-chloro-(E)-styrylsulfinyl)-4-(4-chlorophenyl)but-3-en-2-one; (3Z)-1-(4-chloro-(E)-styryl-sulfinyl)-4-(4-chlorophenyl)but-3-en-2-one; (3E)-1-(4-chloro-(Z)-styrylsulfinyl)-4-(4-chlorophenyl)but-3-en-2-one; bis((E)4-fluorostyrylsulfinyl) methane; 1-((1Z)-2-(((E)-4-fluorostyrylsulfinyl)methylsulfinyl)vinyl)-4-fluorobenzene; (3E)-1-(4-fluoro-(E)-styryl-sulfinyl)-4-(4-fluorophenyl)but-3-en-2-one; (3Z)-1-(4-fluoro-(E)-styrylsulfinyl)-4-(4-fluorophenyl) but-3-en-2-one; (3E)-1-(4-fluoro-(Z)-styrylsulfinyl)-4-(4-fluorophenyl)but-3-en-2-one; bis((E)-2-(thiophen-3- yl)vinylsulfinyl)methane; 3-((1E)-2-(((Z)-2-(thiophen-3-yl)vinyl-sulfinyl)methylsulfinyl)vinyl)thiophene; (3E)-1-((E)-2-(thiophen-3-yl)vinyl-sulfinyl)-4-(thiophen-3-yl)but-3-en-2-one; (3E)-1-((Z)-2-(thiophen-3-yl)vinyl-sulfinyl)-4-(thiophen-3-yl)but-3-en-2-one; (3Z)-1-((E)-2-(thiophen-3-yl)vinylsulfinyl)-4-(thiophen-3-yl)but-3-en-2-one; bis((E)-perfluorostyrylsulfinyl)methane; 1-((1Z)-2-(((E)-perfluorostyrylsulfinyl)methylsulfinyl)-vinyl)-2,3,4,5,6-pentafluorobenzene; (3E)-4-((E)-perfluorophenyl)-1-(perfluorostyryl-sulfinyl)but-3-en-2-one; (3Z)-4-((E)-perfluorophenyl)-1-(perfluorostyrylsulfinyl)but-3-en-2-one; (3E)-4-((Z)-perfluorophenyl)-1-(perfluorostyrylsulfinyl)but-3-en-2-one; 5-((1E)-2-(((E)-3-amino-4-methoxystyrylsulfinyl) methylsulfinyl)vinyl)-2-methoxybenzenamine; 5-((1Z)-2-(((E)-3-amino-4-methoxystyrylsulfinyl)methylsulfinyl)vinyl)-2-methoxybenzenamine; (3E)-1-((E)-3-amino-4-methoxystyrylsulfinyl)-4-(3-amino-4-methoxyphenyl)but-3-en-2-one; (3Z)-1-((E)-3-amino-4-methoxystyrylsulfinyl)-4-(3-amino-4-methoxyphenyl)but-3-en-2-one; (3E)-1-((Z)-3-amino-4-inethoxystyrylsulfinyl)-4-(3-amino-4-methoxyphenyl)but-3-en-2-one; bis((E)-4-methoxy-3-nitrostyrylsulfinyl)methane; 4-((1Z)-2-(((E)-4-methoxy-3-nitrostyryl-sulfinyl)methylsulfinyl)vinyl)-1-methoxy-2-nitrobenzene; (3E)-1-((E)-4-methoxy-3-nitrostyrylsulfinyl)-4-(4-methoxy-3-nitrophenyl)but-3-en-2-one; (3Z)-1-((E)-4-methoxy-3-nitrostyrylsulfinyl)-4-(4-methoxy-3-nitrophenyl)but-3-en-2-one; (3E)-1-((Z)-4-methoxy-3-nitrostyrylsulfinyl)-4-(4-methoxy-3-nitrophenyl)but-3-en-2-one; 4-((1E)-2((4-hydroxy-3-methoxy-(E)-styrylsulfinyl)methylsulfinyl)vinyl)-2-methoxyphenol; 4-((1E)-2-((4-hydroxy-3-methoxy-(Z)-styrylsulfinyl) methylsulfinyl)vinyl)-2-methoxyphenol; (3E)-1-((E)-4-hydroxy-3-methoxystyrylsulfinyl)-4-(4-hydroxy-3-methoxyphenyl)-but-3-en-2-one; (3E)-1-((Z)-4-hydroxy-3-methoxystyrylsulfinyl)-4-(4-hydroxy-3-methoxyphenyl)but-3-en-2-one; (3Z)-1-((E)-4-hydroxy-3-methoxystyrylsulfinyl)-4-(4-hydroxy-3-methoxyphenyl)but-3-en-2-one; bis((E)-2,4,6-trimethoxystyrylsulfinyl)methane; 2-((1E)-2-(((Z)-2,4,6-trimethoxystyrylsulfinyl)methyl-sulfinyl)vinyl)-1,3,5-trimethoxybenzene; (3E)-1-((E)-2,4,6-trimethoxystyrylsulfinyl)-4-(2,4,6-trimethoxyphenyl)but-3-en-2-one; (3E)-1-((Z)-2,4,6-trimethoxystyrylsulfinyl)-4-(2,4,6-trimethoxyphenyl)but-3-en-2-one; (3Z)-1-((E)-2,4,6-trimethoxystyrylsulfinyl)-4-(2,4,6-trimethoxyphenyl)but-3-en-2-one; bis((E)-2,6-dimethoxystyrylsulfinyl)methane; 2 ((1E)-2-(((Z)-2,6-dimethoxystyrylsulfinyl)methylsulfinyl)vinyl)-1,3-dimethoxybenzene; (3E)-1-((E)-2,6-dimethoxystyrylsulfinyl)-4-(2,6-dimethoxyphenyl)but-3-en-2-one; (3E)-1-((Z)-2,6-dimethoxystyrylsulfinyl)-4-(2,6-trimethoxyphenyl)but-3-en-2-one; (3Z)-1-((E)-2,6-dimethoxystyrylsulfinyl)-4-(2,6-dimethoxyphenyl)but-3-en-2-one; bis((E)-4-bromostyryl-sulfinyl)methane; 1-((1Z)-2-(((E)-4-bromostyrylsulfinyl)methylsulfinyl) vinyl)-4-bromobenzene; (3E)-1-((E)-4-bromostyryl-sulfinyl)-4-(4-bromophenyl)but-3-en-2-one; (3E)-1-((Z)-4-bromostyrylsulfinyl)-4-(4-bromophenyl)but-3-en-2-one; (3Z)-1-((E )-4-bromostyrylsulfinyl)-4-(4-bromophenyl)but-3-en-2-one; bis((E)-styrylsulfinyl) methane; 1-((1Z)-2-(((E)-styrylsulfinyl)-methylsulfinyl)vinyl)benzene; (3E)-4-phenyl-1-((E)-styrylsulfinyl)but-3-en-2-one; (3E)-4-phenyl-1-((Z)-styrylsulfinyl)but-3-en-2-one; (3Z)-4-phenyl-1((E)-styrylsulfinyl)but-3-en-2-one; bis((E)-3,4,5-trimethoxystyrylsulfinyl)methane; 5-((1Z)-2-(((E)-3,4,5-trimethoxystyrylsulfinyl)methylsulfinyl)vinyl)-1,2,3-trimethoxybenzene; (3E)-1-((E)-3,4,5-trimethoxystyrylsulfinyl)-4-(3,4,5-trimethoxyphenyl) but-3-en-2-one; (3E)-1-((Z)-3,4,5-trimethoxystyrylsulfinyl)-4-(3,4,5-trimethoxyphenyl) but-3-en-2-one; (3Z)-1-((E)-3,4,5-trimethoxystyryl-sulfinyl)-4-(3,4,5-trimethoxyphenyl)but-3-en-2-one; 4-((1E)-2-(((E)-4-hydroxy-2,6-dimethoxystyrylsulfinyl)methylsulfinyl)vinyl)-3,5-dimethoxyphenol; 4-((1E)-2-(((E)-4-hydroxy-2,6-dimethoxystyrylsulfinyOmethylsulfinyl)vinyl)-3,5-dimethoxyphenol; (3E)-1-((E)-4-hydroxy-2,6-dimethoxystyrylsulfinyl)-4-(4-hydroxy-2,6-dimethoxyphenyl)but-3-en-2-one; (3E)-1-((Z-4-hydroxy-2,6-dimethoxystyrylsuffinyl)-4-(4-hydroxy-2,6-dimethoxyphenyl)but-3-en-2-one; (3Z)-1-((E)-4-hydroxy-2,6-dimethoxystyrylsulfinyl)-4-(4-hydroxy-2,6-dimethoxyphenyl)-but-3-en-2-one; bis ((E)-4-iodostyrylsulfinyl)methane; 1-((1Z)-2-(((E)-4-iodostyrylsulfinyl)methylsulfinyl)vinyl)-4-iodobenzene; (3E)-1-((E)-4-iodostyrylsulfinyl)-4-(4-iodophenyl)but-3-en-2-one; (3E)-1-((Z)-4-iodostyrylsuffinyl)-4-(4-iodophenyl)but-3-en-2-one; (3Z)-1-((E)-4-iodostyrylsuffinyl)-4-(4-iodophenyl)but-3-en-2-one; 5((1E)-2-(((E)-3-hydroxy-4-methoxystyrylsulfinyl)methylsulfinyl)vinyl)-2-methoxyphenol; 5-((1E)-2-(((Z)-3-hydroxy-4-methoxystyrylsulfinyl) methylsulfinyl)vinyl)-2-methoxyphenol; (3E)-1-((E)-3-hydroxy-4-methoxystyrylsulfinyl)-4-(3-hydroxy-4-methoxyphenyl)-but-3-en-2-one; (3E)-1-((Z)-3-hydroxy-4-methoxystyrylsuffinyl)-4-(3-hydroxy-4-methoxyphenyl)but-3-en-2-one; (3Z)-1-((E)-3-hydroxy-4-methoxystyrylsulfinyl)-4-(3-hydroxy-4-methoxyphenyl)but-3-en-2-one; and salts thereof.

15. A compound or salt thereof according to claim 14 which is an isolated compound.

16. A compound or salt thereof according to claim 5 wherein L is N.

17. A compound or salt thereof according to claim 16 wherein $M^1$ is —$SO_2$— and $M^2$ is selected from the group consisting of —$SO_2$— and —C(=O)—.

18. A compound according to claim 17 selected from the group consisting of:

bis{[(1E)-2-(4-hydroxy-3-methoxyphenyl)vinyl] sulfonyl}amine; (2E)-N-{[(1E)-2-(4-hydroxy-3-methoxyphenyl)vinyl]sulfonyl}-3-(4-hydroxy-3-methoxyphenyl)prop-2-enamide; {[(1E)-2-(4-hydroxy-3-methoxyphenyl)vinyl]sulfonyl}{[(1Z)-2-(4-hydroxy-3-methoxyphenyl)vinyl]sulfonyl}amine; (2E)-N-{[(1Z)-2-(4-hydroxy-3-methoxyphenyl)vinyli-sulfonyl}-3-(4-hydroxy-3-methoxyphenyl)prop-2-enamide; N-{[(1E)-2-(4-hydroxy-3-methoxyphenyl)vinyl]sulfonyl }(2Z)-3-(4-hydroxy-3-methoxyphenyl)prop-2-enamide; bis{[(1E)-2-(3,4,5-trimethoxyphenyl)vinyl] sulfonyl}amine; (2E)-N-{[(1E)-2-(3,4,5-trimethoxyphenyl)vinyl]sulfonyl}-3-(3,4,5-trimethoxyphenyl) prop-2-enamide; {[(1E)-2-(3 ,4,5-trimethoxyphenyl) vinyl]sulfonyl}{[(1Z)-2-(3,4,5-trimethoxyphenyl) vinyl]sulfonyl }amine; (2E)-N-{[(1Z)-2-(3,4,5-trimethoxyphenyevinyl]sulfonyl}-3-(3,4,5-trimethoxyphenyl)prop-2-enamide; N-{[(1E)-2-(3,4,5-trimethoxyphenyl)vinyl]sulfonyl}(2Z)-3-(3,4,5-trimethoxyphenyl)prop-2-enamide; bis{[(1E)-2-(2,3,4,5,6-pentafluorophenyl)vinyl]sulfonyl}amine; (2E)-N-

{[(1E)-2-(2,3,4,5,6-pentafluorophenyl)vinyl]sulfonyl}-3-(2,3,4,5,6-pentafluorophenyl)prop-2-enamide; {[(1E)-2-(2,3,4,5,6-pentafluorophenyl)vinyl]sulfonyl}{[(1Z)-2-(2,3,4,5,6-pentafluorophenyl)vinyl]sulfonyl}amine; (2E)-N-{[(1Z)-2-(2,3,4,5,6-pentalluorophenyl)vinyl]sulfonyl}-3-(2,3,4,5,6-pentafluorophenyl)prop-2-enamide; N-{[(1E)-2-(2,3,4,5,6-pentafluorophenyl)vinyl]sulfonyl}(2Z)-3-(2,3,4,5,6-pentafluorophenypprop-2-enamide; bis{[(1E)-2-(2,4,6-trimethoxyphenyl)vinyl]sulfonyl}amine; (2E)-N-{[(1E)-2-(2,4,6-trimethoxyphenyl)vinyl]sulfonyl}-3-(2,4,6-trimethoxyphenyl)prop-2-enamide; {[(1E)-2-(2,4,6-trimethoxyphenyl)vinyl]sulfonyl}{[(1Z)-2-(2,4,6-trimethoxyphenyl)vinyl]sulfonyl }amine; (2E)-N-{[(1Z)-2-(2,4,6-trimethoxyphenyl)vinyl]sulfonyl}-3-(2,4,6-trimethoxyphenyl)prop-2-enamide; N-{[(1E)-2-(2,4,6-trimethoxyphenyl)vinyl]sulfonyl}(2Z)-3-(2,4,6-trimethoxyphenyl)prop-2-enamide; bis{[(1E)-2-(4-hydroxy-2,6-dimethoxyphenyl)vinyl]sulfonyl}amine; (2E)-N-{[(1E)-2-(4-hydroxy-2,6-dimethoxyphenyl)vinyl]sulfonyl}-3-(4-hydroxy-2,6-dimethoxyphenyl)prop-2-enamide; {[(1E)-2-(4-hydroxy-2,6-dimethoxyphenyl)vinyl]sulfonyl}{[(1Z)-2-(4-hydroxy-2,6-dimethoxypheny)vinyl]sulfonyl}amine; (2E)-N-{[(1Z)-2-(4-hydroxy-2,6-dimethoxyphenyl)vinyl]sulfonyl}-3-(4-hydroxy-2,6-dimethoxyphenyl)prop-2-enamide; N-{[(1E)-2-(4-hydroxy-2,6-dimethoxyphenyOvinyl]sulfonyl}(2Z)-3-(4-hydroxy-2,6-dimethoxyphenyl)prop-2-enamide; bis{[(1E)-2-(2,6-dimethoxyphenyl)vinyl]sulfonyl}amine; (2E)- N-{[(1E)-2-(2,6-dimethoxyphenyl)vinyl]sulfonyl}-3-(2,6-dimethoxyphenyl)prop-2-enamide; {[(1E)-2-(2,6-dimethoxyphenyl)vinyl]sulfonyl}{[(1Z)-2-(2,6-dimethoxy-phenyl)vinyl]sulfonyl}amine; (2E)-N-{[(1Z)-2-(2,6-dimethoxyphenyl)vinyl]sulfonyl}-3-(2,6-dimethoxyphenyl)prop-2-enamide; N-{[(1E)-2-(2,6-dimethoxyphenyl)vinyl]sulfonyl}(2Z)-3-(2,6-dimethoxyphenyl)prop-2-enamide; 4-{(1E)-2-[({[(1E)-2-(4-cyano-2-fluorophenyl)vinyl]sulfonyl}amino)sulfonyl]vinyl}-3-fluorobenzenecarbonitrile; (2E)-N-{[(1E)-2-(4-cyano-2-fluorophenyl)vinyl]sulfonyl}-3-(4-cyano-2-fluorophenyl)prop-2-enamide ; 4-{(1E)-2-[({[(1Z)-2-(4-cyano-2-fluorophenyl)vinyl]sulfonyl}amino)sulfonyl]vinyl}-3-fluorobenzenecarbonitrile; (2E)-N-{[(1Z)-2-(4-cyano-2-fluorophenyl)vinyl]sulfonyl}-3-(4-cyano-2-fluorophenyl)prop-2-enamide; N-{[(1E)-2-(4-cyano-2-fluorophenyl)-vinyl]sulfonyl}(2Z)-3-(4-cyano-2-fluorophenyl)prop-2-enamide; bis{[(1E)-2-(2,4-difluorophenyl)vinyl]sulfonyl}amine; (2E)-N-{[(1E)-2-(2,4-difluorophenyl)vinyl]sulfonyl}-3-(2,4-difluorophenyl)prop-2-enamide;{[(1E)-2-(2,4-difluorophenyl)vinyl]sulfonyl }{[(1Z)-2-(2,4-difluorophenyl)vinyl]sulfonyl}amine; (2E)-N-{[(1Z)-2-(2,4-difluorophenyl)vinyl]sulfonyl}-3-(2,4-difluorophenyl)prop-2-enamide; N-{[(1E)-2-(2,4-difluorophenyl)vinyl]sulfonyl}(2Z)-3-(2,4-difluorophenyl)prop-2-enamide; bis{[(1E)-2-(4-fluorophenyl)vinyl]sulfonyl }amine; (2E)-N-{[(1E)-2-(4-fluorophenyl)vinyl]sulfonyl}-3-(4-fluorophenyl)prop-2-enamide;{[(1 E)-2-(4-fluorophenyl)vinyl]sulfonyl }{[(1Z)-2-(4-fluorophenyl)vinyl]sulfonyl}amine; (2E)-N-{[(1Z)-2-(4-fluorophenyl)vinyl]sulfonyl}-3-(4-fluorophenyl)prop-2-enamide; N-{[(1E)-2-(4-fluorophenyl)vinyl]sulfonyl}(2Z)-3-(4-fluorophenyl)prop-2-enamide; bis{[(1 E)-2-(4-chlorophenyl)vinyl]sulfonyl}amine; (2E)-N-{[(1E)-2-(4-chlorophenyl)vinyl]sulfonyl}-3-(4-chlorophenyl)prop-2-enamide;{[(1E)-2-(4-chlorophenyl)vinyl]sulfonyl} {[(1Z)-2-(4-chloro-phenyl)vinyl]sulfonyl}amine; (2E)-N-{[(1Z)-2-(4-chlorophenyl)vinyl]sulfonyl}-3-(4-chloro-phenyl)prop-2-enamide; N-{[(1E)-2-(4-chlorophenyl)vinyl]sulfonyl}(2Z)-3-(4-chlorophenyl)prop-2-enamide; bis{[(1E)-2-(4-bromophenyl)vinyl]sulfonyl}amine; (2E)-N-{[(1E)-2-(4-bromophenyl)vinyl]sulfonyl}-3-(4-bromophenyl)prop-2-enamide; {[(1E)-2-(4-bromophenyl)vinyl]sulfonyl}{[(1Z)-2-(4-bromophenyl)vinyl]sulfonyl}amine; (2E)-N-{[(1Z)-2-(4-bromophenyl)vinyl]sulfonyl}-3-(4-bromophenyl)prop-2-enamide; N-{[(1E)-2-(4-bromophenyl)vinyl]sulfonyl}(2Z)-3-(4-bromophenyl)prop-2-enamide; bis[((1E)-2-phenylvinypsulfonyl]amine; (2E)-N-[((1E)-2-phenylvinyl)sulfonyl]-3-phenylprop-2-enamide; [((1E)-2-phenylvinypsulfonyl][((1Z)-2-phenylvinypsulfonyl]amine; (2E)-N-[((1Z)-2-phenylvinyl)sulfonyl]-3-phenylprop-2-enamide; N-[((1E)-2-phenylvinyl)sulfonyl](2Z)-3-phenylprop-2-enamide; bis{[(1E)-2-(4-methoxy-3-nitrophenyl)vinyl]sulfonyl}amine; (2E)-N-{[(1E)-2-(4-methoxy-3-nitrophenyl)vinyl]sulfonyl}-3-(4-methoxy-3-nitrophenyl)prop-2-enamide; {[(1E)-2-(4-methoxy-3-nitrophenyl)vinyl]sulfonyl} {[(1Z)-2-(4-methoxy-3-nitrophenyl)vinyl]sulfonyl}amine; (2E)-N-{[(1Z)-2-(4-methoxy-3-nitrophenyl)vinyl]sulfonyl}-3-(4-methoxy-3-nitrophenyl)prop-2-enamide; N-{[(1E)-2-(4-methoxy-3-nitrophenyl)vinyl]-sulfonyl}(2Z)-3-(4-methoxy-3-nitrophenyl)prop-2-enamide; bis[((1E)-2-(3-thienyl)vinyl)-sulfonyl]amine; (2E)-N-[((1E)-2-(3-thienyl)vinyl)sulfonyl]-3-(3-thienyl)prop-2-enamide; [((1E)-2-(3-thienyl)vinyl)sulfonyl][((1Z)-2-(3-thienyl)vinyl)sulfonyl]amine; (2E)-N-[((1Z)-2-(3-thienyl)vinyl)sulfonyl]-3-(3-thienyl)prop-2-enamide; N-[((1E)-2-(3-thienyl)vinyl)sulfonyl](2Z)-3-(3-thienyl)prop-2-enamide; bis{[(1E)-2-(3-hydroxy-4-methoxyphenyl)vinyl]sulfonyl}amine; (2E)-N-{[(1E)-2-(3-hydroxy-4-methoxyphenyl)vinyl]sulfonyl}-3-(3-hydroxy-4-methoxyphenyl)prop-2-enamide;{[(1E)-2-(3-hydroxy-4-methoxyphenyl)vinyl]sulfonyl }{[(1Z)- 2-(3-hydroxy-4-methoxyphenyl)vinyl]sulfonyl}amine; (2E)-N-{[(1Z)-2-(3-hydroxy-4-methoxyphenyl)vinyl]sulfonyl}-3-(3-hydroxy-4-methoxyphenyl)prop-2-enamide; N-{[(1E)-2-(3-hydroxy-4-methoxyphenyl)vinyl]sulfonyl}(2Z)-3-(3-hydroxy-4-methoxyphenyl)prop-2-enamide; bis{[(1E)-2-(3-amino-4-methoxyphenyl)vinyl]sulfonyl}amine; (2E)-N-{[(1E)-2-(3-amino-4-methoxyphenyl)vinyl]sulfonyl}-3-(3-amino-4-methoxyphenyl)prop-2-enamide;{[(1E)-2-(3-amino-4-methoxyphenyl)vinyl]sulfonyl}{[(1Z)-2-(3-amino-4-methoxyphenyl)vinyl]sulfonyl}-amine; (2E)-N-{[(1Z)-2-(3-amino-4-methoxyphenyl)vinyl]sulfonyl}-3-(3-amino-4-methoxyphenyl)prop-2-enamide; N-{[(1E)-2-(3-amino-4-methoxyphenyl)vinyl]sulfonyl}(2Z)-3-(3-amino-4-methoxyphenyl)prop-2-enamide; bis{[(1E)-2-(4-iodophenyl)vinyl]sulfonyl}amine; (2E)-N-{[(1E)-2-(4-iodophenyl)vinyl]sulfonyl}-3-(4-iodophenyl)prop-2-enamide;{[(1E)-2-(4-iodophenyl)vinyl]sulfonyl} {[(1Z)-2-(4-iodophenyl)vinyl]sulfonyl}amine; (2E)-N-{[(1Z)-2-(4-iodopheniodophenyl)vinyl]sulfonyl}-3-(4-iodophenyl)prop-2-enamide; N-{[(1E)-2-(4-Z)-3-(4-iodophenyl)propyl)vinyl]sulfonyl}-3-(4-iodophenyl)prop-2-enamide; N-{[(1E)-2-(4-iodophenyl)vinyl]sulfonyl}(2Z)-3-(4-iodophenyl)prop-2-enamide; and salts thereof.

19. A compound or salt thereof according to claim 18 which is an isolated compound.

20. A compound or salt thereof according to claim 16 wherein $M^1$ is —S(=O)— and $M^2$ is selected from the group consisting of —S(=O)— and —C(=O)—.

21. A compound according to claim 20 selected from the group consisting of:
bis{[(1E)-2-(4-hydroxy-3-methoxyphenyl)vinyl]sulfinyl}amine; (2E)-N-{[(1E)-2-(4-hydroxy-3-methoxyphenyl)vinyl]sulfinyl}-3-(4-hydroxy-3-methoxyphenyl)prop-2-enamide; {[(1E)-2-(4-hydroxy-3-methoxyphenyl)vinyl]sulfinyl}{[(1Z)-2-(4-hydroxy-3-methoxyphenyl)vinyl]sulfinyl}amine; (2E)-N-{[(1Z)-2-(4-hydroxy-3-methoxyphenyl)-vinyl]sulfinyl}-3-(4-hydroxy-3-methoxyphenyl)prop-2-enamide; N-{[(1E)-2-(4-hydroxy-3-methoxyphenyl)vinyl]sulfinyl}(2Z)-3-(4-hydroxy-3-methoxyphenyl)prop-2-enamide; bis{[(1E)-2-(3,4,5-trimethoxyphenyl)vinyl]sulfinyl}amine; (2E)-N-{[(1E)-2-(3,4,5-trimethoxyphenyl)vinyl]sulfinyl}-3-(3,4,5-trimethoxyphenyl)prop-2-enamide; {[(1E)-2-(3,4,5-trimethoxyphenyl)vinyl]sulfinyl}{[(1Z)-2-(3,4,5-trimethoxyphenyl)vinyl]sulfinyl}amine; (2E)-N-{[(1Z)-2-(3,4,5-trimethoxyphenyl)vinyl]sulfinyl}-3-(3,4,5-trimethoxyphenyl)prop-2-enamide; N-{[(1E)-2-(3,4,5-trimethoxyphenyl)vinyl]sulfinyl}(2Z)-3-(3,4,5-trimethoxyphenyl)prop-2-enamide; bis{[(1E)-2-(2,3,4,5,6-pentafluorophenyl)vinyl]sulfinyl}amine; (2E)-N-{[(1E)-2-(2,3,4,5,6-pentafluorophenyl)vinyl]sulfinyl}-3-(2,3,4,5,6-pentafluorophenyl)prop-2-enamide; {[(1E)-2-(2,3,4,5,6-pentafluorophenyl)vinyl]sulfinyl}{[(1Z)-2-(2,3,4,5,6-pentafluorophenyl)vinyl]sulfinyl}amine; (2E)-N-{[(1Z)-2-(2,3,4,5,6-pentafluorophenyl)vinyl]sulfinyl}-3-(2,3,4,5,6-pentafluorophenyl)prop-2-enamide; N-{[(1E)-2-(2,3,4,5,6-pentafluorophenyl)vinyl]sulfinyl}(2Z)-3-(2,3,4,5,6-pentafluorophenyl)prop-2-enamide; bis{[(1E)-2-(2,4,6-trimethoxyphenyl)vinyl]sulfinyl}amine; (2E)-N-{[(1E)-2-(2,4,6-trimethoxyphenyl)vinyl]sulfinyl}-3-(2,4,6-trimethoxyphenyl)prop-2-enamide;{[(1E)-2-(2,4,6-trimethoxyphenyl)vinyl]sulfinyl}{[(1Z)-2-(2,4,6-trimethoxyphenyl)vinyl]sulfinyl}amine; (2E)-N-{[(1Z)-2-(2,4,6-trimethoxyphenyl)vinyl]sulfinyl}-3-(2,4,6-trimethoxyphenyl)prop-2-enamide; N-{[(1E)-2-(2,4,6-trimethoxyphenyl)vinyl]sulfinyl}(2Z)-3-(2,4,6-trimethoxyphenyl)prop-2-enamide; bis{[(1E)-2-(4-hydroxy-2,6-dimethoxyphenyl)vinyl]sulfinyl}amine; (2E)-N-{[(1E)-2-(4-hydroxy-2,6-dimethoxyphenyl)vinyl]sulfinyl}-3-(4-hydroxy-2,6-dimethoxyphenyl)prop-2-enamide; {[(1E)-2-(4-hydroxy-2,6-dimethoxyphenyl)vinyl]sulfinyl}{[(1Z)-2-(4-hydroxy-2,6-dimethoxyphenyl)vinyl]sulfinyl}amine; (2E)-N-{[(1Z)-2-(4-hydroxy-2,6-dimethoxyphenyl)vinyl]sulfinyl}-3-(4-hydroxy-2,6-dimethoxyphenyl)prop-2-enamide; N-{[(1E)-2-(4-hydroxy-2,6-dimethoxyphenyl)vinyl]sulfinyl}(2Z)-3-(4-hydroxy-2,6-dimethoxyphenyl)prop-2-enamide; bis{[(1E)-2-(2,6-dimethoxyphenyl)vinyl]sulfinyl}amine; (2E)-N-{[(1E)-2-(2,6-dimethoxyphenyl)vinyl]sulfinyl}-3-(2,6-dimethoxyphenyl)prop-2-enamide; {[(1E)-2-(2,6-dimethoxyphenyl)vinyl]sulfinyl}{[(1Z)-2-(2,6-dimethoxyphenyl)vinyl]sulfinyl}amine; (2E)-N-{[(1Z)-2-(2,6-dimethoxyphenyl)vinyl]sulfinyl}-3-(2,6-dimethoxyphenyl)prop-2-enamide; N-{[(1E)-2-(2,6-dimethoxyphenyl)vinyl]sulfinyl}(2Z)-3-(2,6-dimethoxyphenyl)prop-2-enamide; 4-{(1E)-2-[({[(1E)-2-(4-cyano-2-fluorophenyl)vinyl]sulfinyl}amino)sulfinyl]vinyl}-3-fluorobenzenecarbonitrile; (2E)-N-{[1E)-2-(4-cyano-2-fluorophenyl)vinyl]sulfinyl}-3-(4-cyano-2-fluorophenyl)prop-2-enamide; 4-{(1E)-2-[({[(1Z)-2-(4-cyano-2-fluorophenyl)vinyl]sulfinyl}amino)sulfinyl]vinyl}-3-fluorobenzenecarbonitrile; (2E)-N-{[(1Z)-2-(4-cyano-2-fluorophenyl)vinyl]sulfinyl}-3-(4-cyano-2-fluorophenyl)prop-2-enamide; N-{[(1E)-2-(4-cyano-2-fluorophenyl)vinyl]sulfinyl}(2Z)-3-(4-cyano-2-fluorophenyl)prop-2-enamide; bis{[(1E)-2-(2,4-difluorophenyl)vinyl]sulfinyl}amine; (2E)-N-{[(1E)-2-(2,4-difluorophenyl)vinyl]sulfinyl}-3-(2,4-difluorophenyl)prop-2-enamide; {[(1E)-2-(2,4-difluorophenyl)vinyl]sulfinyl}{[(1Z)-2-(2,4-difluorophenyl)vinyl]sulfinyl}amine; (2E)-N-{[(1Z)-2-(2,4-difluorophenyl)vinyl]sulfinyl}-3-(2,4-difluorophenyl)prop-2-enamide; N-{[(1E)-2-(2,4-difluorophenyl)vinyl]sulfinyl}(2Z)-3-(2,4-difluorophenyl)prop-2-enamide; bis{[(1E)-2-(4-fluorophenyl)vinyl]sulfinyl}amine; (2E)-N-{[(1E)-2-(4-fluorophenyl)-vinyl]sulfinyl}-3-(4-fluorophenyl)prop-2-enamide; {[(1E)-2-(4-fluorophenyl)vinyl]sulfinyl}-{[(1Z)-2-(4-fluorophenyl)vinyl]sulfinyl}amine; (2E)-N-{[(1Z)-2-(4-fluorophenyl)vinyl]sulfinyl}-3-(4-fluorophenyl)prop-2-enamide; N-{[(1E)-2-(4-fluorophenyl)vinyl]sulfinyl}(2Z)-3-(4-fluorophenyl)prop-2-enamide; bis{[(1E)-2-(4-chlorophenyl)vinyl]sulfinyl}amine; (2E)-N-{[(1E)-2-(4-chlorophenyvinyl]sulfinyl}-3-(4-chlorophenyl)prop-2-enamide; {[(1E)-2-(4- hlorophenyl)vinyl]sulfinyl}{[(1Z)-2-(4-chlorophenyl)vinyl]sulfinyl}amine; (2E)-N-{[(1Z)-2-(4-chlorophenyl)vinyl]sulfinyl}-3-(4-chlorophenyl)prop-2-enamide; N-{[(1E)-2-(4-chlorophenyl)vinyl]sulfinyl}(2Z)-3-(4-chlorophenyl)prop-2-enamide; bis{[(1E)-2-(4-bromophenyl)vinyl]sulfinyl}amine; (2E)-N-{[(1E)-2-(4-bromophenyl)vinyl]sulfinyl}-3-(4-bromophenyl)prop-2-enamide; {[(1E)-2-(4-bromophenyl)vinyl]sulfinyl}{[(1Z)-2-(4-bromophenyl)vinyl]sulfinyl}amine; (2E)-N-{[(1Z)-2-(4-bromophenyl)vinyl]sulfinyl}-3-(4-bromophenyl)prop-2-enamide; N-{[(1E)-2-(4-bromophenyl)vinyl]sulfinyl}(2Z)-3-(4-bromophenyl)prop-2-enamide; bis[((1E)-2-phenylvinyl)sulfinyl]amine; (2E)-N-[((1E)-2-phenylvinyl)sulfinyl]-3-phenylprop-2-enamide; [((1E)-2-phenylvinyl)sulfinyl][((1Z)-2-phenylvinyl)sulfinyl]amine; (2E)-N-[((1Z)-2-phenylvinyl)sulfinyl]-3-phenylprop-2-enamide; N-[((1E)-2-phenylvinyl)sulfinyl](2Z)-3-phenylprop-2-enamide; bis{[(1E)-2-(4-methoxy-3-nitrophenyl)vinyl]sulfinyl}amine; (2E)-N-{[(1E)-2-(4-methoxy-3-nitrophenyl)vinyl]sulfinyl}-3-(4-methoxy-3-nitrophenyl)prop-2-enamide;{[(1E)-2-(4-methoxy-3-nitrophenyl)vinyl-sulfinyl}{[(1Z)-2-(4-methoxy-3-nitrophenyl)vinyl]sulfinyl}amine; (2E)-N-{[(1Z)-2-(4-methoxy-3-nitrophenyl)vinyl]sulfinyl}-3-(4-methoxy-3-nitrophenyl)prop-2-enamide; N-{[(1E)-2-(4-methoxy-3-nitrophenyl)vinyl]sulfinyl}(2Z)-3-(4-methoxy-3-nitrophenyl)prop-2-enamide; bis[((1E)-2-(3-thienyl)vinyl)sulfinyl]amine; (2E)-N-[((1E)-2-(3-thienyl)vinyl)sulfinyl]-3-(3-thienyl)prop-2-enamide; [((1E)-2-(3-thienyl)vinyl)sulfinyl][((1Z)-2-(3-thienyl)vinyl)-sulfinyl]amine; (2E)-N-[((1Z)-2-(3-thienyl)vinyl)sulfinyl]-3-(3-thienyl)prop-2-enamide; N-[((1E)-2-(3-thienyl)vinyl)sulfinyl](2Z)-3-(3-thienyl)prop-2-enamide; bis{[(1E)-2-(3-hydroxy-4-methoxyphenyl)vinyl]sulfinyl}amine; (2E)-N-{[(1E)-2-(3-hydroxy-4-methoxy-phenyl)vinyl]sulfinyl}-3-(3-hydroxy-4-methoxyphenyl)prop-2-enamide; {[(1E)-2-(3-hydroxy-4-methoxyphenyl)vinyl]sulfinyl}{[(1Z)-2-(3-hydroxy- 4-methoxyphenyl)vinyl]sulfinyl}amine; (2E)-N-{[(1Z)-2-(3-hydroxy-4-methoxyphenyl)vinyl]sulfonyl}-3-(3-hydroxy-4-methoxyphenyl)prop-2-enamide; N-{[(1E)-2-(3-hydroxy-4-methoxyphenyl)vinyl]sulfinyl}(2Z)-3-(3-hydroxy-4-methoxyphenyl)prop-2-enamide; bis{[(1E)-2-(3-amino-4-methoxyphenyl)vinyl]sulfinyl}amine; (2E)-N-{[(1E)-2-(3-amino-4-methoxyphenyl)-vinyl]sulfinyl}-3-(3-amino-4-methoxyphenyl)prop-2-enamide; {[(1E)-2-(3-amino-4-methoxyphenyl)vinyl]sulfinyl}{[(1Z)-2-(3-amino-4-methoxyphenyl)vinyl]sulfinyl}amine; (2E)-N-{[(1Z)-2-(3-amino-4-methoxyphenyl)vinyl]sulfinyl}-3-(3-amino-4-methoxyphenyl)prop-2-enamide; N-{[(1E)-2-(3-amino-4-methoxyphenyl)vinyl]sulfinyl}(2Z)-3-(3-amino-4-methoxyphenyl)prop-2-enamide; bis{[(1E)-2-(4-iodophenyl)vinyl]sulfinyl}amine; (2E)-N-{[(1E)-2-(4-iodophenyl)vinyl]sulfinyl}-3-(4-iodophenyl)prop-2-enamide;{[(1E)-2-(4-iodophenyl)vinyl]sulfinyl}{[(1Z)-2-(4-iodophenyl)vinyl]sulfinyl}amine; (2E)-N-{[(1Z)-2-(4-iodophenyl)vinyl]sulfinyl}-3-(4-iodophenyl)prop-2-enamide; N-{[(1E)-2-(4-iodophenyl)vinyl]sulfinyl}(2Z)-3-(4-iodophenyl)prop-2-enamide; and salts thereof.

22. A compound or salt thereof according to claim 21 which is an isolated compound.

23. A pharmaceutical composition comprising a pharmaceutically acceptable carrier and a compound, or a pharmaceutically acceptable salt thereof, according to claim 1.

24. A method of treating an individual for a proliferative disorder selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's Disease of the bone, fibrocystic disease of the breast, uterine fibroids, Peyronie' disease, Dupuytren's disease, restenosis, benign proliferative breast disease, benign prostatic hyperplasia, X-linked lymphoproliferative disorder, post-transplantation lymphoproliferative disorder, macular degeneration, retinopathies, proliferative vitreoretinopathy and non-cancerous lymphoproliferative disorders, comprising administering to said individual an effective amount of a compound according to Formula IC:

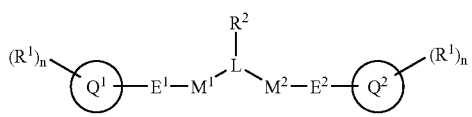

wherein:
$Q^1$ and $Q^2$ are independently selected from the group consisting of aryl and heteroaryl;
each $R^1$ is independently selected from the group consisting of halogen, —($C_1$-$C_8$)hydrocarbyl,—C(=O)$R^y$, —NR$^w{}_2$, —N($R^W$)C(=O)$R^y$, —N($R^W$)CH($R^Z$)C(=O)$R^y$, —N($R^{w)SO_2}R^y$, —N($R^w$)($C_1$-$C_4$)alkylene-CO$_2$$R^w$, —NO$_2$, —CN, —O $R^w$, —OC(=O)$R^y$, —OCH($R^z$)C(=O)$R^y$, —OSO$_2$$R^y$,—O($C_1$-$C_4$)alkylene-CO$_2$$R^w$, —OP(=O)(O$R^w$)$_2$, —O($C_2$-$C_6$)alkylene-N(CH$_3$)$_2$, —O($C_1$-$C_6$)haloalkyl, —P(=O)(O$R^w$)$_2$, —SO$_2$N($R^w$)$R^x$, —NHC(=NH)NHR$^x$, —($C_1$-$C_6$)haloalkyl and heteroalkyl;
each $R^w$ is independently —H or —($C_1$-$C_8$)hydrocarbyl;
each $R^x$ is independently —H, —($C_1$-$C_8$)hydrocarbyl or —C(=O)($C_1$-$C_8$)hydrocarbyl;
each $R^y$ is independently selected from the group consisting of —H, —($C_1$-$C_8$)hydrocarbyl, —O($C_1$-$C_8$)hydrocarbyl, substituted phenyl, substituted heterocyclyl($C_1$-$C_3$)alkyl, heteroaryl($C_1$-$C_3$)alkyl, —($C_2$-$C_{10}$)heteroalkyl, —($C_1$-$C_6$)haloalkyl, —C($R^z$)NHR$^x$, —N($R^W$)$R^x$, —($C_1$-$C_3$)alkyleneNH$_2$, —($C_1$-$C_3$)alkyleneN(CH$_3$)$_2$, —($C_1$-$C_3$)perfluoroalkyleneN(CH$_3$)$_2$, —($C_1$-$C_3$)alkyleneN$^+$(($C_1$$C_3$)alkyl)$_3$, —($C_1$-$C_3$)alkylene-N$^+$(CH$_2$CH$_2$OH)$_3$, —($C_1$-$C_3$)alkylene-O$R^x$, —($C_1$-$C_4$)alkylene-CO$_2$$R^w$, —($C_1$-$C_4$)alkylene-CO$_2$N($R^w$)$R^x$, —($C_1$-$C_4$)alkylene-C(=O)halogen, halo($C_1$-$C_3$)alkyl and —($C_1$-$C_4$)perfluoroalkylene-CO$_2$$R^w$;
each $R^3$ is independently selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);
each n is independently 0, 1, 2, 3, 4 or 5;
$M^1$ and $M^2$ are independently —SO$_2$-, —S(=O)— or —C(=O)—;
L is CH or N;
$R^2$ is selected from the group consisting of —H and —($C_1$-$C_6$)alkyl; and
$E^1$ and $E^2$ are independently selected from the group consisting of a carbon-carbon double bond in the (E)-configuration and a carbon-carbon double bond in the (Z)-configuration;
provided that:
(i) when one of $M^1$ and $M^2$ is —SO$_2$—, then the other of $M^1$ and $M^2$ is other than —S(=O)—;
(ii) when one of $M^1$ and $M^2$ is —C(=O)—, then the other of $M^1$ and $M^2$ is other than —C(=O)—; and
(iii) when one of $E^1$ and $E^2$ is a carbon-carbon double bond in the (Z)-configuration, then the other of $E^1$ and $E^2$ is a carbon-carbon double bond in the (E)-configuration; or a salt of such a compound.

25. A method of treating an individual for a cancer selected from the group consisting of ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia, comprising administering to said individual an effective amount of a compound according to Formula IC:

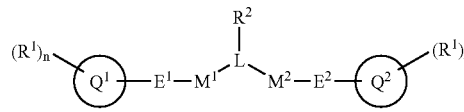

wherein:
$Q^1$ and $Q^2$ are independently selected from the group consisting of aryl and heteroaryl;
each $R^1$ is independently selected from the group consisting of halogen, —($C_1$-$C_8$)hydrocarbyl, —C(=O)$R^y$, —NR$^w{}_2$, —N($R^w$)C(=O)$R^y$, —N($R^w$)CH($R^z$)C(=O)$R^y$, 13 N($R^w$)SO$_2$$R^y$, 13 N($R^w$)($C_1$-$C_4$)alkylene-CO$_2$$R^w$, 13 NO$_2$, —CN, —O$R^w$, —OC(=O)$R^y$, —OCH($R^z$)C(=O)$R^y$, —OSO$_2$$R^y$, —($C_1$-$C_4$)alkylene-CO$_2$$R^w$, —OP(=O)(O$R^w$)$_2$, —O($C_2$-$C_6$)alkylene-N(CHD$_2$, —O($C_1$-$C_6$)haloalkyl, —P(=O)(O$R^w$)$_2$, —SO,N($R^w$)$R^x$, —NHC(=NH)NH$R^x$, —($C_1$-$C_6$)haloalkyl and heteroalkyl;

each $R^w$ is independently —H or —($C_1$-$C_a$)hydrocarbyl;

each $R^x$ is independently —H, —($C_1$-$C_8$)hydrocarbyl or —C(=O)($C_1$-$C_8$)hydrocarbyl;

each $R^y$ is independently selected from the group consisting of —H, —($C_1$-$C_8$)hydrocarbyl, —($C_1$-$C_8$)hydrocarbyl, substituted phenyl, substituted heterocyclyl(C)alkyl, heteroaryl($C_1$-$C_3$)alkyl, —($C_2$-$C_{10}$)heteroalkyl, —($C_1$-$C_6$)haloalkyl, —C($R^z$)NH$R^x$, —N($R^w$)$R^x$, —($C_1$-$C_3$)alkyleneNH$_2$, —($C_1$-$C_3$)alkyleneN(CH$_3$)$_2$, —($C_{1-3}$)perfluoroalkyleneN(CH$_3$)$_2$—($C_1$$C_3$)alkyleneN$^+$(($C_1$$C_3$)alkyl)$_3$, —($C_1$$C_3$)alkylene-N$^+$(CH,CH$_2$OH)$_3$, —($C_1$$C_3$)alkylene-O$R^x$, —($C_1$-$C_4$)alkylene-CO$_2$$R^w$, —($C_1$-$C_4$)alkylene-CO$_2$N($R^w$)$R^x$, —($C_1$-$C_4$)alkylene-C(=O)halogen, halo($C_{13}$)alkyl and —($C_1$-$C_4$)perfluoroalkylene-CO$_2$$R^w$ each $R^Z$ is independently selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);

each n is independently 0, 1, 2, 3, 4 or 5;

$M^1$ and $M^2$ are independently —SO$_2$—, —S(=O)—or —C(=O)—;

L is CH or N;

$R^2$ is selected from the group consisting of —H and —($C_1$-$C_6$)alkyl; and $E^1$ and $E^2$ are independently selected from the group consisting of a carbon-carbon double bond in the (E)-configuration and a carbon-carbon double bond in the (Z)-configuration;

provided that:
(i) when one of $M^1$ and $M^2$ is —SO$_2$—, then the other of $M^1$ and $M^2$ is other than —S(=O)—;
(ii) when one of $M^1$ and $M^2$ is —C(=O)—, then the other of $M^1$ and $M^2$ is other than —C(=O)—; and
(iii) when one of $E^1$ and $E^2$ is a carbon-carbon double bond in the (Z)-configuration, then the other of $E^1$ and $E^2$ is a carbon-carbon double bond in the (E)-configuration; or a salt of such a compound.

26. A method of inducing apoptosis of tumor cells in an individual afflicted with cancer comprising administering to said individual an effective amount of a compound according to Formula IC:

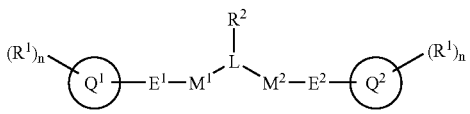

IC wherein:
$Q^1$ and $Q^2$ are independently selected from the group consisting of aryl and heteroaryl;

each $R^1$ is independently selected from the group consisting of halogen, —($C_1$-$C_8$)hydrocarbyl, —C(=O)R, —N$R^w$$_2$, —N($R^w$)C(=O)$R^y$, —N($R^w$)CH($R^Z$)C(=O)$R^y$, —N($R^w$)SO$_2$$R^y$, —N($R^w$)($C_1$-$C_4$)alkylene-CO$_2$$R^w$, —NO$_2$, —CN, —O$R^w$, —OC(=O)$R^y$, —OCH($R^z$)C(=O)$R^y$, —OSO$_2$$R^y$, —O($C_1$-$C_4$)alkylene-CO$_2$$R^w$, —OP(=O)(O$R^w$)$_2$, —O($C_2$-$C_6$)alkylene-N(CH$_3$)$_2$, —O($C_1$-$C_6$)haloalkyl, —P(=O)(O$R^w$)$_2$, —SO$_2$N($R^w$)$R^x$, —NHC(=NH)NH$R^x$, —($C_1$-$C_6$)haloalkyl and heteroalkyl;

each $R^w$ is independently —H or —($C_1$-$C_8$)hydrocarbyl;

each $R^x$ is independently —H, —($C_1$-$C_8$)hydrocarbyl or —C(=O)($C_1$-$C_8$)hydrocarbyl;

each $R^y$ is independently selected from the group consisting of —H, —($C_1$-$C_8$)hydrocarbyl, —O($C_1$-$C_8$)hydrocarbyl, substituted phenyl, substituted heterocyclyl($C_1$-$C_3$)alkyl, heteroaryl($C_1$-$C_3$)alkyl, —($C_2$-$C_{10}$)heteroalkyl, —($C_1$-$C_6$)haloalkyl, —C($R^z$)NH$R^x$, —N($R^w$)$R^x$, —($C_1$-$C_3$)alkyleneNH$_2$, —($C_1$-$C_3$)alkyleneN(CH$_3$)$_2$, —($C_1$-$C_3$)perfluoroalkyleneN(CH$_3$)$_2$, —($C_1$$C_3$)alkyleneN$^+$(($C_1$-$C_3$)alkyl)$_3$, —($C_1$-$C_3$)alkylene-N$^+$(CH$_2$CH$_2$OH)$_3$, —($C_1$-$C_3$)alkylene-O$R^x$, —($C_1$-$C_4$)alkylene-CO$_2$$R^w$, —($C_1$-$C_4$)alkylene-CO$_2$N($R^w$)$R^x$, —($C_1$-$C_4$)alkylene-C(=O)halogen, halo($C_1$-$C_3$)alkyl and —($C_1$-$C_4$)perfluoroalkylene-CO$_2$$R^w$;

each $R^z$ is independently selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, 4CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);

each n is independently 0, 1, 2, 3, 4 or 5;

$M^1$ and $M^2$ are independently —SO$_2$—, —S(=O)—or —C(=O)—;

L is CH or N;

$R^2$ is selected from the group consisting of —H and —($C_1$-$C_6$)alkyl; and $E^1$ and $E^2$ are independently selected from the group consisting of a carbon-carbon double bond in the (E)-configuration and a carbon-carbon double bond in the (Z)-configuration;

provided that:
(i) when one of $M^1$ and $M^2$ is —SO$_2$—, then the other of $M^1$ and $M^2$ is other than —S(=O)—;
(ii) when one of $M^1$ and $M^2$ is —C(=O)—, then the other of $M^I$ and $M^2$ is other than —C(=O)—; and
(iii) when one of $E^i$ and $E^2$ is a carbon-carbon double bond in the (Z)-configuration, then the other of $E^I$ and $E^2$ is a carbon-carbon double bond in the (E)-configuration; or a salt of such a compound.

27. A method according to claim 26 wherein the tumor cells are selected from the group consisting of ovarian, cervical, breast, prostate, testicular, lung, renal, colorectal, skin and brain tumor cells.

28. A method of treating an individual for an angiogenesis-mediated disorder comprising administering to said individual an effective amount of a compound according to Formula IC:

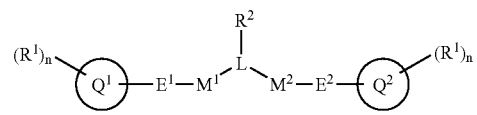

IC wherein:
$Q^1$ and $Q^2$ are independently selected from the group consisting of aryl and heteroaryl;

each $R^1$ is independently selected from the group consisting of halogen, —($C_1$-$C_8$)hydrocarbyl, —C(=O)$R^y$, —NR$^w{}_2$, —N(R$^w$)C(=O)R$^y$, —N(R$^w$)CH(e)C(=O)R$^y$, —N(R$^w$)SO$_2$R$^y$, —N(R$^w$)(C$_1$-C$_4$)alkylene-CO$_2$R$^w$, —NO$_2$, —CN, —OR$^w$ —OC(=O)R$^y$, —OCH(R$^z$)C(=O)R$^y$, —OSO$_2$R$^y$, —O(C$_1$-C$_4$)alkylene-CO$_2$R$^w$, —OP(=O)(OR$^w$)$_2$, —O(C$_2$-C$_6$)alkylene-N(CH$_3$)$_2$, —O(C$_1$-C$_6$)haloalkyl, —P(=O)(OR$^w$)$_2$, —SO$_2$N(R$^w$)R$^x$, —NHC(=NH)NHR$^x$, —(C$_1$-C$_6$)haloalkyl and heteroalkyl;

each R$^w$ is independently —H or —(C$_1$-C$_8$)hydrocarbyl;

each R$^x$ is independently —H, —(C$_1$-C$_8$)hydrocarbyl or —C(=O)(C$_1$-C$_8$)hydrocarbyl;

each R$^y$ is independently selected from the group consisting of —H, —(C$_1$-C$_8$)hydrocarbyl, —O(C$_1$-C$_8$)hydrocarbyl, substituted phenyl, substituted heterocyclyl(C$_1$-C$_3$)alkyl, heteroaryl(C$_1$-C$_3$)alkyl, —(C$_2$-C$_{10}$)heteroalkyl, —(C$_1$-C$_6$)haloalkyl, —C(R$^z$)NHR$^x$, —N(R$^W$)R$^x$, —(C$_1$-C$_3$)alkyleneNH$_2$, —(C$_1$-C$_3$)alkyleneN(CH$_3$)$_2$, —(C$_1$-C$_3$)perfluoroalkyleneN(CH$_3$)$_2$, —(C$_1$-C$_3$)alkyleneN$^+$((C$_{1-3}$)alkyl)$_3$, —(C$_1$-C$_3$)alkylene-N$^+$(CH$_2$CH$_2$OH)$_3$, —(C$_1$-C$_3$)alkylene-OR$^x$, —(C$_1$-C$_4$)alkylene-CO$_2$R$^w$, —(C$_1$-C$_4$)alkylene-CO$_2$N(R$^w$)R$^x$, —(C$_1$-C$_4$)alkylene-C(=O)halogen, halo(C$_1$-C$_3$)alkyl and —(C$_1$-C$_4$)perfluoroalkylene-CO$_2$R$^w$;

each R$^z$ is independently selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);

each n is independently 0, 1, 2, 3, 4 or 5;

M$^1$ and M$^2$ are independently —SO$_2$—, —S(=O)— or —C(=O)—;

L is CH or N;

R$^2$ is selected from the group consisting of —H and —(C$_1$-C$_6$)alkyl; and

E$^1$ and E$^2$ are independently selected from the group consisting of a carbon-carbon double bond in the (E)-configuration and a carbon-carbon double bond in the (Z)-configuration;

provided that:
(i) when one of M$^1$ and M$^2$ is —SO$_2$—, then the other of M$^1$ and M$^2$ is other than —S(=O)—;
(ii) when one of M$^1$ and M$^2$ is —C(=O)—, then the other of M$^1$ and M$^2$ is other than —C(=O)—; and
(iii) when one of E$^1$ and E$^2$ is a carbon-carbon double bond in the (Z)-configuration, then the other of E$^1$ and E$^2$ is a carbon-carbon double bond in the (E)-configuration; or a salt of such a compound.

29. A method of treating an individual for age related senile dementia comprising administering to said individual an effective amount of a compound according to Formula IC:

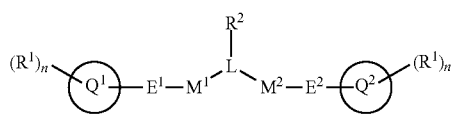

IC wherein:

Q$^1$ and Q$^2$ are independently selected from the group consisting of aryl and heteroaryl;

each R$^1$ is independently selected from the group consisting of halogen, —(C$_1$-C$_8$)hydrocarbyl, —C(=O)R$^y$, —NR$^W{}_2$, —N(R$^w$)C(=O)R$^y$, —N(R$^w$)CH(R$^z$)C(=O)R$^y$, —N(R$^w$)SO$_2$R$^y$, —N(R$^w$)(C$_1$-C$_4$)alkylene-CO$_2$R$^w$, —NO$_2$, —CN, —OR$^w$, —OC(=O)R$^y$, —OCH(R$^z$)C(=O)R$^y$, —OSO$_2$R$^y$, —O(C$_1$-C$_4$)alkylene-CO$_2$R$^w$, —OP(=O)(OR$^w$)$_2$, —O(C$_2$-C$_6$)alkylene-N(CH$_3$)$_2$, —O(C$_1$-C$_6$)haloalkyl, —P(=O)(OR$^w$)$_2$, —SO$_2$N(R$^w$)R$^x$, —NHC(=NH)NHR$^x$, —(C$_1$-C$_6$)haloalkyl and heteroalkyl;

each R$^W$ is independently —H or —(C$_1$-C$_8$)hydrocarbyl;

each R$^x$ is independently —H, —(C$_1$-C$_8$)hydrocarbyl or —C(=O)(C$_1$-C$_8$)hydrocarbyl;

each R$^y$ is independently selected from the group consisting of —(C$_1$-C$_8$)hydrocarbyl, —O(C$_1$-C$_8$)hydrocarbyl, substituted phenyl, substituted heterocyclyl(C$_1$-C$_3$)alkyl, heteroaryl(C$_1$-C$_3$)alkyl, —(C$_2$-C$_{10}$)heteroalkyl, —(C$_1$-C$_6$)haloalkyl, —C(R$^z$)NHR$^x$, —N(R$^W$)R$^x$, —(C$_1$-C$_3$)alkyleneNH$_2$, —(C$_1$-C$_3$)alkyleneN(CH$_3$)$_2$, —(C$_1$-C$_3$)perfluoroalkyleneN(CH$_3$)$_2$, —(C$_1$C$_3$)alkyleneN$^+$((C$_1$-C3)alkyl)$_3$, —(C$_1$-C$_3$)alkylene-N$^+$(CH$_2$CH$_2$OH)$_3$, —(C$_1$-C$_3$)alkylene-OR$^x$, —(C$_1$-C$_4$)alkylene-CO$_2$R$^w$, —(C$_1$-C$_4$)alkylene-CO$_2$N(R$^w$)R$^x$, —(C$_1$-C$_4$)alkylene-C(=O)halogen, halo(C$_1$-C$_3$)alkyl and —(C$_1$-C$_4$)perfluoroalkylene-CO$_2$R$^w$;

each R$^z$ is independently selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);

each n is independently 0, 1, 2, 3, 4 or 5;

M$^1$ and M$^2$ are independently —SO$_2$—, —S(=O)— or —C(=O)—;

L is CH or N;

R$^2$ is selected from the group consisting of —H and —(C$_1$-C$_6$)alkyl; and

E$^1$ and E$^2$ are independently selected from the group consisting of a carbon-carbon double bond in the (E)-configuration and a carbon-carbon double bond in the (Z)-configuration;

provided that:
(i) when one of M$^1$ and M$^2$ is —SO$_2$—, then the other of M$^1$ and M$^2$ is other than —S(=O)—;
(ii) when one of M$^1$ and M$^2$ is —C(=O)—, then the other of M$^1$ and M$^2$ is other than —C(=O)—; and
(iii) when one of E$^1$ and E$^2$ is a carbon-carbon double bond in the (Z)-configuration, then the other of E$^1$ and E$^2$ is a carbon-carbon double bond in the (E)-configuration; or a salt of such a compound.

30. A process for preparing a compound according to claim 1 wherein M, R$^1$, R$^2$, M$^1$, M$^2$ and n are as defined in claim 1; E$^1$ and E$^2$ represent carbon-carbon double bonds having an (E)-configuration; Q$^1$ is identical to Q$^2$; and the R$^1$ substituents on Q$^1$ are identical to the R$^1$ substituents on Q$^2$; said process comprising the steps of:

(a) reacting a compound according to Formula IIA:

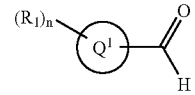

IIA with a compound of Formula IV:

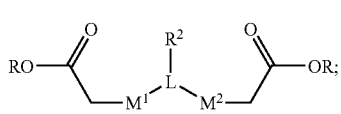

(IV)

wherein $R^2$, $M^1$, $M^2$ and L are as defined in claim 1; and R is —H or —$(C_1$-$C_7)$hydrocarbyl; and (b) isolating a compound according to claim 1 from the reaction products.

31. A process for preparing a compound according to claim 1 wherein M, $R^1$, $R^2$, $E^1$, $M^1$, $M^2$ and n are as defined in claim 1, and $E^2$ represents carbon-carbon double bond having an (E)-configuration; said process comprising the steps of:

(a) reacting a compound according to Formula IVA:

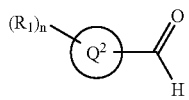

(IVA)

with a compound of Formula V:

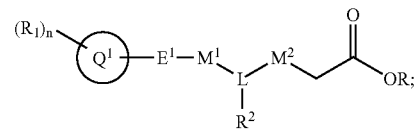

(V)

wherein $R^1$, n, $Q^1$, $M^1$, $M^2$, $R^2$ and L are as defined in claim 1, and R is —H or —$(C_1$-$C_7)$hydrocarbyl; and (b) isolating a compound according to claim 1 from the reaction products.

32. A method according to claim 25 wherein the cancer is prostate cancer.

33. A method according to claim 27 wherein the tumor cells comprise prostate tumor cells.

* * * * *